US009663755B2

(12) United States Patent
Nosrati et al.

(10) Patent No.: US 9,663,755 B2
(45) Date of Patent: May 30, 2017

(54) APPARATUS AND METHODS FOR SPERM SEPARATION

(71) Applicants: THE GOVERNING COUNCIL OF THE UNIVERSITY OF TORONTO, Toronto (CA); THE ROYAL INSTITUTION FOR THE ADVANCEMENT OF LEARNING/MCGILL UNIVERSITY, Montreal (CA)

(72) Inventors: Reza Nosrati, Toronto (CA); Lise Marie Eamer, York (CA); Marion Vollmer, Munich (DE); David Allan Sinton, Toronto (CA); Armand Zini, Cote St-Luc (CA)

(73) Assignees: THE GOVERNING COUNCIL OF THE UNIVERSITY OF TORONTO, Toronto (CA); THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 67 days.

(21) Appl. No.: 14/547,606

(22) Filed: Nov. 19, 2014

(65) Prior Publication Data
US 2015/0140655 A1 May 21, 2015

Related U.S. Application Data

(60) Provisional application No. 61/906,231, filed on Nov. 19, 2013.

(51) Int. Cl.
*C12N 5/076* (2010.01)
*C12M 1/00* (2006.01)
*C12M 3/00* (2006.01)

(52) U.S. Cl.
CPC ............ *C12M 47/04* (2013.01); *C12M 21/06* (2013.01)

(58) Field of Classification Search
None
See application file for complete search history.

(56) References Cited

U.S. PATENT DOCUMENTS

| 4,176,953 A | 12/1979 | Bartoov et al. |
| 4,402,614 A | 9/1983 | Porath-Furedi |
| 4,759,344 A | 7/1988 | Wang |
| 4,824,247 A | 4/1989 | True et al. |
| 4,896,967 A | 1/1990 | Douglas-Hamilton et al. |
| 5,093,866 A | 3/1992 | Douglas-Hamilton et al. |
| 5,427,946 A | 6/1995 | Kricka et al. |
| 5,686,302 A | 11/1997 | Zech |
| 5,744,366 A | 4/1998 | Kricka et al. |
| 5,866,354 A | 2/1999 | Froman |
| 5,908,380 A | 6/1999 | Zavos et al. |
| D421,129 S | 2/2000 | Haynes |
| 6,357,596 B1 | 3/2002 | Weichselbaum et al. |
| 6,426,213 B1 | 7/2002 | Eisenson |
| 6,783,928 B2 | 8/2004 | Hvichia et al. |
| 6,929,945 B2 | 8/2005 | Aravanis et al. |
| 7,179,641 B2 | 2/2007 | Brickwood |
| 7,355,696 B2 | 4/2008 | Mueth et al. |
| 7,718,124 B2 | 5/2010 | Simmet |
| 7,807,452 B2 | 10/2010 | Douglas-Hamilton et al. |
| 2006/0144707 A1 | 7/2006 | Landers et al. |
| 2010/0291535 A1 | 11/2010 | Yao et al. |
| 2011/0061472 A1 | 3/2011 | Wo et al. |
| 2013/0029312 A1 | 1/2013 | Johnston |
| 2013/0143200 A1 | 6/2013 | Sun et al. |

FOREIGN PATENT DOCUMENTS

| EP | 0095386 B1 | 10/1987 |
| EP | 0437408 A2 | 7/1991 |
| EP | 0439893 A2 | 8/1991 |

(Continued)

OTHER PUBLICATIONS

Galajda et al., "A Wall of Funnels Concentrates Swimming Bacteria", Journal of Bacteriology 2007, vol. 189, pp. 8704-8707.*
A. Agarwal, T. M. Said, "Role of sperm chromatin abnormalities and DNA damage in male infertility" Human Reproduction Update, vol. 9, No. 4, pp. 331-345, 2003.
A. Aharoni et al., "High-thoughput screening methodology for the directed evolution of glycosyltransferases" Nature Methods, vol. 3, No. 8, pp. 609-614, Aug. 2006.
A. Ahmadi et al., "Fertilizing Ability of DNA-Damaged Spermatozoa" Journal of Experimental Zoology 284: pp. 696-704, 1999.
A. Souza Setti et al., "Intracytoplasmic sperm injection outcome versus intracytoplasmic morphologically selected sperm injection outcome: a meta-analysis" Reproductive BioMedicine Online, 21, pp. 450-455, 2010.
A. T. Ohta et al., "Motile and non-motile sperm diagnostic manipulation using optoelectronic tweezers", Lab Chip, 2010, 10, pp. 3213-3217.

(Continued)

*Primary Examiner* — Renee Claytor
*Assistant Examiner* — Michelle F Paguio Frising
(74) *Attorney, Agent, or Firm* — Bereskin & Parr LLP/S.E.N.C.R.L., s.r.l.; Tony Orsi; Christopher Bury

(57) ABSTRACT

Various embodiments of methods and apparatuses for separating sperm, including apparatus having an inlet and an outlet reservoir, and either: i) a radial array of microchannels disposed between the inlet and outlet reservoirs to provide fluid communication therebetween and to direct motile sperm inwardly from the inlet reservoir to the outlet reservoir; or ii) at least one microchannel path disposed between the inlet and outlet reservoirs to provide fluid communication therebetween, the at least one microchannel path having a path inlet adjacent the inlet reservoir, a path outlet adjacent the outlet reservoir, and a junction located between the path inlet and the path outlet for directing a portion of sperm that enter the path inlet towards the outlet reservoir based on wall-swimming behavior of sperm. Methods include filling an apparatus with buffer fluid, introducing semen into an inlet reservoir, and retrieving sperm separated from the semen from the outlet reservoir.

12 Claims, 26 Drawing Sheets

(56) References Cited

FOREIGN PATENT DOCUMENTS

| EP | 1432787 B1 | 10/2002 | |
|---|---|---|---|
| EP | 1401342 B1 | 1/2005 | |
| IR | WO 02102968 A1 * | 12/2002 | ........... A61B 17/425 |
| SG | WO 2013115725 A1 * | 8/2013 | ........... C12M 47/04 |
| WO | 0160968 A1 | 8/2001 | |
| WO | 02102968 A1 | 12/2002 | |
| WO | 2004053465 A2 | 6/2004 | |
| WO | 2004108011 A1 | 12/2004 | |
| WO | 2012163087 A1 | 12/2012 | |
| WO | 2013040428 A1 | 3/2013 | |

OTHER PUBLICATIONS

A. Zini et al., "Influence of Semen Processing Technique on Human Sperm DNA Integrity", Urology 2000, 56, pp. 1081-1084.

A. Zini et al., "Are Tests of Sperm DNA Damage Clinically Useful? Pros and Cons" Journal of Andrology, vol. 30, No. 3, May/Jun. 2009, pp. 219-229.

A. Zini et al., "Correlations between two markers of sperm DNA integrity, DNA denaturation and DNA fragmentation, in fertile and infertile men", Fertility and Sterility, vol. 75, No. 4, Apr. 2001, pp. 674-677.

A. Zini et al., "Potential adverse effect of semen processing on human sperm deoxyribonucleic acid integrity", Fertility and Sterility, vol. 72, No. 3, Sep. 1999, pp. 496-499.

Ainsworth C., "The secret life of sperm" Nature, vol. 436, Aug. 11, 2005, pp. 770-771.

Aitken, R.J. et al., "Biological and clinical significance of DNA damage in the male germ line" J. Androl. 32, pp. 46-56 (2009).

B. Balaban et al., "Clinical outcome of intracytoplasmic injection of spermatozoa morphologically selected under high magnification: a prospective randomized study", Reprod. BioMed. Online 2011, 22, pp. 472-476.

B. S. Cho et al., "Passively Driven Integrated Microfluidic System for Separation of Motile Sperm", Analytical Chemistry, vol. 75, No. 7, Apr. 1, 2003, pp. 1671-1675.

Balakrishnan TR, et al. (1993). "Infertility among Canadians: an analysis of data from the Canadian Fertility Survey (1984) and General Social Survey (1990)" In: The Prevalence of Infertility in Canada: Research Studies of the Royal Commission on New Reproductive Technologies. Ottawa: Minister of Supply and Services Canada, pp. 107-162.

Boivin J. et al., "International estimates of infertility prevalence and treatment-seeking: potential need and demand for infertility medical care" Hum Reprod vol. 22, No. 6, pp. 1506-1512, 2007.

Boivin J. et al., (2009). "Reply: International estimates on infertility prevalence and treatment seeking: potential need and demand for medical care" Hum Reprod 24: pp. 2380-2383.

Zini. A. et al., "Sperm DNA damage is associated with an increased risk of pregnancy loss after IVF and ICSI: systematic review and meta-analysis" Hum Reprod. vol. 23, No. 12, pp. 2663-2668 (2008).

Burger HG et al., "The treatment of infertility" Ann Rev Med. 1987. 38: pp. 29-40.

Bushnik T. et al., "Estimating the prevalence of infertility in Canada" Human Reproduction, vol. 27, No. 3, pp. 738-746, 2012.

C. Ainsworth et al., "Development of a novel electrophoretic system for the isolation of human spermatozoa", Human Reproduction, vol. 20, No. 8, pp. 2261-2270, 2005.

C. Coughlan et al., "In-vitro fertilisation" Obstetrics, Gynaecology and Reproductive Medicine, 18:11, pp. 300-306, 2008.

Collins J. A., "An international survey of the health economics of IVF and ICSI" Human Reproduction Update, vol. 8, No. 3, pp. 265-277, 2002.

Cooper T.G., et al., "World Health Organization reference values for human semen characteristics" Human Reproduction Update, vol. 16, No. 3, pp. 231-245, 2010.

D. Le Lannou et al., "Nuclear maturity and morphology of human spermatozoa selected by Percoll density gradient centrifugation or swim-up procedure", J. Reprod. Fertil. 1988, 84, pp. 551-556.

D. P. Evenson, Sperm Chromatin Structure Assay (SCSA) in Spermatogenesis: Methods and Protocols (Eds.: D.T. Carrell, K.I. Aston), Humana Press, New York, 2013, pp. 147-164.

D. P. Evenson et al., "Sperm Chromatin Structure Assay: Its Clinical Use for Detecting Sperm DNA Fragmentation in Male Infertility and Comparisons With Other Techniques" J. Androl. 2002, vol. 23, No. 1, pp. 25-43.

D. Sakkas, "Novel technologies for selecting the best sperm for in vitro fertilization and intracytoplasmic sperm injection", Fertil. Steril. 2013, vol. 99, No. 4, pp. 1023-1029.

D. Sakkas et al., "The use of two density gradient centrifugation techniques and the swim-up method to separate spermatozoa with chromatin and nuclear DNA anomalies", Hum. Reprod. 2000, vol. 15, No. 5, pp. 1112-1116.

D. Seo et al., "Development of sorting, aligning, and orienting mobile sperm using microfluidic device operated by hydrostatic pressure", Microfluid. Nanofluid. 2007, 3, pp. 561-570.

E. De Lamirande et al., "Human Sperm Chromatin Undergoes Physiological Remodeling During In Vitro Capacitation and Acrosome Reaction" J. Androl. vol. 33, No. 5, pp. 1025-1035, 2012.

DiLuzio, W.R. et al. "*Escherichia coli* swim on the right-hand side" Nature, vol. 435, pp. 1271-1274 (2005).

Dulberg CS, Stephens T (1993). "The prevalence of infertility in Canada, 1991-1992: analysis of three national surveys" In: The Prevalence of Infertility in Canada: Research Studies of the Royal Commission on New Reproductive Technologies. Ottawa: Minister of Supply and Services Canada, pp. 61-106.

E. A. Gaffney et al., "Mammalian Sperm Motility", Annu. Rev. Fluid Mech. 2011, 43, pp. 501-528.

E. V. A. Åkerlöf et al., "Comparison between a swim-up and a Percoll gradient technique for the separation of human spermatozoa", Int. J. Androl. 1987,10, pp. 663-669.

F. L. Ng et al., "Comparison of Percoll, mini-Percoll and swim-up methods for sperm preparation from abnormal semen samples", Hum. Reproduction, vol. 7, No. 2, pp. 261-266, 1992.

G. Huszar et al., "Fertility testing and ICSI sperm selection by hyaluronic acid binding: clinical and genetic aspects" Reprod. BioMed. Online, vol. 14, No. 5, 2007, pp. 650-663.

G. M. Whitesides, "The origins and the future of microfluidics", Nature 2006, vol. 442, pp. 368-373.

G. Palermo et al., "Pregnancies after intracytoplasmic injection of single spermatozoon into an oocyte", Lancet 1992, 340, 17-18.

Han, C., et al. (2010). "Integration of single oocyte trapping, in vitro fertilization and embryo culture in a microwell-structured microfluidic device" Lab on a Chip, 10(21): 2848-2854.

J. C. Kirkman-Brown et al., "Sperm motility: is viscosity fundamental to progress?" Mol. Hum. Reprod. 2011, vol. 17, No. 8, pp. 539-544.

J. Erenpreiss et al., "Sperm chromatin structure and male fertility: biological and clinical aspects" Asian J. Androl. 2006, 8 (1), pp. 11-29.

K. C. Worriow et al., "Use of hyaluronan in the selection of sperm for intracytoplasmic sperm injection (ICSI): significant improvement in clinical outcomes—multicenter, double-blinded and randomized controlled trial", Hum. Reprod. 2013, vol. 28, No. 2, pp. 306-314.

K. Haubert et al., "PDMS bonding by means of a portable, low-cost corona system", Lab Chip, 2006, 6, pp. 1548-1549.

Kantsler, V. et al., "Ciliary contact interactions dominate surface scattering of swimming eukaryotes" PNAS, vol. 110, No. 4, pp. 1187-1192 (2013).

Katz, D.F. et al., "Geotaxis by Motile Spermatozoa: Hydrodynamic Reorientation" J. theor. Biol. 67, pp. 723-732 (1977).

Kricka, L.J. et al, "Applications of a Microfabricated Device for Evaluating Sperm Function" Clin Chem. 39/9, pp. 1944-1947 (1993).

L. Mazutis et al., "Single-cell analysis and sorting using droplet-based microfluidics" Nat. Protoc. 2013, vol. 8, No. 5, pp. 870-891.

L. Parmegiani et al., "Efficiency of hyaluronic acid (HA) sperm selection" J. Assist. Reprod. Genet. 2010, 27, pp. 13-16.

L. Xie et al., "Integration of Sperm Motility and Chemotaxis Screening with a Microchannel-Based Device", Clin. Chem. 2010, 56:8, pp. 1270-1278.

(56) References Cited

OTHER PUBLICATIONS

L. Y. Yeo et al., "Microfluidic Devices for Bioapplications" Small 2011, 7, No. 1, pp. 12-48.
M. A. Unger et al., "Monolithic Microfabricated Valves and Pumps by Multilayer Soft Lithography", Science, 2000, 288, pp. 113-116.
M. Antinori et al., "Intracytoplasmic morphologically selected sperm injection: a prospective randomized trial" Reprod. BioMed. Online 2008, vol. 16, No. 6, pp. 835-841.
M. Bungum et al., "Sperm chromatin structure assay (SCSA): a tool in diagnosis and treatment of infertility", Asian J. Androl. 2011, 13, pp. 69-75.
M. Enciso et al., "The ability of sperm selection techniques to remove single- or double-strand DNA damage", Asian J. Androl. 2011, 13, pp. 764-768.
Makler, A. et al., "Investigation in real time of the effect of gravitation on human spermatozoa and their tendency to swim-up and swim-down" Int J Androl. 16, pp. 251-257 (1993).
Mortimer, D. (2000). "Sperm Preparation Methods" J Androl. 21, pp. 357-366.
Niederberger C (2004). "Do not let technician biases fool you: Frozen sperm from any azoospermic man is as good as fresh for ICSI and easier for the couple" Urology 64(6): pp. 1072-1074.
Norris S (2001). "Reproductive Infertility: Prevalence, Causes, Trends, and Treatments" Parliamentary Research Branch, Library of Parliament.
Zini, A. et al., "Prevalence of abnormal sperm DNA denaturation in fertile and infertile men" Urology. 60, pp. 1069-1072 (2002).
OVO Consulting (2009). In-vitro fertilization in Canada: Cost structure analysis. Prepared for Canadian Fertility and Andrology Society.
P. Denissenko et al., "Human spermatozoa migration in microchannels reveals boundary-following navigation" Proc. Natl. Acad. Sci. U. S. A. 2012, vol. 109, No. 21, pp. 8007-8010.
P. Galajda et al., "A Wall of Funnels Concentrates Swimming Bacteria" J. Bacteriol. 2007, 189(23), pp. 8704-8707.
Pierson R. et al., (2011). "Human Assisted Reproduction 2011 Live Birth Rates for Canada" Canadian Fertility and Andrology Society, Press Release.
R. E. Jackson et al., "Effects of semen storage and separation techniques on sperm DNA fragmentation" Fertil. Steril. 2010, vol. 94, No. 7, pp. 2626-2630.
R. J. Aitken et al., "Electrophoretic sperm isolation: optimization of electrophoresis conditions and impact on oxidative stress" Hum. Reprod. 2011, vol. 26, No. 8, pp. 1955-1964.
R. J. Aitken et al., "Significance of Reactive Oxygen Species and Antioxidants in Defining the Efficacy of Sperm Preparation Techniques" J. Androl. 1988, vol. 9, No. 6, pp. 367-376.
R. M. Schultz et al., "The Science of Art" Science 2002, 296, pp. 2188-2190.
R. Matsuura et al., "Preparation and incubation conditions affect the DNA integrity of ejaculated human spermatozoa" Asian J. Androl. 2010, 12, pp. 753-759.
Raya, A. et al., "Left-right asymmetry in the vertebrate embryo: from early information to higher-level integration" Nat Rev Genet. vol. 7, pp. 283-293 (2006).
Roberts, A.M. "Gravitational Separation of X and Y Spermatozoa" Nature 238, pp. 223-225 (1972).
Rothschild, L. "Non-random Distribution of Bull Spermatozoa in a Drop of Sperm Suspension" Nature 198, pp. 1221-1222 (1963).
S. D. Fleming et al., "Prospective controlled trial of an electrophoretic method of sperm preparation for assisted reproduction: comparison with density gradient centrifugation" Hum. Reprod. 2008, vol. 23, No. 12, pp. 2646-2651.
S. S. Suarez et al., "Sperm transport in the female reproductive tract" Hum. Reprod. Update vol. 12, No. 1, 2006, pp. 23-37.
S. Tasoglu et al., "Exhaustion of Racing Sperm in Nature-Mimicking Microfluidic Channels During Sorting" Small 2013, 9, No. 20, pp. 3374-3384.
Suh, R. et al., "Microfluidic Applications for Andrology" J Androl. vol. 26, No. 6, pp. 664-670 (2005).
T. G. Schuster et al., "Isolation of motile spermatozoa from semen samples using microfluidics" Reprod. BioMed. Online 2003, 7, pp. 75-81.
T. M. Said et al., "Effects of advanced selection methods on sperm quality and ART outcome: a systematic review" Hum. Reprod. Update 2011, vol. 17, No. 6, pp. 719-733.
Tomlinson, M.J. et al., "The Diagnostic and Prognostic Value of Traditional Semen Parameters" J Androl. vol. 20, No. 5, pp. 588-593 (1999).
Winet, H. et al., "Observations on the response of human spermatozoa to gravity, boundaries and fluid shear" J. Reprod. Fert. 70, pp. 511-523 (1984).
Wolf DP et al., (1984). "Sperm Concentration and the Fertilization of Human Eggs In Vitro" Biology of Reproduction 31: pp. 837-848.
World Health Organization (2010). "WHO laboratory manual for the Examination and processing of human semen", 5th Edition.
X. Mu et al., "Microfluidics for Manipulating Cells" Small 2013, 9, pp. 9-21.
X. Zhang et al., "Lensless imaging for simultaneous microfluidic sperm monitoring and sorting" Lab Chip 2011, 11, pp. 2535-2540.
Y-J. Ko et al., "Separation of Progressive Motile Sperm from Mouse Semen Using On-chip Chemotaxis" Anal. Sci. 2012, 28, pp. 27-32.
Yuzpe A et al., (2002). "Human Assisted Reproduction live birth rates for Canada 2002" Canadian Fertility and Andrology Society, Press Release.
R. Nosrati et al., "Viable Sperm Separation on-a-Chip with Milliliter-Scale Sample Capacity" Advances in Microfluidics & Nanofluidics, May 24-26, 2013, University of Notre Dame, Indiana.
L. Earner, "Microfluidic separation of sperm based on total progressive motility in high viscosity media" MIE (Mechanical & Industrial Engineering) Research Symposium, Jun. 10, 2013, University of Toronto, Canada.

\* cited by examiner

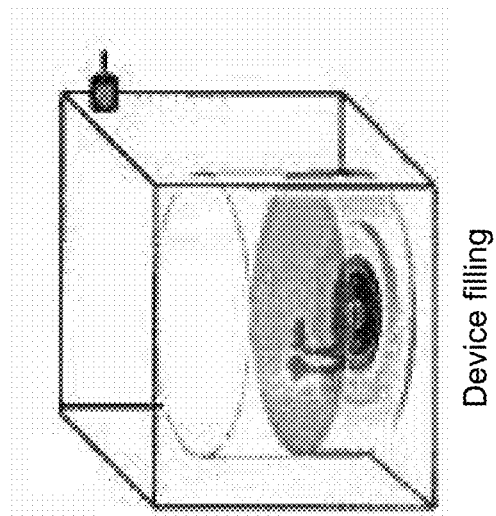
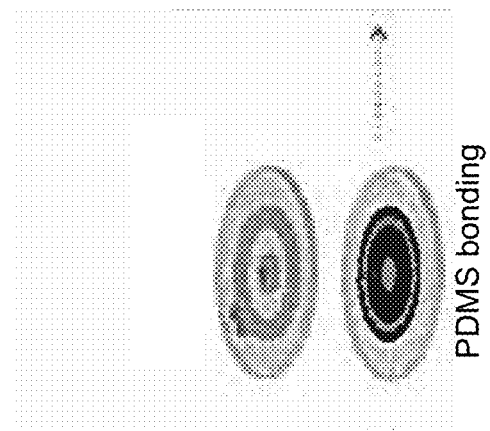
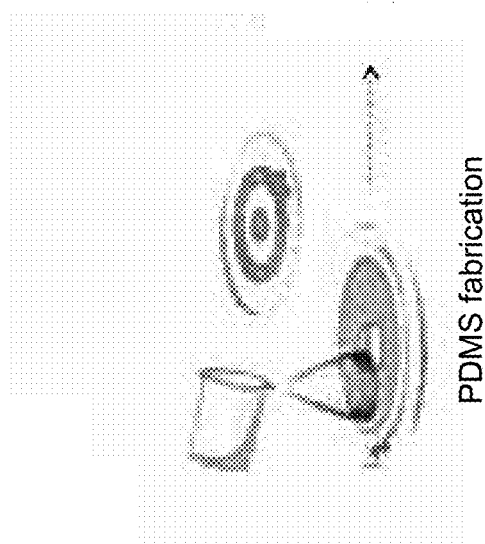
FIG. 6A PDMS fabrication
FIG. 6B PDMS bonding
FIG. 6C Device filling

APPARATUS AND METHODS FOR SPERM SEPARATION

CROSS REFERENCE TO RELATED APPLICATIONS

This application claims the benefit of U.S. Provisional Patent Application No. 61/906,231, filed Nov. 19, 2013, the entire contents of which are hereby incorporated by reference.

FIELD

The described embodiments relate to apparatus and methods for separating sperm, and more particularly to apparatus and methods for at least one of high-throughput sperm separation, and sperm separation based on wall-swimming behaviour.

BACKGROUND

Infertility has been a growing condition over the past decades (Bushnik et al., 2012). Studies revealed that 5.4% and 8.5% of Canadian couples experienced fertility issues in 1984 and 1992, respectively (Balakrishnan and Fernando, 1993; Dulberg and Stephens, 1993). In 2009-2010 the percentage of couples affected by infertility increased to 11-15%, which is similar to the prevalence of infertility in other industrialized countries (Bushnik et al., 2012; Boivin et al., 2007; Boivin et al., 2009). Since in vivo treatment of infertility is rarely possible, most infertile couples have to rely on Assisted Reproductive Technologies (ARTs) (Burger and Baker, 1987). Corresponding to the growth in infertility, numbers of In Vitro Fertilization (IVF) treatments in Canada increased from ~25,000 IVF cycles with a live birth rate of 20% (=5,000 births), to ~35,000 IVF cycles with a live birth rate of 30% (=10,500 births) in the last decade (Yuzpe et al., 2002; Pierson et al., 2011). For each cycle of IVF a couple can expect costs on average of $5,660, limiting Canadian infertility services to middle and high income households (OVO Consulting, 2009).

Sperm selection is required for ART, and the selection may influence both the treatment success rate and offspring health (Schultz and Williams, 2002; Said and Land, 2011). In IVF, an oocyte is incubated with an aliquot of 50,000 sperm from an initial sample with on the order of 100 million sperm (Coughlan and Ledger, 2008). In Intra-Cytoplasmic Sperm Injection (ICSI) a single sperm is selected and directly injected into an oocyte (Palermo et al., 1992).

In Canada alone, IVF treatments have been estimated to involve total costs of $437 million in 2002. This constitutes ~0.42% of the amount spent on health in Canada in that year (Collins, 2002).

SUMMARY

The following introduction is provided to introduce the reader to the more detailed discussion to follow. The introduction is not intended to limit or define any claimed or as yet unclaimed subject matter. One or more embodiments may reside in any combination or sub-combination of the elements or process steps described in any part of this document including its claims and figures that may serve the basis for claimed subject matter.

In one broad aspect, in at least one embodiment described herein, there is provided an apparatus for separating sperm, the apparatus comprising: an inlet reservoir for receiving a sample of semen; an outlet reservoir for collecting sperm separated from the sample; and a radial array of microchannels disposed between the inlet reservoir and the outlet reservoir to provide fluid communication therebetween, the radial array of microchannels being configured to direct motile sperm inwardly from the inlet reservoir to the outlet reservoir.

In some embodiments, the radial array of microchannels comprises a plurality of microchannel paths between the inlet reservoir and the outlet reservoir, each microchannel path comprising a path outlet adjacent the outlet reservoir, and at least one path inlet adjacent the inlet reservoir.

In some embodiments, a width of each microchannel path is between 50 µm and 300 µm, and wherein a height of each microchannel path is between 25 µm and 100 µm.

In some embodiments, the width of each microchannel path is between 100 µm and 200 µm, and wherein the height of each microchannel path is between 50 µm and 75 µm.

In some embodiments, a length of each microchannel path is between 6 mm and 9 mm.

In some embodiments, the plurality of microchannel paths comprises at least 200 microchannel paths between the inlet reservoir and the outlet reservoir.

In some embodiments, the at least one path inlet for each microchannel path comprises two path inlets separated by a dividing wall member.

In some embodiments, the apparatus further comprises a plurality of anti-return members located within the outlet reservoir and configured to restrict motile sperm from re-entering the radial array of microchannels after exiting the radial array of microchannels.

In some embodiments, there are a plurality of radial arrays each having a plurality of microchannels that are coupled to the inlet reservoir and the outlet reservoir and the radial arrays are stacked to increase the number of microchannel paths between the inlet reservoir and the outlet reservoir.

In some embodiments, there may be between 2 to 16 stacked radial arrays. In some other embodiments, there may be more than 16 stacked radial arrays. For example, if each layer of radial array is fabricated thin enough, then more radial array layers may be stacked on top of one another.

In some embodiments, the apparatus may further comprise semicircular guides disposed along an inlet wall extending from both sides of the inlet channel to redirect sperm away from the inlet wall.

In some embodiments, the semicircular guides may have radii less than about 150 µm.

In some embodiments, the apparatus may further comprise at least one additional radial array of microchannels layered on top of another radial array of microchannels.

In another broad aspect, in at least one embodiment described herein, there is provided an apparatus for separating sperm, the apparatus comprising: an inlet reservoir for receiving a sample of semen; an outlet reservoir for collecting sperm separated from the sample; and at least one microchannel path disposed between the inlet reservoir and the outlet reservoir to provide fluid communication therebetween, the at least one microchannel path comprising a path inlet adjacent the inlet reservoir, a path outlet adjacent the outlet reservoir, and a junction located between the path inlet and the path outlet for directing a portion of motile sperm that enter the path inlet towards the outlet reservoir based on wall-swimming behaviour of sperm.

In some embodiments, a width of the at least one microchannel path is between 50 µm and 300 µm, and wherein a height of the at least one microchannel path is between 25 µm and 100 µm.

In some embodiments, the width of the at least one microchannel path is between 100 μm and 200 μm, and wherein the height of the at least one microchannel path is between 50 μm and 75 μm.

In some embodiments, a length of the at least one microchannel path is between 6 mm and 9 mm.

In some embodiments, the junction comprises a left path and a right path for a motile sperm swimming through the at least one microchannel path from the path inlet and towards the outlet reservoir.

In some embodiments, the junction further comprises a central path disposed between the left path and the right path.

In some embodiments, the left path leads to the path outlet, and the right path leads to a collection chamber.

In some embodiments, the right path leads to the path outlet, and the left path leads to a collection chamber.

In some embodiments, a side channel angle between a side wall of the at least one microchannel path located between the path inlet and the junction and a mutual side wall of either the left path or the right path is less than about 105°.

In some embodiments, the side channel angle is about 45°.

In some embodiments, both the left path and the right path lead to the path outlet, and the central path leads to a collection chamber.

In some embodiments, the left path leads to the path outlet, and the central path and the right path each lead to a collection chamber.

In some embodiments, the right path leads to the path outlet, and the central path and the left path each lead to a collection chamber.

In some embodiments, the central path leads to the path outlet, and the left path and the right path each lead to a collection chamber.

In some embodiments, the apparatus comprises a radial array of microchannel paths disposed between the inlet reservoir and the outlet reservoir, the radial array of microchannel paths comprising the at least one microchannel path.

In some embodiments, there are a plurality of radial arrays each having a plurality of microchannels that are coupled to the inlet reservoir and the outlet reservoir and the radial arrays are stacked to increase the number of microchannel paths between the inlet reservoir and the outlet reservoir.

In some embodiments, there may be between 2 to 16 stacked radial arrays. In some other embodiments, there may be more than 16 stacked radial arrays. For example, if each layer of radial array is fabricated thin enough, then more radial array layers may be stacked on top of one another.

In some embodiments, the apparatus may further comprise semicircular guides disposed along an inlet wall extending from both sides of the inlet channel to redirect sperm away from the inlet wall.

In some embodiments, the semicircular guides may have radii less than about 150 μm.

In some embodiments, the apparatus further comprises at least one anti-return member located within the outlet reservoir and configured to restrict motile sperm from re-entering the at least one microchannel path after exiting the path outlet.

In some embodiments, the inlet reservoir is dimensioned to receive about 1 mL of semen.

In some embodiments, the apparatus is fabricated from at least one of Polydimethylsiloxane (PDMS), polycarbonate, polystyrene and glass.

In another broad aspect, in at least one embodiment described herein, there is provided a method for separating sperm, the method comprising: providing an apparatus comprising: an inlet reservoir for receiving a sample of semen; an outlet reservoir for collecting sperm separated from the sample; and a radial array of microchannels disposed between the inlet reservoir and the outlet reservoir to provide fluid communication therebetween, the radial array of microchannels being configured to direct motile sperm inwardly from the inlet reservoir to the outlet reservoir; filling the inlet reservoir, the outlet reservoir, and the radial array of microchannels with a buffer fluid; introducing a sample of semen into the inlet reservoir; and retrieving the sperm separated from the sample from the outlet reservoir.

In some embodiments, the method further comprises covering the outlet reservoir with an outlet closure member prior to the introducing act, and uncovering the outlet reservoir prior to the retrieving act.

In some embodiments, the outlet closure member comprises a layer of an adhesive tape.

In some embodiments, syringe ports are used as the inlet and outlet closures members.

In some embodiments, the method further comprises covering the inlet reservoir with an inlet closure member after the introducing act.

In some embodiments, the retrieving act is performed between about 10 and 60 minutes after the introducing act.

In some embodiments, the retrieving act is performed between about 12 and 17 minutes after the introducing act.

In some embodiments, the buffer fluid comprises a HEPES-buffered saline buffer comprising about 1% polyvinyl alcohol and about 0.5% methyl cellulose.

In some embodiments, the buffer fluid comprises a low or high viscosity buffer.

In some embodiments, the filling act comprises submerging the apparatus in a vessel containing buffer fluid, and applying a vacuum to remove air bubbles from the radial array of microchannels.

In some embodiments, the method further comprises, before the introducing act, equilibrating a temperature of the buffer-filled apparatus to about 37° C., and maintaining the temperature of the buffer-filled apparatus at about 37° C. until the retrieving act.

In some embodiments, the apparatus may further comprise at least one additional radial array of microchannel paths layered on top of an adjacent array of microchannel paths.

In another broad aspect, in at least one embodiment described herein, there is provided a method for separating sperm, the method comprising: providing an apparatus comprising: an inlet reservoir for receiving a sample of semen; an outlet reservoir for collecting sperm separated from the sample; and at least one microchannel path disposed between the inlet reservoir and the outlet reservoir to provide fluid communication therebetween, the at least one microchannel path comprising a path inlet adjacent the inlet reservoir, a path outlet adjacent the outlet reservoir, and a junction located between the path inlet and the path outlet for directing a portion of sperm that enter the path inlet towards the outlet reservoir based on wall-swimming behaviour of sperm; filling the inlet reservoir, the outlet reservoir, and the at least one microchannel path with a buffer fluid; introducing a sample of semen into the inlet reservoir; and retrieving the sperm separated from the sample from the outlet reservoir.

In some embodiments, the method further comprises covering the outlet reservoir with an outlet closure member prior to the introducing act, and uncovering the outlet reservoir prior to the retrieving act.

In some embodiments, the outlet closure member comprises a layer of an adhesive tape.

In some embodiments, the method further comprises covering the inlet reservoir with an inlet closure member after the introducing act.

In some embodiments, the retrieving act is performed between about 10 and 60 minutes after the introducing act.

In some embodiments, the retrieving is performed between about 12 and 17 minutes after the introducing act.

In some embodiments, the buffer fluid comprises a HEPES-buffered saline buffer comprising about 1% polyvinyl alcohol and about 0.5% methyl cellulose.

In some embodiments, the buffer fluid comprises a low or high viscosity buffer.

In some embodiments, the filling act comprises submerging the apparatus in a vessel containing buffer fluid, and applying a vacuum to remove air bubbles from the at least one microchannel path.

In some embodiments, the method further comprises, before the introducing act, equilibrating a temperature of the buffer-filled apparatus to about 37° C., and maintaining the temperature of the buffer-filled apparatus at about 37° C. until the retrieving act.

It will be appreciated by a person skilled in the art that a method or apparatus described herein may embody any one or more of the features contained herein and that the features may be used in any particular combination or sub-combination.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment and the figures will now be briefly described.

FIGS. 6A-6C are schematic diagrams of fabrication, bonding, and filling the apparatus of FIG. 1 in accordance with one embodiment;

FIG. 8A is a chart of sperm concentrations and counts (inset) for experiments with samples stained prior to injection (n=5), FIG. 8B is a chart of corresponding percentage vitality of selected sperm right after sample collection (n=5), FIG. 8C is a chart of sperm concentrations and counts (shown inset) for experiments with staining after the selection process (n≥4), and FIG. 8D is a chart of corresponding percentage vitality of selected sperm 30 min (required for staining procedure) after sample collection, in comparison with initial raw semen vitality (n≥4);

FIG. 10A shows a human sperm chromatin structure assay histogram indicating the population of sperm with DNA fragmentation (% DFI) for raw semen, FIG. 10B shows a human sperm chromatin structure assay cytogram indicating the population of sperm with high DNA stainability (% HDS) for raw semen, and FIGS. 10C-D show analogous assay results for selected sperm collected from the device.

FIGS. 11A-11O are charts showing selected human sperm count and DNA integrity results with 6 mm, 7.5 mm, and 9 mm microchannel lengths (n=4). FIG. 11A is a chart of initial raw semen and selected sperm concentrations with corresponding sperm counts shown inset, FIG. 11B is a chart of percentage of DNA fragmentation index (% DFI), and FIG. 11C is a chart of percentage of high DNA stainability (% HDS);

FIG. 13A is a chart of initial raw semen and selected sperm concentration with sperm counts shown inset, FIG. 13B is a chart of percentage of DNA fragmentation index (% DFI), and FIG. 13C is a chart of percentage of high DNA stainability (% HDS);

FIG. 17A is a chart of spermatozoa concentration collected from each of the outlets for the left-swimmer (LS), straight-swimmer (SS), and right-swimmer (RS) spermatozoa as compared to the raw semen sample; FIG. 17B is a chart of percentage vitality of the spermatozoa collected from each of the outlets for the LS, SS, and RS as compared to the raw semen sample; FIG. 17C is a chart of percentage DNA Fragmentation Index (DFI) of the spermatozoa collected from the outlets as compared to the raw semen sample; and FIG. 17D is a chart of percentage of high DNA stainability (% HDS) of the spermatozoa collected from the outlets as compared to the raw semen sample;

Figure 1:
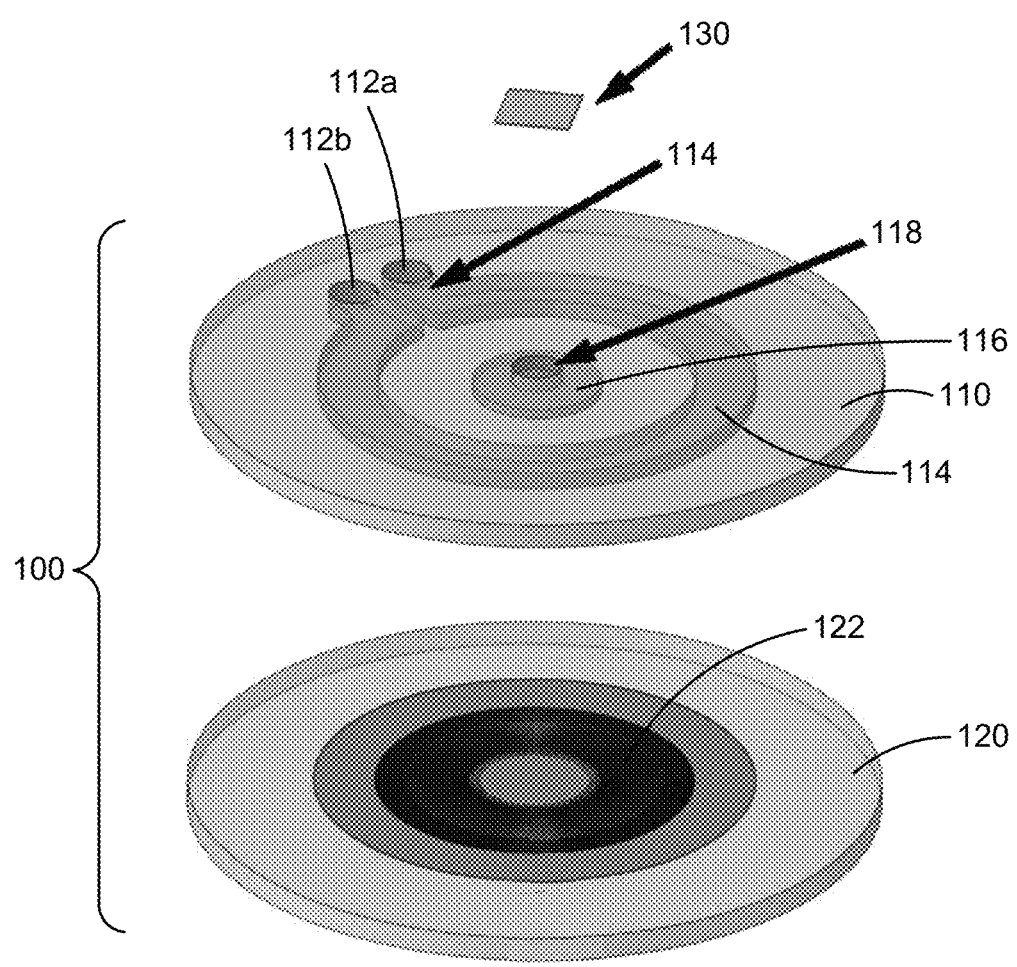
FIG. 1 is an exploded perspective view of an apparatus for separating sperm in accordance with one example embodiment.

Further aspects and features of the embodiments described herein will appear from the following description taken together with the accompanying drawings.

DESCRIPTION OF EXAMPLE EMBODIMENTS

Various apparatuses or processes will be described below to provide an example of at least one embodiment of the claimed subject matter. No embodiment described below limits any claimed subject matter and any claimed subject matter may cover processes, apparatuses, devices, or systems that differ from those described below. The claimed subject matter is not limited to apparatuses, devices, systems, or processes having all of the features of any one apparatus, device, system, or process described below or to features common to multiple or all of the apparatuses, devices, systems, or processes described below. It is possible that an apparatus, device, system, or process described below is not an embodiment of any claimed subject matter. Any subject matter that is disclosed in an apparatus, device, system, or process described below that is not claimed in this document may be the subject matter of another protective instrument, for example, a continuing patent application, and the applicants, inventors, or owners do not intend to abandon, disclaim, or dedicate to the public any such subject matter by its disclosure in this document.

The apparatus and methods described herein may be used for variety of purposes, such as (but not limited to) combinations of the following applications: sperm selection, semen purification, high viability selection, high concentration selection, high DNA integrity selection, high maturity selection, or improvement in selected population of motile cells in terms of: viability, concentration, DNA integrity, and/or maturity. The apparatus and methods may be used for clinical or home-based semen purification for application in in vitro fertilization (IVF) and intrauterine insemination (IUD.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term if this deviation would not negate the meaning of the term it modifies.

Additionally, it should be noted that the term sperm separation used herein may be defined as (but not limited to) any of these terms: selection, purification, rapid selection, and high throughput selection of motile cells.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made if the end result is not significantly changed.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As noted above, male infertility is growing worldwide (Bushnik et al., 2012; Boivin et al., 2007), yet Assisted Reproductive Technologies (ARTs) are only successful in 30% of the cases (Pierson et al., 2011). Since 40-50% of fertility issues are due to male infertility, selection of the most fertile sperm is absolutely crucial for the success rates of ARTs (Norris, 2001).

Sperm selection is an important part of ART, and may influence both success rates and offspring health. The importance of sperm and separation approaches has been underestimated and previous research mostly has been focused on egg retrieval and cultivation. Recent findings indicate a much larger role for sperm than just delivering a second set of chromosomes (Ainsworth, 2005). Unfortunately, current semen processing and sperm selection techniques, like centrifugation and swim-up, have hardly changed since 1978 (Han et al., 2010). One concern is that the current separation techniques differ greatly from the in vivo process and may even cause damage to sperm (Han et al., 2010; Mortimer, 2000). Further, known selection techniques often depend on technician experience in selecting sperm, which makes the process prone to errors (Suh et al., 2005; Niederberger, 2004).

Improvements of semen processing and sperm separation are needed. Apparatus and methods described herein may be implemented in fertility clinics, but may also be applied in fertility research laboratories, e.g. to investigate causes and treatments of male infertility, or for home-based semen purification for application in IVF and intrauterine insemination (IUD. Apparatus and methods described herein may be used to separate sperm for IVF, ICSI, IUI, and/or other ARTs. Apparatus and methods described herein may also be used for non-human applications, e.g. selecting bovine (or other animal) sperm for IVF or other breeding methods.

The semen processing and sperm separation performed by the various embodiments of apparatuses and methods described herein may be used for variety of purposes, such as (but not limited to) combinations of two or more of the following applications: sperm selection, semen purification, high viability selection, high concentration selection, high DNA integrity selection, high maturity selection, or improvement in selected population of motile cells in term of: viability, concentration, DNA integrity, and/or maturity.

One challenge of sperm selection is dictated by the biology: sample volume, sperm concentration and lifetimes in vitro. Given order of magnitude values for sample volume (typically ~1 mL), sperm concentration (typically ~100M/mL), and allowable time for a selection process (typically 10-20 min), the fundamental sorting rate dictated by the biology may be estimated as ~100 kHz, which is significantly higher than available cell sorting technologies (Mazutis et al., 2013; Aharoni et al., 2006).

For example, looking at typical numbers: from approximately 196,000,000 sperm in an average male sample, 25,000 to 50,000 sperm are typically required for droplet base IVF, where egg cells are surrounded by a specific number of sperm cells that possibly fertilize the egg (Cooper et al., 2010; Wolf et al., 1984). For ICSI, a single sperm is selected for injection into the oocyte. For human IUI, ~5-50×10$^6$ sperm are typically used. For bovine IVF, typically about 50,000 sperm are used.

In some current techniques, due to time limitations, no actual sperm separation, but rather only a sperm purification process is performed. The sperm purification process typically only cleans the seminal fluid away from the sperm (World Health Organization, 2010). This means that current sperm preparation methods may not sort the most fertile sperm from a sample.

Two common current techniques applied for sperm selection in preparation for ART are density gradient centrifugation (Le Lannou and Blanchard, 1988) and the swim-up assay (Sakkas et al., 2000; Åkerlöf et al., 1987), based on sedimentation and migration, respectively. In terms of sperm numbers and time, density gradient centrifugation typically selects ~36% of sperm population from 0.5 mL of raw semen within 30 min, and the swim-up assay typically selects ~12% of the sperm population from 1 mL within 1 hour; resulting in 18-19% and 5% improvement in sperm motility respectively (WHO Press, 2010; Ng et al., 1992). The selected sperm population can be used directly for IVF or ICSI but in some clinics an additional centrifugation (10-15 min) and subsequent re-suspension of the motile sperm in a buffer solution is undertaken. In the case of ICSI, a single sperm is selected from the prepared sample by an embryologist (a process involving visual inspection of a very small fraction of sperm (e.g. ~100)).

These current sperm processing techniques may suffer from several limitations: the methods do not resemble the natural process in vivo (Sakkas, 2013); the selected sperm population is often contaminated with poorly motile sperm and somatic cells (e.g. leukocytes) (Said and Land, 2011; Sakkas, 2013); the selected sperm population may suffer iatrogenic injury (e.g. oxidative injury) due to centrifugation (Aitken and Clarkson, 1988), and prolonged or multi-step processing (Said and Land, 2011); and further manual visual inspection is often required and this embryologist-specific step may in part be responsible for success-rate variations between clinics (Sakkas, 2013).

An established metric for sperm quality is sperm DNA integrity, i.e. a measure of sperm chromatin organization/architecture, chromatin compaction and DNA strand integrity (Erenpreiss et al., 2006). High DNA integrity is linked to both improved fertilization rates and embryo development in IVF and ICSI (Ahmadi and Ng, 1999; Agarwal and Said, 2003). Both density gradient centrifugation and swim-up have been found to generally select sperm populations with increased DNA integrity (as compared to the raw sample) (Matsuura et al., 2010; Enciso et al., 2011; Jackson et al., 2010). However, density gradient centrifugation has also been shown to potentially induce sperm DNA damage (Said and Land, 2011; Sakkas, 2013; Zini et al., 1999).

Alternative approaches for sperm selection include electrophoresis (Fleming et al., 2008; Aitken et al., 2011; Zhang et al., 2011), hyaluronic acid bonding (Huszar et al., 2007; Parmegiani et al., 2010; Worrilow et al., 2013), and sperm morphological assessment under high magnification (Balaban et al., 2011; Antinori et al., 2008; Souza Setti et al., 2010), with the last two methods being only applicable for individual sperm selection. These approaches have had limited clinical application due to equipment and time requirements, negative impacts on sperm motility and/or dependence on the experience of an embryologist (Balaban et al., 2011; Antinori et al., 2008; Souza Setti et al., 2010; Ainsworth et al., 2005).

A breakthrough in sperm selection technology could greatly improve the feasibility and success rate of ARTs. However, clinical spermatozoa preparation techniques have not significantly improved in the past 20 years (Han et al., 2010). To address this lack of improvement microfluidic devices have emerged as an alternative method for spermatozoa preparation (Suh et al., 2005; Kricka et al., 1993).

Microfluidic approaches are well suited to cell manipulation (Whitesides, 2006; Yeo et al., 2011; Mu et al., 2013), and have been developed to select or manipulate sperm based on motility (Cho et al., 2003; Xie et al, 2010; Schuster et al., 2003; Seo et al., 2007; Tasoglu et al., 2013), chemotaxis (Xie et al, 2010; Ko et al., 2012), optical forces (Zhang et al., 2011; Ohta et al., 2010), and electrophoresis (Ainsworth et al., 2005). However, in most cases, the complexity of using microfluidic devices and the need for supporting infrastructures have been barriers to clinical implementation. In addition, the low sample volume characteristic of microfluidics proves to be a disadvantage in the context of sperm selection due to the inherent milliliter-scale size of human samples.

Also, although the techniques are advancing, not all fertility parameters crucial for positive outcomes are routinely tested (Tomlinson et al., 1999). DNA integrity is of particular importance as low DNA integrity can increase the rate of miscarriage (Aitken et al., 2009; Zini et al., 2008).

These biological and clinical design constraints point to an opportunity for a simple, passive (i.e. without fluid flow in the apparatus), and highly parallelized microfluidic approach to sperm selection based on sperm motility.

The various embodiments described herein generally relate to apparatuses and methods for a microfluidic sperm selection, and more particularly to sperm separation using variations of a radial device to separate sperm based on motility, and/or based on the preference of sperm to swim near channel walls. In some embodiments, the performance of such a radial device may be dependent on the microchannel network design.

High-Throughput Separation Based on Motility

In one broad aspect, the embodiments described herein generally relate to a microfluidic sperm selection apparatus for rapid throughput in comparison to other sperm-sorting, microfluidic devices. For example, some embodiments may provide single sperm selection as well as selection of up to 50,000 sperm (which may be required for specific types of ARTs) from up to 1 ml of a pure semen sample (~100,000,000 sperm), and may be characterized as providing a separation frequency of higher than 40 kHz.

Alternatively or additionally, some embodiments may provide semen processing and separation of sperm in a one-step procedure that is relatively fast (e.g. sperm selection may be performed within 1 hour after semen donation).

Alternatively or additionally, some embodiments may not use chemicals nor include steps that might be harmful to sperm (e.g. centrifugation which can cause DNA damage).

Alternatively or additionally, some embodiments may simulate the natural conditions of the female body, e.g. by using a high-viscosity, physiological buffer in a micro-network.

Alternatively or additionally, some embodiments are based on an automated scientific approach and may not depend significantly on the technician's experience, or other uncontrolled environmental factors. Due to the simplicity of some embodiments, implementation in e.g. fertility clinics may help to reduce the variance between different fertility centres.

Alternatively or additionally, some embodiments may be less expensive than current sperm separation techniques, based on, for example, the use of fewer chemicals and equipment, and/or fewer technician working hours.

As noted above, one challenge of sperm selection is dictated by biology: a heterogeneous population of ~$10^8$ sperm per milliliter with a short lifetime in vitro. However, conventional sperm selection approaches result in less than 50% improvement in DNA integrity. Here, at least one embodiment of a clinically applicable microfluidic device is presented that selects sperm based on the progressive motility in a large number (e.g. 500) of parallel microchannels. These devices, according to the teachings herein, leverage surface accumulation behaviour and boundary following navigation of sperm in micro-scale geometry. The result is a one-step procedure for semen purification and high DNA integrity sperm selection from 1 mL of raw semen in under 20 minutes. Experiments with bull sperm indicate more than 89% improvement compared to the raw semen sample in selected sperm vitality. Clinical tests with human sperm show more than 80% improvement in human DNA integrity, significantly outperforming the best current practices. These results demonstrate the presence of a sub-population of sperm with nearly intact chromatin and DNA integrity, and a simple clinically-applicable method according to the teachings herein to select this population.

The functionality of at least some of the embodiments described herein is achieved by self-propelled sperm swimming through an effectively stagnant fluid (which may be a relatively high-viscosity fluid) in a radial array of parallel channels and leverages the natural swimming characteristics of sperm in confined geometries, e.g. surface accumulation behaviour and/or boundary-following navigation. The microchannel network directs motile sperm from the injection ring radially-inward toward the outlet from where the selected sperm are extracted. Since there is no flow (or effectively no flow) in the microchannels, only motile sperm that swim through the fluid are directed to the outlet. The result is a simple, clinically applicable apparatus and/or method for semen purification and high DNA integrity sperm selection.

The selection performance of this approach has been established through, inter glia, experiments with bull semen to quantify selected sperm concentration and vitality. At least some of the embodiments described herein have also been tested with human sperm including the assessment of DNA integrity using the sperm chromatin structure assay (SCSA). It has been observed that sperm selected from the device appear to be generally quantifiably superior in terms of DNA integrity than those selected using current clinical sperm selection methods.

Reference is now made to FIGS. 1 to 3B, which illustrates an example embodiment of an apparatus 100 for separating sperm. In some embodiments, apparatus 100 may be fabricated from Polydimethylsiloxane (PDMS), and will be described as such herein. It will be appreciated that other suitable materials (e.g. Poly(methyl methacrylate) (PMMA) or other suitable thermoplastics (such as polycarbonate, polystyrene, glass, etc.) may be used.

Given its intended application, it is envisioned that apparatus 100 will typically be a single-use device, particularly when used to process human semen. However, it will be appreciated that for some applications (e.g. when used to sort animal semen, such as bovine semen), apparatus 100 may be re-used to sort multiple samples.

Apparatus 100 comprises a top layer 110 and a bottom layer 120. Top layer 110 comprises a recessed inlet portion 114 (configured to form inlet reservoir 115 when top layer 110 is bonded to bottom layer 120) and a recessed portion 116 (configured to form outlet reservoir 117 when top layer 110 is bonded to bottom layer 120) provided on the bottom surface of the top layer 110. In some embodiments, in order to generate a master to fabricate the apparatus from PDMS, the features may be cut from PMMA or another suitable material and attached to a planar surface (e.g. a petri dish).

The recessed inlet portion 114 is configured to cooperate with bottom layer 120 to form a (preferably) ring-shaped inlet reservoir 115 with entrances to the microchannels 122 within the ring. In general, this approach enables on-chip processing of more than 50M sperm introduced on-chip within 10-20 min experiments leading to a high frequency sperm selection in the order of $10^5$ Hz. It will be appreciated that other geometries (e.g. semi-circular) may be used for the inlet reservoir, in variant embodiments.

The recessed inlet portion 114 and/or bottom layer 120 may be dimensioned so that inlet reservoir 115 is dimensioned to accommodate an expected sample size, which may vary depending on the expected application of apparatus 100. For example, inlet reservoir 115 may be dimensioned to accommodate about 1 mL of raw semen (e.g. to accommodate typical human samples), about 3 mL of raw semen (e.g.

to accommodate typical bovine samples), or to accommodate larger (or smaller) semen samples.

Bottom layer 120 comprises a radial array of microchannels 122 for directing motile sperm inwardly from the inlet reservoir 115 towards the outlet reservoir 117 in a static flow situation. The inlet reservoir 115 is preferably disposed along an outer portion of the radial array of microchannels 122 and the outlet reservoir is preferably disposed along an inner portion of the radial array of microchannels 122. A master for the bottom layer 120 may be fabricated using standard soft-lithography techniques, allowing multiple bottom layers 120 to be made e.g. from PDMS using such a master.

The geometry of apparatus 100, and particularly the microchannel network 122, is preferably informed by the biological sample requirements and the geometry of the fallopian tube, e.g. to mimic an in vivo environment. For example, in some embodiments the width and height of each microchannel (e.g. 100 μm×75 μm) may generally correspond to the distance between the ciliated epithelium of the fallopian tube (Suarez and Pacey, 2006) and the average human sperm length (Gaffney et al., 2011). The sperm are thus confined by the microchannel geometry that resembles elements of the fallopian tube, triggering their natural boundary-following navigation (Denissenko et al., 2012).

Figure 4:
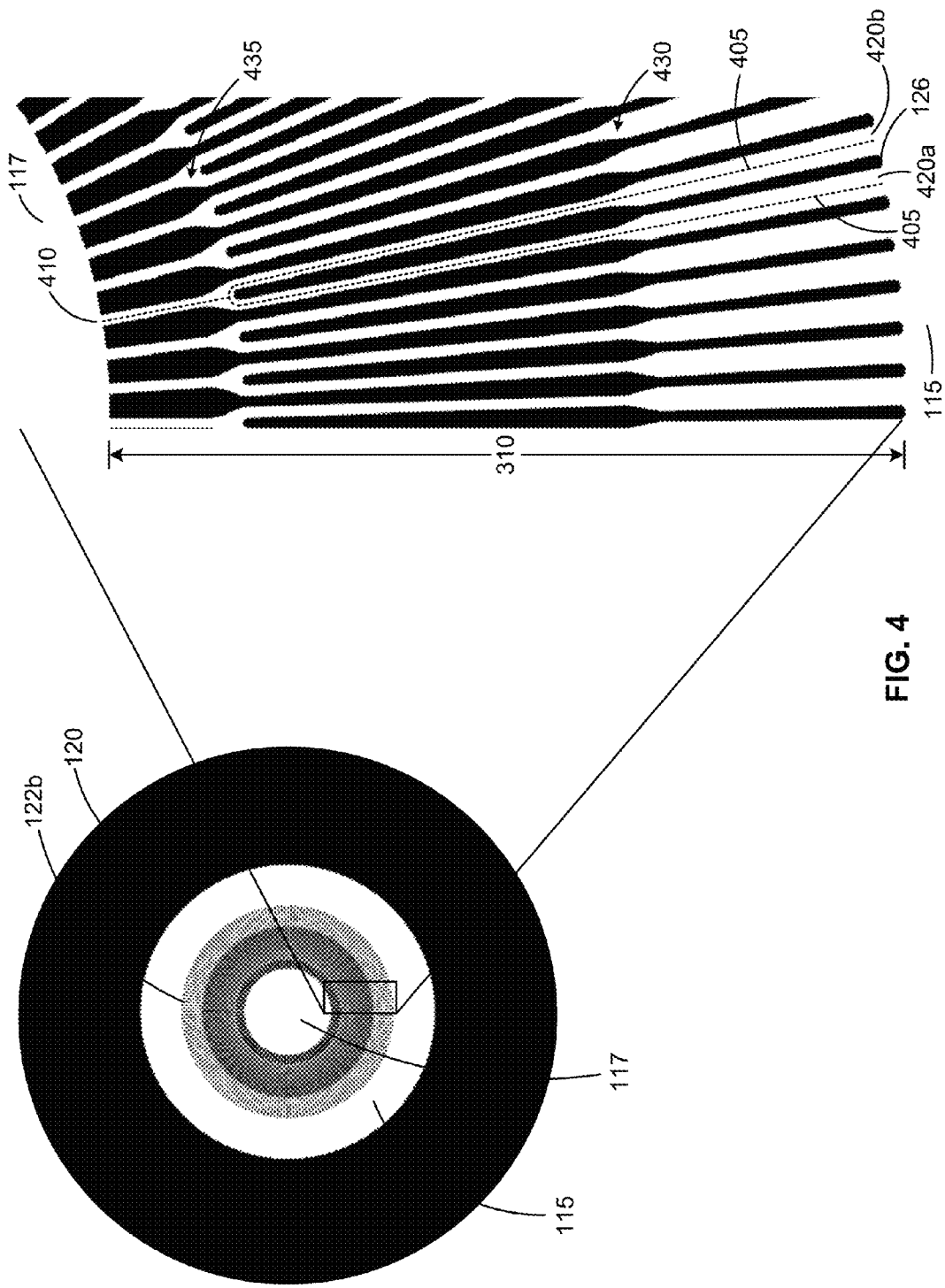
FIG. 4 is a top view, partially enlarged, of an alternate array of microchannels in accordance with another example embodiment.
Figure 5:
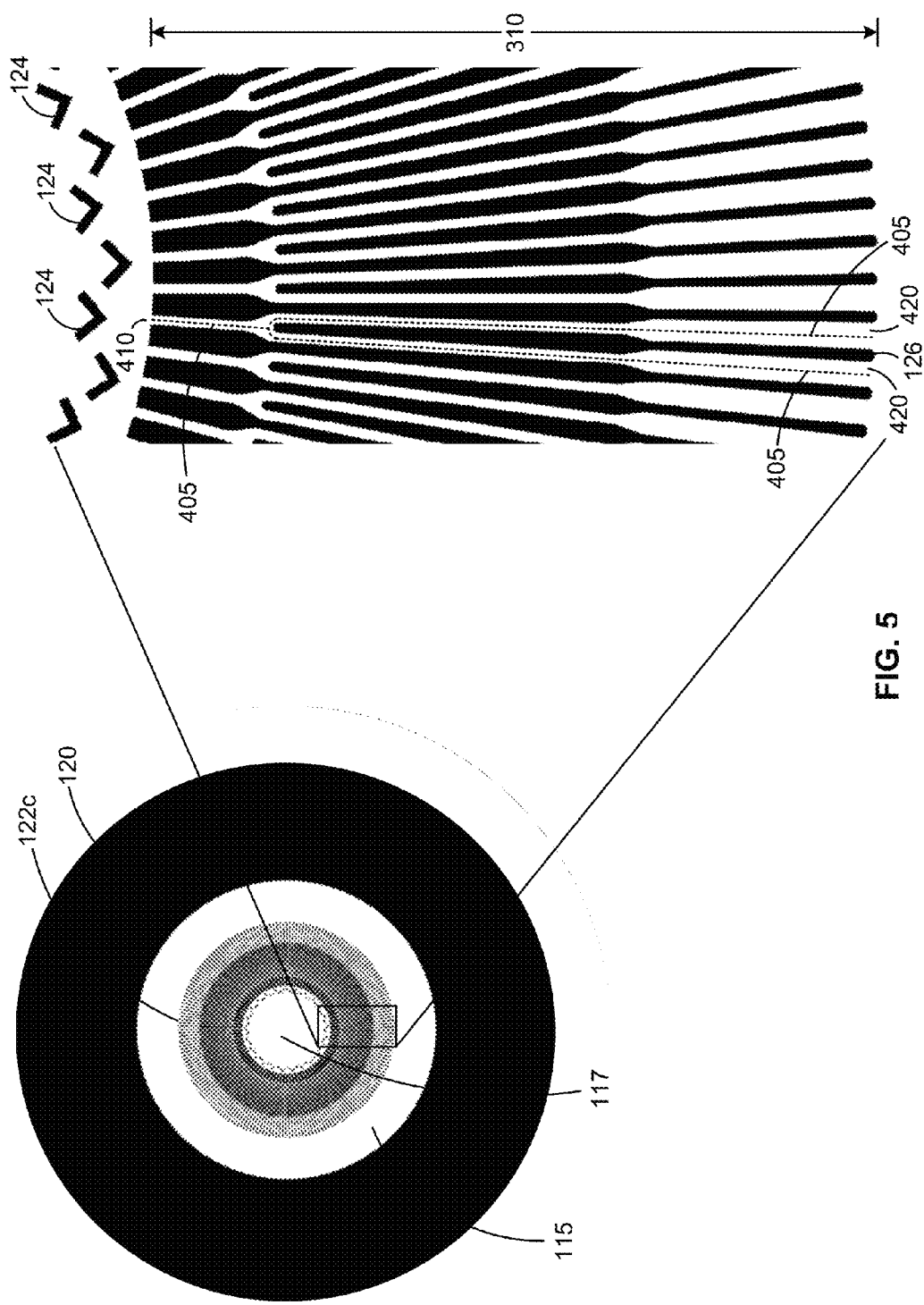
FIG. 5 is a top view, partially enlarged, of the array of microchannels of FIG. 4 with a plurality of anti-return members.

Examples of alternative arrays of microchannels are shown in FIGS. 3A-5. As shown in FIG. 4, microchannel array 122b comprises a plurality of microchannel paths 405 providing fluid communication between inlet reservoir 115 and outlet reservoir 117. Each path 405 comprises a path outlet 410 adjacent outlet reservoir 117, and at least one path inlet 420 adjacent inlet reservoir 115.

It will be appreciated that the number of microchannel paths in the microchannel array may vary. While it has been found that microchannel arrays with about 200 to about 500 microchannel paths generally provide acceptable sorting performance, depending on the expected sample volume, the dimensions of each microchannel, and/or the desired approximate number of sperm desired to be collected, more or fewer microchannels may be provide in variant embodiments.

Due to the radial nature of the array of microchannels 122, at least one divider 126 may be provided adjacent the inlet reservoir, so that two or more paths 405 that originate at separate path inlets 420 (see e.g. path inlets 420a and 420b in FIG. 4) may combine before the outlet reservoir (e.g. 5 mm before the outlet reservoir) to maintain a relatively uniform microchannel path cross-section geometry, despite the radial nature of the microchannel array 122.

In some embodiments, the walls of the microchannels may generally taper inwardly along a path 405 between a path inlet 420 and a path outlet 410. Alternatively or additionally, one or more distinct tapering regions (see e.g. regions 430 and 435 in FIG. 4) may be provided by the microchannel walls, to assist in directing motile sperm towards the outlet reservoir 117 and/or to assist in maintaining a relatively uniform microchannel width despite the radial nature of the microchannel array 122. To provide such tapering regions, the thickness of the wall members that define the microchannel paths may vary (either gradually or abruptly) along their length.

The length 310 for each microchannel path may be up to 10 mm in order to accommodate the average progressive swimming velocity of human sperm (i.e. ~45 μm/s) in a buffer fluid and a selection time limit of about 10-20 minutes. As will be discussed further below, devices were fabricated and tested with 6 mm, 7.5 mm, and 9 mm microchannel lengths, to quantify the influence of channel length on selection performance.

Figure 23:
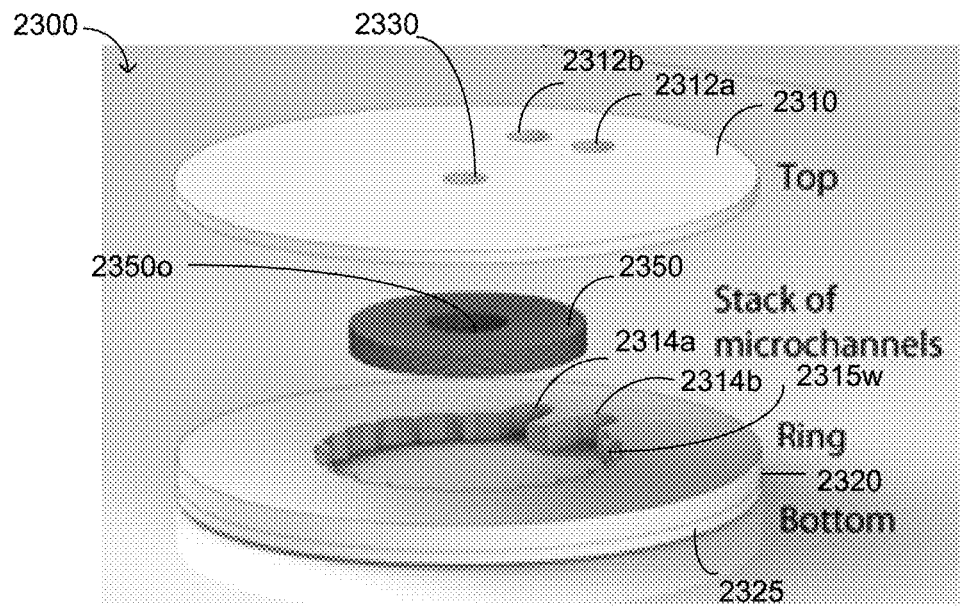
FIG. 23 is an exploded perspective view of an example of an alternative embodiment of an apparatus for separating sperm.

In some embodiments, more than 100-500 microchannels may be required. Due to restrictions on the inlet and outlet volumes it is not possible to change the number of microchannels in the layer, as such the plurality of the microchannels may be stacked a number of times, such as 2-16 times for example, in order to increase the number of microchannel paths between the inlet reservoir and the outlet reservoir. An example of this is shown in FIG. 23. In some other embodiments, there may be more than 16 stacked radial arrays. For example, if each layer of radial array is fabricated thin enough, then more radial array layers may be stacked on top of one another.

Example dimensions for the microchannel arrays shown in FIGS. 3A-5 are shown in Table 1.

TABLE 1

Dimensions of microchannels for high-throughput separation based on motility.

| Device I | Width | Height | Length | Radius |
| --- | --- | --- | --- | --- |
| Inlet | 4.5-5.5 mm | 1.45 mm | n.a. | n.a. |
| Channels | 100-200 μm | 50-75 μm | 6 mm, 7.5 mm, 9 mm | n.a. |
| Outlet | n.a. | 0.8 mm | n.a. | 5.0-6.0 mm |

Preferably, the ring geometry of the inlet reservoir 115 (e.g. as shown in FIGS. 1-5) evenly distributes an injected semen sample across the entrances of the parallel microchannels (e.g. where a 1 ml sample is injected into an apparatus 100 with ~500 microchannels in microchannel array 122, about 2 μL of semen will be adjacent each microchannel inlet).

Figure 2A:
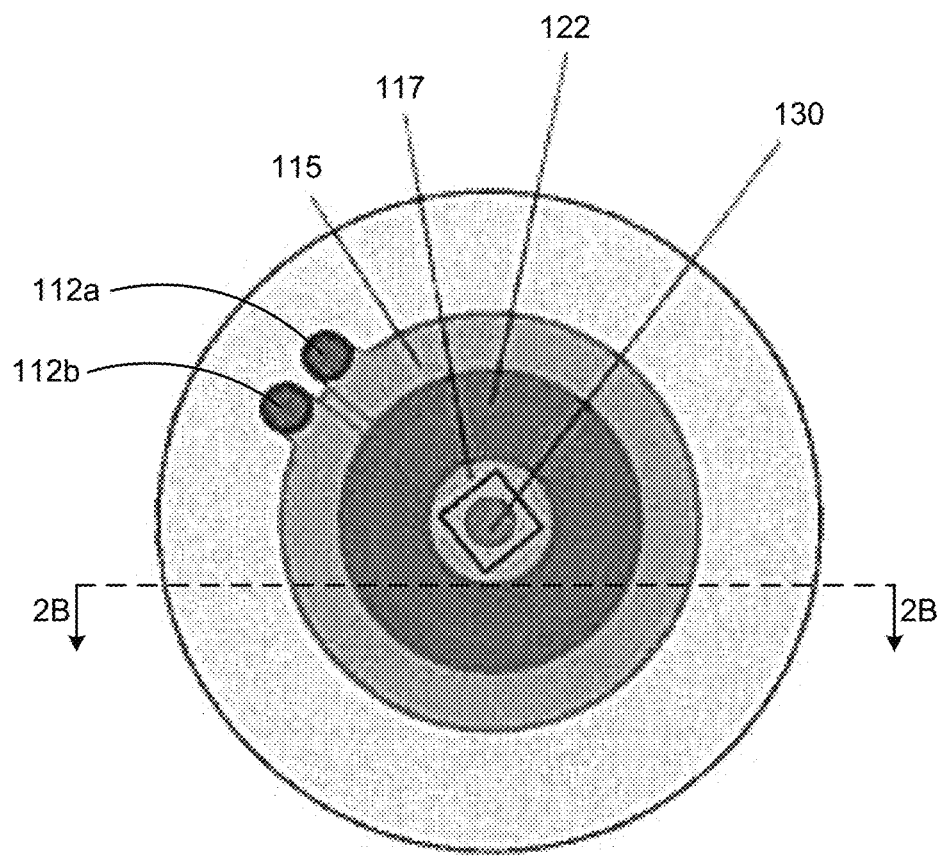
FIG. 2A is a top view of the apparatus of FIG. 1.
Figure 2B:
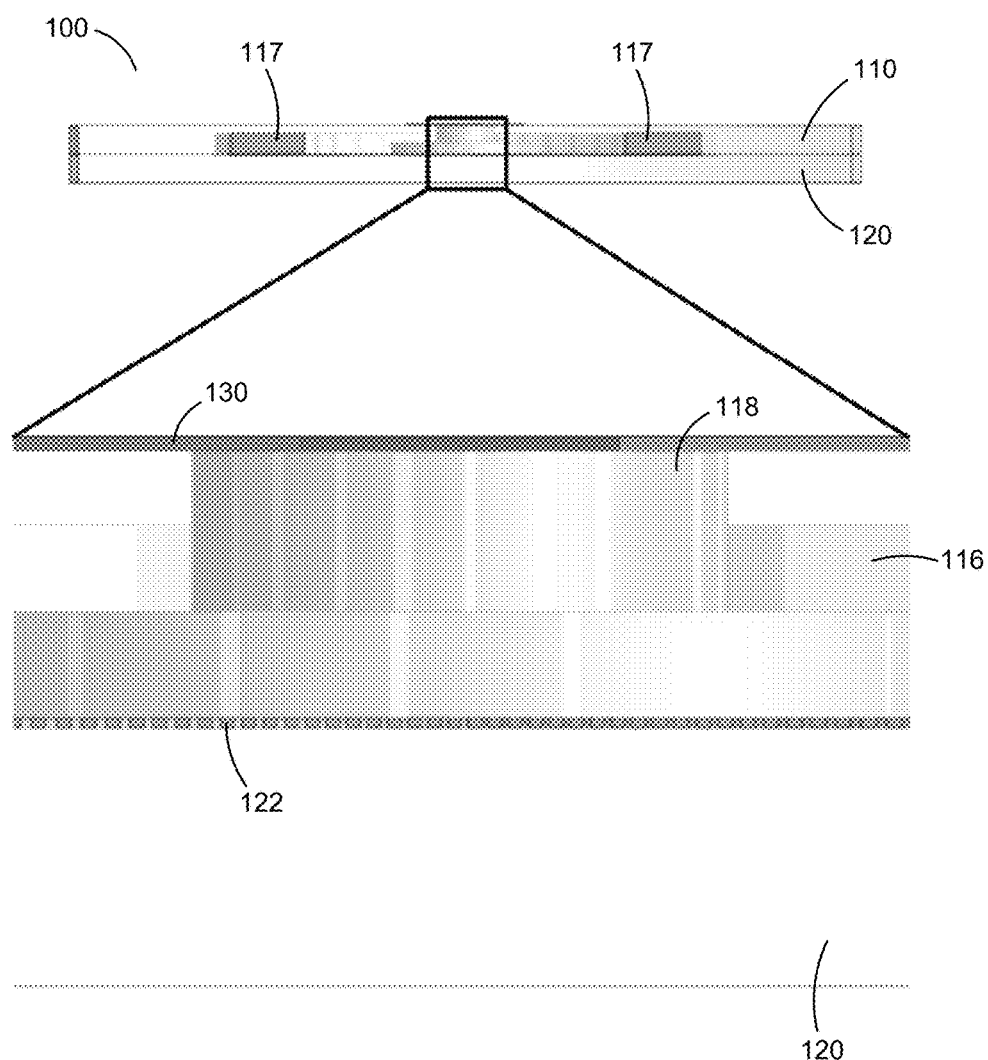
FIG. 2B is a cut-away view, partially enlarged, along line 2B-2B in FIG. 2A of the apparatus of FIG. 1.
Figure 2C:
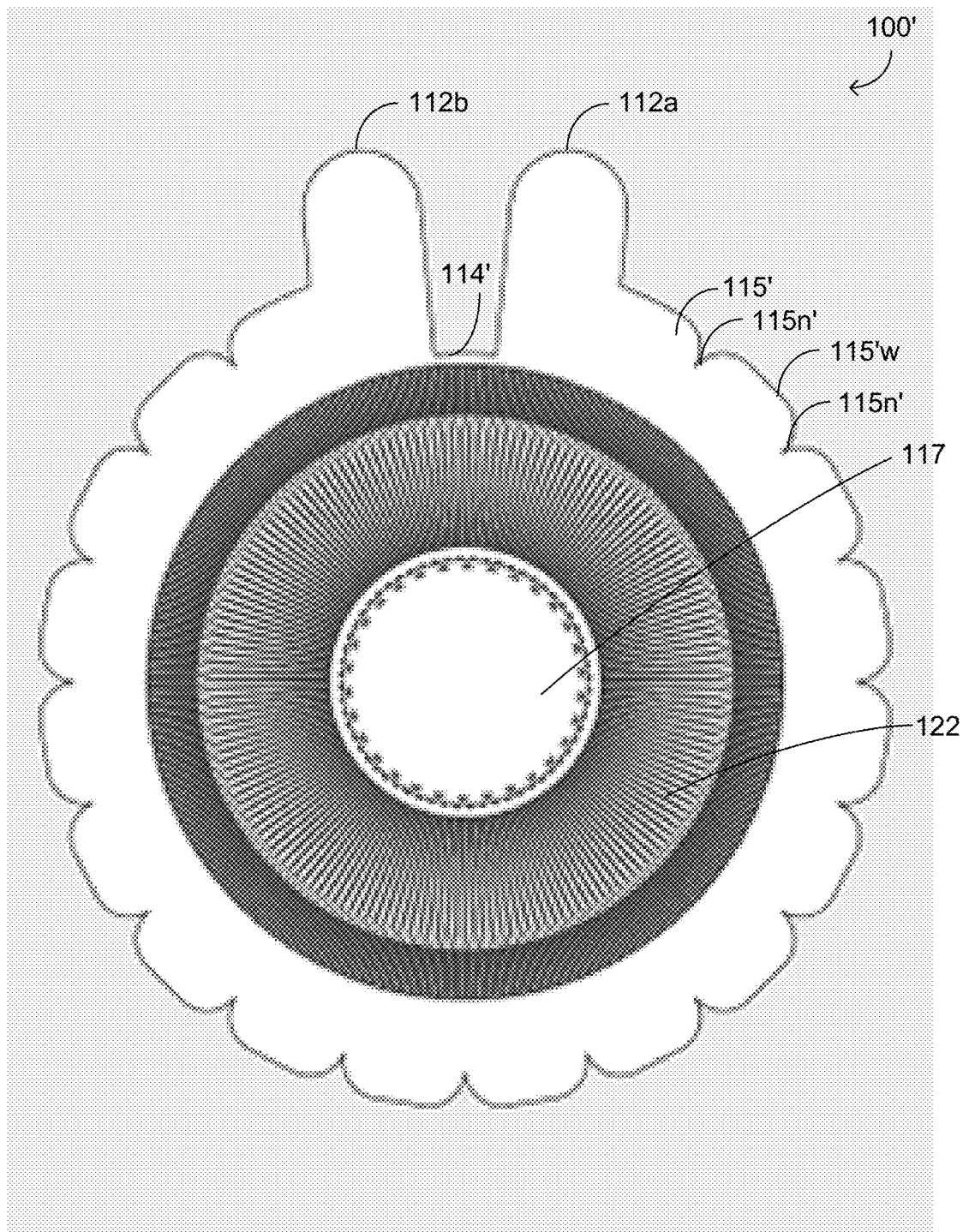
FIG. 2C is a top view of an example of an alternative embodiment of an apparatus for separating sperm.
Figure 3A:
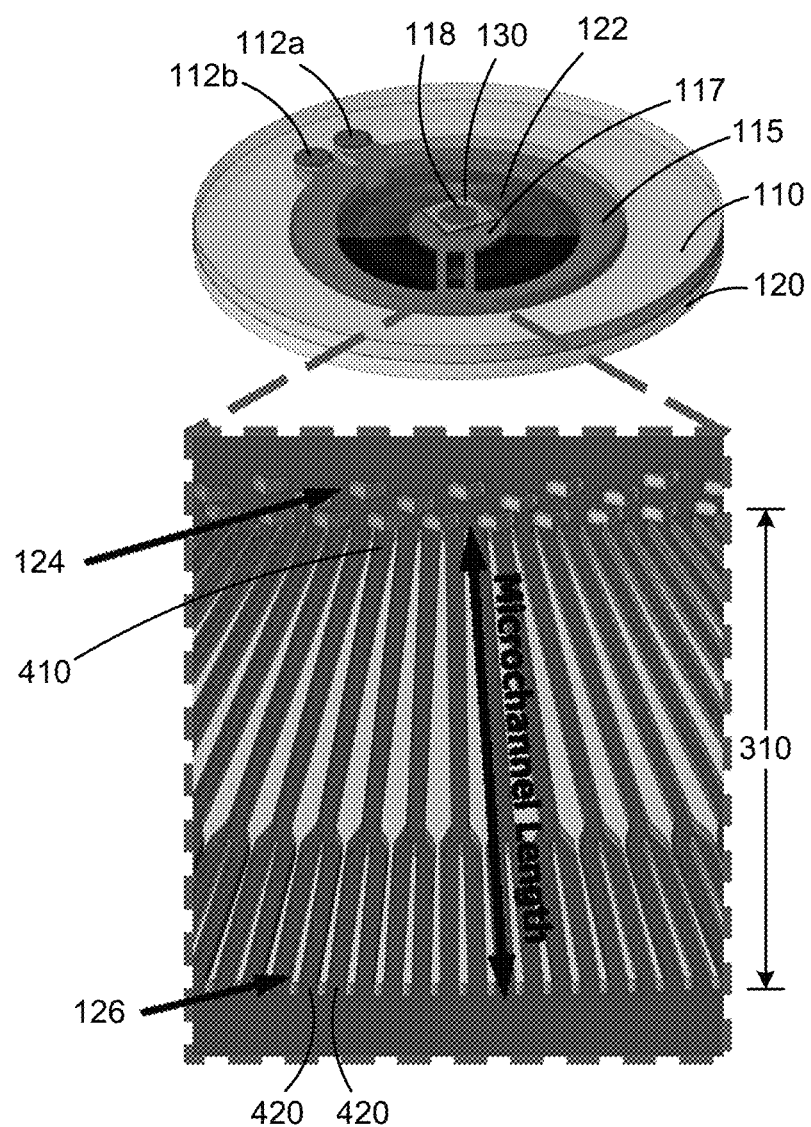
FIG. 3A is a perspective view, partially enlarged, of the apparatus of FIG. 1.
Figure 3B:
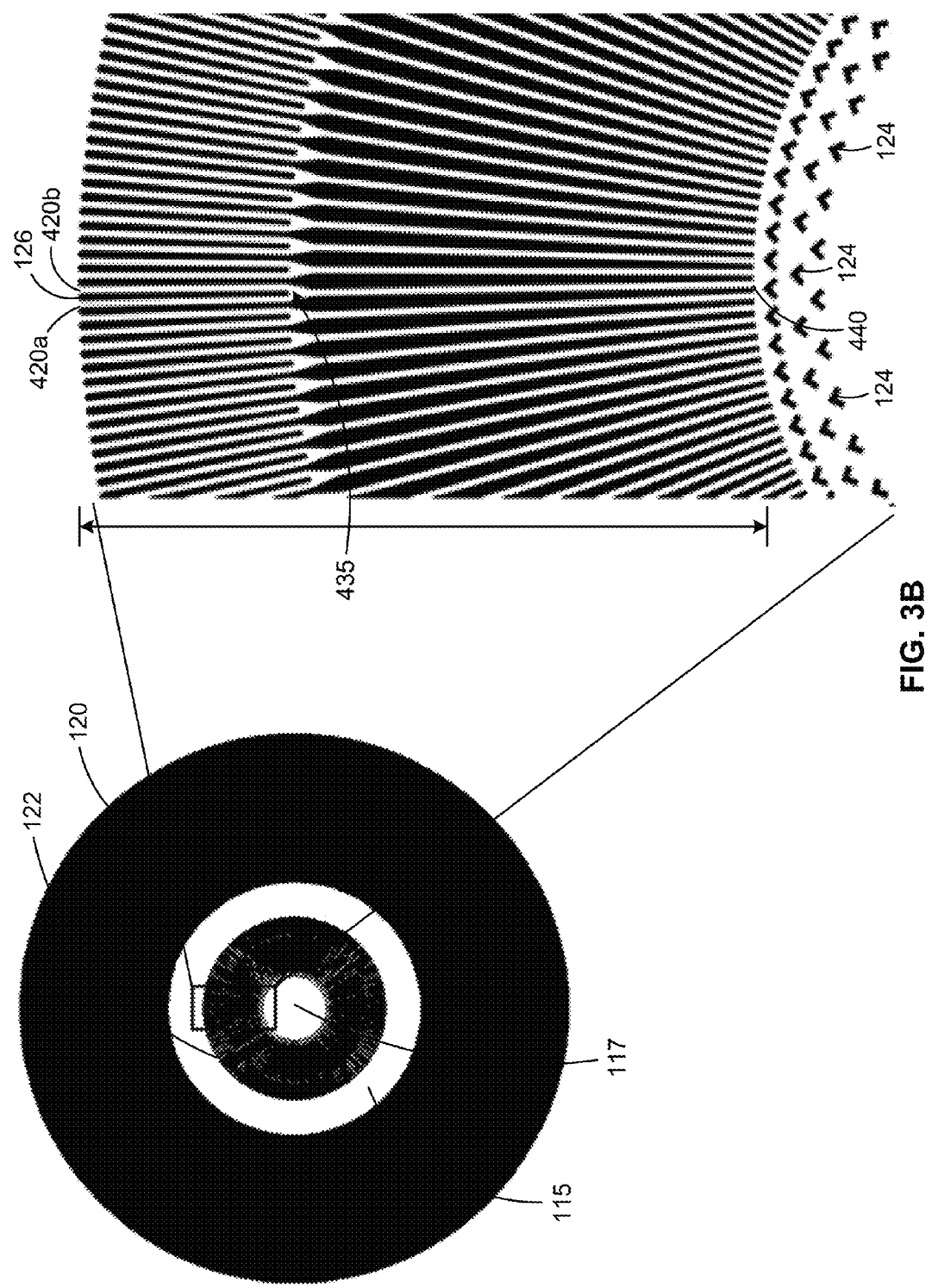
FIG. 3B is a top view, partially enlarged, of the array of microchannels for the apparatus of FIG. 3A.

Referring now to FIG. 2C, shown therein is a top view of an example of an alternative embodiment of an apparatus 100' for separating sperm. In this example embodiment, the ring-shaped inlet reservoir 115' comprises semicircular guides having semicircular guide walls 115'1 between notches 115n' that are disposed along the exterior wall of the inlet reservoir 115'. This wall extends from both sides of the inlet aperture 114. In some embodiments, the semicircular guides 115w' may have radii less than 150 μm. The semicircular guides 115w' serve to redirect boundary following sperm that are swimming along the exterior of the inlet wall towards the microchannels 122 leading to the outlet reservoir 117. The darker region of the microchannels 122 are due to microchannels that are narrower in size. The semicircular guides 115'w may be used in the other example embodiments of the sperm separating apparatus described in accordance with the teachings herein.

In some embodiments, funnel-shaped projections 124 may be provided on bottom layer 120 within the outlet reservoir 117 and adjacent to the microchannel network, to prevent sperm from swimming back into the microchannels (see e.g. magnification in FIG. 3A, FIG. 3B and FIG. 5 as well as some of the other figures) once they have reached the outlet reservoir (Galajda et al., 2007). For example, sperm that have swum through the microchannel array and past the projections 124 may be caught in the vertex of the funnel-shape, and thus prevented from re-entering the path outlets.

Turning to FIGS. 6A-6C, following the fabrication of top and bottom layers 110, 120 from PDMS (FIG. 6A), holes 112a, 112b for the inlet reservoir and/or hole 118 for the outlet reservoir may be punched using a standard biopsy punch. Bonding of the layers 110, 120 may be performed using either corona or plasma treatment (FIG. 6B).

While apparatus 100 has been described as being fabricated from a top layer 110 and a bottom layer 120, it will be appreciated that other methods of fabrication may be used in order to construct apparatus 100, including methods in which more (or fewer) layers are formed during the fabrication process.

As will be discussed further below, in order to prepare the apparatus 100 for use, inlet reservoir 115, outlet reservoir 117, and microchannel array 122 are filled with a suitable buffer fluid. Applying a vacuum while apparatus 100 is submerged in buffer fluid assists in removing air bubbles from the channels and may allow complete filling (FIG. 6C).

For example, apparatus 100 may be submerged in a dish with HEPES-buffered saline (HBS) buffer containing 1% polyvinyl alcohol (PVA) and 0.5% methyl cellulose (MC). This buffer is a high-viscous non-Newtonian viscoelastic medium that simulates the natural viscous mucus inside the female tract (Kirkman-Brown and Smith, 2011) and also serves to ensure high flow resistance and thus negligible flow in the microchannel network.

An example of a low viscosity fluid which may be used is commercially available sperm wash solutions as well as HEPES-buffered saline buffer comprising 1% polyvinyl alcohol here since it is also low viscosity.

When the microchannels are filled with a buffer (e.g. a high viscosity buffer), there may be minimal flow within the microchannels, mimicking the highly viscous in vivo environment. The flow resistance in the injection ring 115 may be $10^5$-fold that of the parallel microchannels, effectively eliminating flow within the microchannel array 122 during introduction of a semen sample into the inlet reservoir 115.

Optionally, an outlet closure member 130 (e.g. a temporary adhesive layer, such as an adhesive tape) may be used to cover the outlet reservoir hole 118 prior to injecting a semen sample into the apparatus. The aim of layer 130 is to generate a dead-end device without fluid flow in the channels during the semen injection and separation to further ensure a no-flow environment.

Optionally, one or more inlet closure members (not shown) may be used to cover the inlet reservoir holes 112a, 112b after a sample has been introduced into inlet reservoir 115. For example, a temporary adhesive layer, (such as an adhesive tape) may be used.

Figure 24:
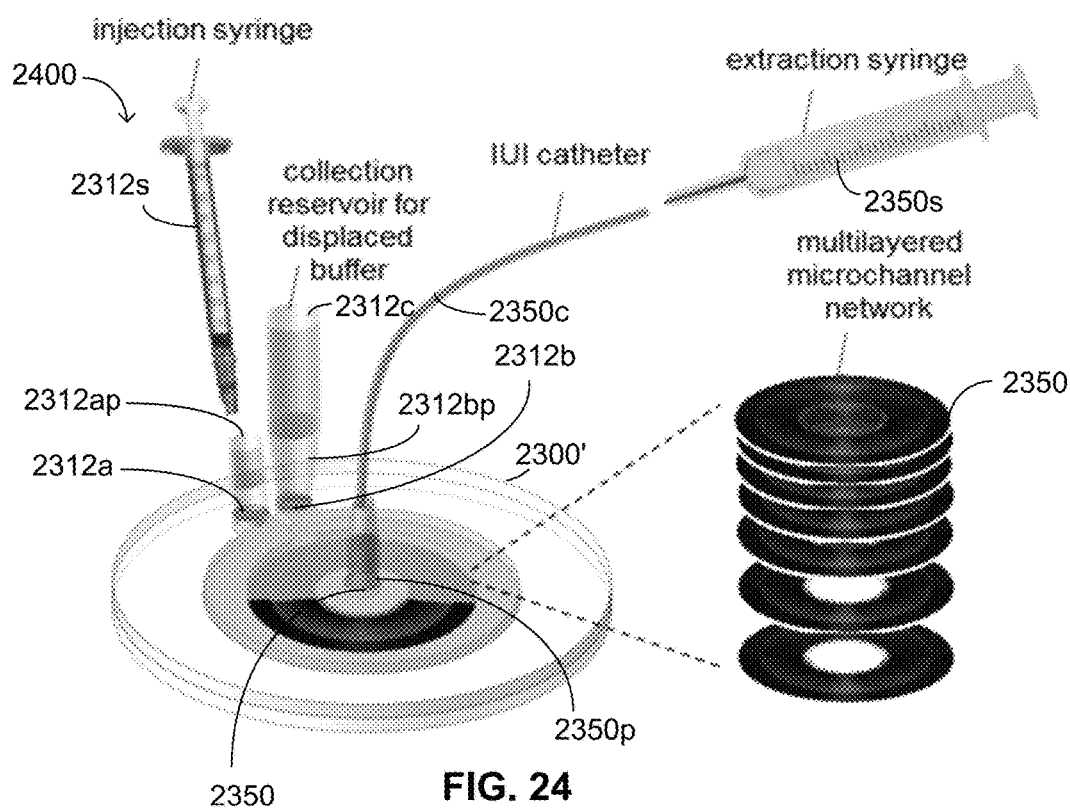
FIG. 24 is an example embodiment of a setup for injecting and extracting sperm for an apparatus for separating sperm that has stacked radial arrays of microchannels.

Alternatively, other embodiments may use syringe ports with caps for the inlet closure member and the outlet closure member 130 (e.g. see FIG. 24). Such embodiments permit the use of syringes to introduce the sample into the inlet and extract the sample from the outlet.

It will be appreciated that other suitable buffer solutions (e.g. less viscous aqueous buffers) may be used. For example, in order to ensure no flow, a high-viscosity buffer containing methyl cellulose (MC) was initially used for at least some of the experiments discussed below. However, as many fertility clinics typically do not use a high-viscosity buffer, subsequent tests were conducted on apparatus 100. Flow experiments with an aqueous buffer (e.g. a buffer with a viscosity approximately equal to that of water) showed that by nature of the apparatus design, no flow (or effectively no flow) is present, and adequate results were obtained with the use of outlet and/or inlet closure members (discussed below). In addition, sperm yield was higher with an aqueous buffer than with a high viscous buffer, and viability was generally similar to the results obtained with a high viscous buffer.

In at least some embodiments, before the semen sample is applied, the buffer-filled apparatus 100 may be equilibrated to 37° C.

An example method for separating sperm using apparatus 100 will now be described with reference to FIGS. 7A-7C.

Figure 7A:
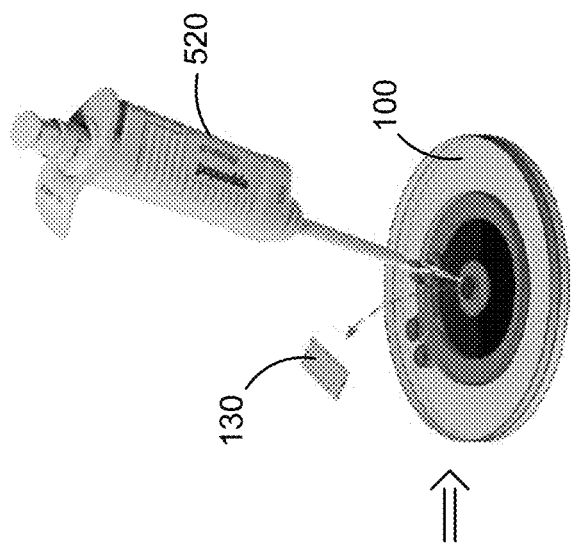
FIGS. 7A-7C are schematic diagrams of a method of separating sperm in accordance with at least one example embodiment.

As shown in FIG. 7A, a sample of raw, liquefied but untreated semen (e.g. a sample without any semen pre-treatment such as density gradient centrifugation or washing) is introduced into inlet reservoir 115. For example, a sample may be injected e.g. using a syringe 510 via inlet hole 112a (and/or inlet hole 112b). Such an approach provides for safe, fast (e.g. within 30 seconds or less), robust, and clinically applicable sample injection.

Figure 7B:
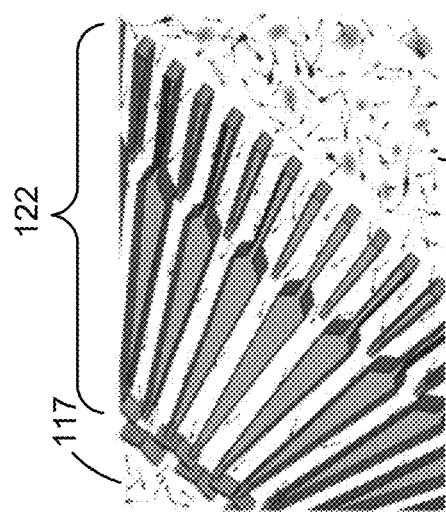

Once the sample has been introduced into the inlet reservoir, motile sperm navigate from the inlet reservoir 115, through the microchannel array 122, and into the outlet reservoir 117 while non-motile sperm and debris generally remain in the inlet reservoir 115 due to the static flow situation inside the device (see e.g. FIG. 7B). Navigation in a confined geometry, such as microchannel network 122, occurs due to the natural characteristic of sperm to follow boundaries.

Figure 7C:
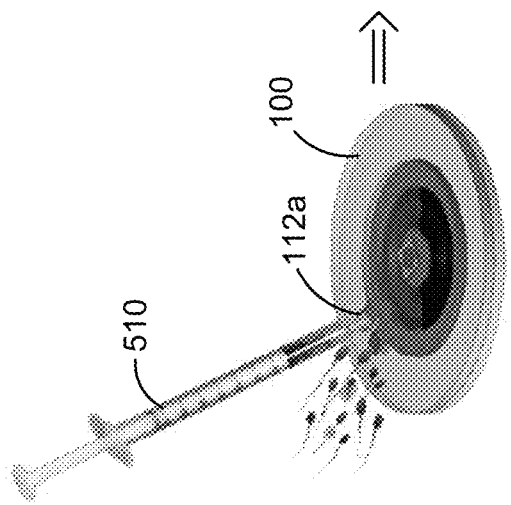

As shown in FIG. 7C, after a suitable period of time has elapsed to allow the motile sperm to navigate the microchannel array 122 (e.g. 15-20 minutes), the closure member 130 (where provided) may be removed and separated sperm may be collected from the outlet reservoir 117 in the center of the apparatus 100 (e.g. using a standard micropipette 520).

The output of this apparatus (i.e. the separated semen collected from the outlet reservoir 117) may be used directly for droplet base IVF, or for sperm selection prior to ICSI.

Alternatively, rather than introducing a semen sample into the outer ring-shaped inlet reservoir, and collecting sperm from the outlet reservoir, it will be appreciated that one could conceivably introduce a semen sample into the inner reservoir, and collect sperm that navigate a microchannel array (e.g. the microchannel array as shown in FIG. 4) from the outer ring-shaped reservoir. This may be useful, for example, for collecting a relatively dilute sperm/buffer solution—with high DNA integrity sperm—from the outer ring-shaped reservoir.

In one or more alternative embodiments, more than one radial array of microchannels may be provided in the apparatus, providing additional microchannel paths between an inlet reservoir and an outlet reservoir. Such an apparatus may provide further throughput when compared with apparatus having only one radial array of microchannels of similar dimensions. A higher throughput apparatus may be useful for processing large volumes of semen (e.g. for bovine (or other animal) applications), and/or for processing semen samples from men with normal semen samples (e.g. where good sperm motility and semen volume are expected, higher throughput may be used in order to attain sufficient sperm numbers for IUI).

Figure 22:
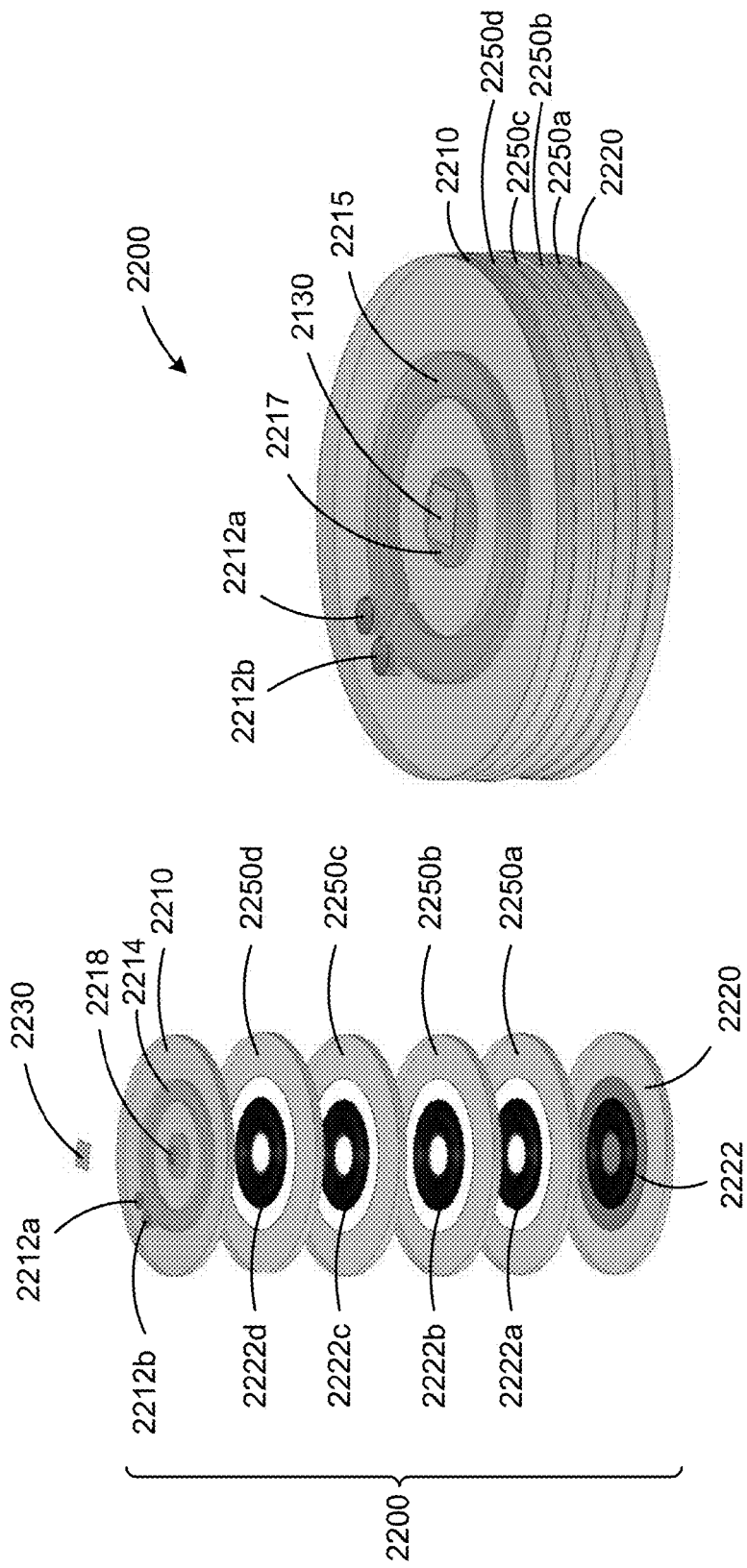
FIG. 22A is an exploded perspective view of an alternate apparatus for separating sperm in accordance with another embodiment.
FIG. 22B is a top view of the apparatus of FIG. 22A.

For example, FIGS. 22A-22B illustrate an example embodiment of an apparatus 2200 for separating sperm. Similar to apparatus 100, apparatus 2200 includes a top layer 2210 and a bottom layer 2220 having a radial array of microchannels 2222. Components similar to those in apparatus 100 have been similarly numbered, and will not be described further.

Apparatus 2200 also comprises four additional radial arrays of microchannels 2222a-d. These additional radial arrays may be fabricated in a similar manner as radial array 2220, and stacked on top of radial array 2220 to provide five layers of radial arrays of microchannels. To accommodate the increased thickness, one or more spacer rings 2250 may be provided between top layer 2210 and bottom layer 2220. The recessed inlet portion 2214 is configured to cooperate with bottom layer 2220 and/or spacer rings 2250 to form a (preferably) ring-shaped inlet reservoir 2215 with entrances to the microchannels in each radial array 2200, 2200a-d within the ring. It will be appreciated that the additional radial arrays and spacer rings are not necessarily shown to scale, as the channel-defining members of the additional radial arrays will typically be quite thin (e.g. 50-75 μm).

While four additional radial arrays of microchannels 2222a-d are shown, it will be appreciated that more (or fewer) additional layers each having a radial array of microchannels may be used in variant embodiments. Similarly, while four spacer rings 2250a-d are shown, more (or fewer) spacer rings may be used (e.g. based on the number of additional radial arrays that are used). It will be appreciated that the thickness of the spacer rings may vary, and that the number of spacer rings may not necessarily equal the number of additional radial arrays. For example, the thickness of a spacer ring may be based on the total thickness of the additional radial arrays, so that only one spacer ring may be required. Alternatively, the outer portion of top layer 2210 and/or bottom layer 2220 may be made thicker to accommodate the added thickness of additional radial arrays, obviating the need for separate spacer rings.

Referring now to FIG. 23, shown therein is an exploded perspective view of an example of an alternative embodiment of an apparatus 2300 for separating sperm. The apparatus 2300 comprises a top layer 2310, an intermediate layer 2320, a bottom layer 2325 and a stack of microchannels 2350 comprising multiple radial arrays of microchannels. The top layer 2310 comprises first and second inlet apertures 2312a and 2312b and an outlet aperture 2330. The intermediate layer 2320 comprises inlets 2312a and 2314a that align with apertures 2312a and 2312b, respectively when the top layer 2310 is placed on the intermediate layer 2320. The intermediate layer 2320 also has contoured sidewalls 2315w that form an inlet ring when the stack of radial arrays of microchannels 2350 is placed at the center of the intermediate layer 2320. The stack of radial arrays of microchannels 2350 is disposed such that the outlet 2350o of the stack of radial arrays of microchannels 2350 is aligned with the outlet aperture 2330 when the top layer 2310 is placed on the intermediate layer 2320. The contoured sidewalls 2315w aid in directing the sperm to the stack of radial arrays of microchannels 2350 during use. In this regard, the contoured sidewalls 2315w may have a repeating semi-circular shape, as is shown in FIG. 23, or they may have another suitable shape that performs this function.

In the embodiment of FIG. 23, the stack of radial arrays of microchannels 2350 help the sperm find a channel that leads to the outlet 2350o during use. In other words, there are a plurality of radial arrays 2350 each having a plurality of microchannels that are coupled to the inlet reservoir 2314a, 2314b and the outlet reservoir 2350o and the radial arrays are stacked to increase the number of microchannel paths between the inlet reservoir 2314a, 2314b and the outlet reservoir 2350o thereby increasing the number of possible channels that exist connecting the inlet to the outlet and increasing the ease with which the sperm find a microchannel. In some embodiments, there may be between 2 to 16 stacked radial arrays while in other embodiments there may be more than 16 stacked radial arrays.

Referring now to FIG. 24, shown therein is an example embodiment of a setup 2400 for injecting and extracting sperm for apparatus 2300' for separating sperm that has stacked radial arrays of microchannels. In this case the apparatus 2300' comprises an inlet port 2312ap coupled to the inlet aperture 2312a. A syringe 2312s may then be used to introduce sperm sample into the inlet aperture 2312a by coupling the working end of the syringe 2312s with the inlet port 2312ap. The apparatus 2300' further comprises an inlet port 2312bp for coupling with the inlet aperture 2312b. A collection reservoir may then be coupled to the inlet port 2312bp to collect any displaced buffer solution during use. The apparatus 2300' further comprises an outlet port 2350p for coupling with the outlet aperture 2350. An extraction syringe 2350s may be coupled to the outlet port 2350p via a conduit 2350c such as a catheter to collect sperm from the outlet aperture 2350 during use. Accordingly, in this example embodiment, the inlet ports 2312ap, 2312bp and the outlet port 2350p are syringe ports.

Experimental Results:

In order to assess the impact of varying the channel length 310 (see e.g. FIGS. 3A and 3B), three different devices were designed with a channel length 310 of 6 mm, 7.5 mm, and 9 mm. A number of experiments were performed, where selected sperm collected from the outlet reservoir under various conditions were examined to quantify device performance in terms of selected sperm vitality and DNA integrity.

Experimental Procedure—General:

The microfluidic sperm selection device was filled by submerging the device in buffer and applying vacuum pressure (e.g. −30 psi) for at least 90 minutes. Following this step, the device was placed inside an incubator (37° C.) for 1 hour to reach physiological temperature. To let the flow stabilize inside the device, at least 10 minutes prior to the experiment, the device was transferred from the incubator to a hot plate (37° C.). A 1 mL BD plastic syringe was used to inject 1 mL of raw semen sample into the device (See e.g. FIG. 7A). Experiments were conducted for 10, 15, and 20 minutes to investigate the effect of time on selected sperm concentration, count, vitality, and DNA integrity. At the end of experiment duration (i.e. time allowed for sperm to swim inside the device), the temporary layer was removed from the outlet and 100 μL of the buffer containing selected sperm were isolated from the outlet using a 100 μL Eppendorf pipette (See e.g. FIG. 7C).

Bull sperm concentration, count, and vitality were assessed with the fluorescent-based LIVE/DEAD sperm viability kit (L-7011; Invitrogen, NY, USA). Sperm were labelled either before semen injection or 10 minutes after sample collection. Labelled specimens were loaded into a haemocytometer and an inverted fluorescent microscope (DMI 6000B, Leica) with a charge-coupled device (CCD) camera was used to capture 100 times magnification images in bright field (total number of sperm), green fluorescence (live cells), and red fluorescence (dead cells). The cell counter plugin of the free available image processing software ImageJ was used to process the images. Sperm that were labelled both as 'live' and 'dead' were considered 'live' during counting. In the case of the human sperm experiments, sperm concentration was measured using a haemocytometer (Hausser Scientific, PA, USA) followed by SCSA to analyze DNA integrity.

Experimental Procedure—Device Fabrication:

When fabricating sperm separation apparatus 100 for the experiments discussed further below, the parallel microchannels array in the bottom layer was designed in AutoCAD and printed on a photomask (Pacific Arts & Designs Inc., Markham, Canada). The master was fabricated with a SU-8 2075 negative photoresist (MicroChem, Newton, Mass., USA) using standard soft-lithographic techniques (Unger et al., 2000). The microchannels have a depth of 75 μm. To fabricate the top layer master, the features were designed in AutoCAD and cut from 1.45 mm and 0.8 mm thick PMMA (Plastic Word, Toronto, Canada) using a M-360 $CO_2$ ablation laser (Universal Laser Systems Inc., Scottsdale, Ariz., USA). The PMMA was then bonded to a petri dish in order to complete the master and hold the PDMS for the top layer. Both top and bottom layers were fabricated using PDMS (Silgards 184: Dow Corning, MI, USA) substrate with 1:10 mixing ratio, and bonded with a hand-held corona treater (BD-20AC, Electro-Technic Products Inc., IL, USA) (Haubert et al., 2006). Two 4 mm diameter inlet ports at each end of the injection ring and a 5 mm diameter outlet port at the centre of outlet were punched in the top layer using Miltex Punch Dermal Biopsy. Finally, transparent tape was used as a removable top seal to close the outlet during the sample injection and experiments duration.

Experimental Procedure—Semen Sample Preparation:

For the bull semen, straws containing 500 μL of bull semen (ABS Global Inc., Canada) were stored in liquid nitrogen. Before use, the bull specimen were thawed in a water bath at 37° C. and removed from the straw using an artificial insemination syringe. The bull semen was kept at 37° C. at all times, and experiments were conducted within 10 min of semen transfer into the incubator.

For the human semen, fresh ejaculated human semen was obtained from healthy donors (n=8) by masturbation after 2-4 days of sexual abstinence and incubated for 30 min at 37° C. to allow liquefaction. Experiments were conducted within 10 minutes of liquefaction. Standard semen parameters were obtained in accordance to WHO guidelines (WHO Press, 2010) using computer-aided sperm analysis (CASA). All donors signed an informed consent, and the information for this study remained confidential and within the institution. This study was approved by the ethics review board at McGill University.

Experimental Procedure—Buffer Preparation

HEPES (4-(2-hydroxyethyl)-1-piperazineethanesulfonic acid)-buffered saline (HBS) with NaCl (135 mM), KCl (5 mM), D-Glucose (12 mM), HEPES (25 mM) (Bioshop Canada Inc., Burlington, Canada), and $Na_2HPO_4.2H_2O$ (0.75 mM, Sigma-Aldrich Corp, MO) was used as the base solution to prepare the experimental buffer. To prevent sperm from sticking to the surface, PVA (Sigma-Aldrich Corp, MO) was added to a final concentration of 1 mg/mL. Methyl cellulose (MC) (M0512; Sigma-Aldrich Corp, MO) was dissolved in HBS/PVA to prepare a 0.5% MC solution, which resulted in a non-Newtonian viscoelastic solution with an approximate viscosity of 25 cp at 20° C. Finally, a 1 M solution of NaOH (VWR, West Chester, Pa.) was used to adjust the buffer to pH 7.4 at room temperature. The buffer was stored at 4° C. and all devices were loaded and tested no later than 7 days after buffer preparation.

Experimental Procedure—Sperm Chromatin Structure Assay (SCSA)

Figure 10B:
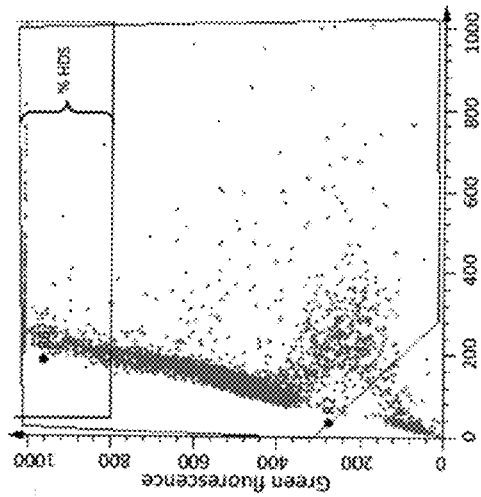
FIGS. 10A-10D are charts showing representative sperm chromatin structure assays (SCSAs) for 10 min human sperm experiment with 7.5 mm device.
Figure 10D:
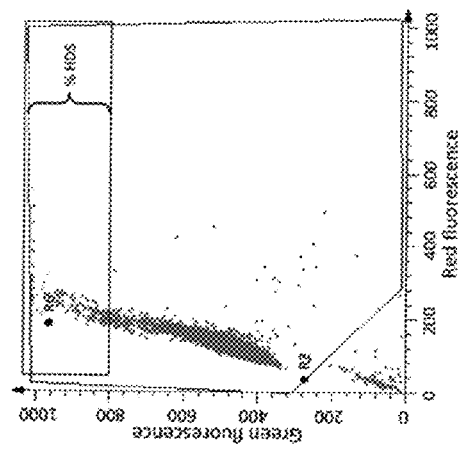
Figure 10A:
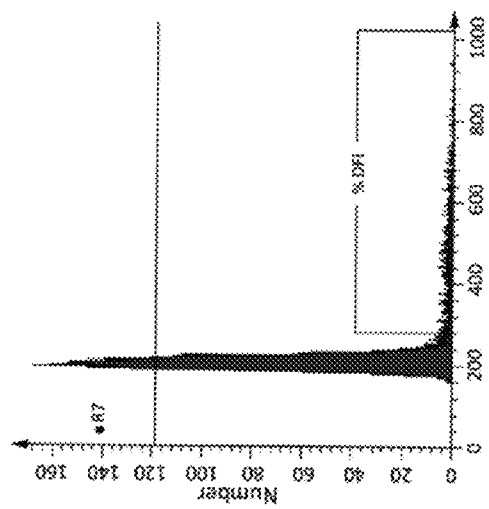
Figure 10C:
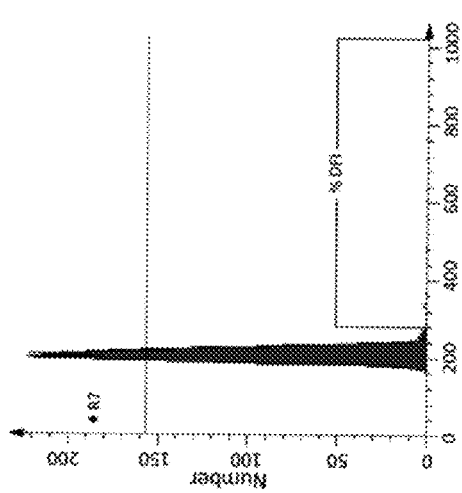

Sperm DNA integrity was assessed using the sperm chromatin structure assay (SCSA) and the results were expressed as sperm percentage DFI (an index of DNA damage) and sperm percentage HDS (a measure of nuclear chromatin compaction) as previously described (Evenson et al., 2002; Zini et al., 2001). Frozen stored samples were thawed on ice, diluted with THE buffer (0.1M Tris buffer, 0.15 M NaCl, 1 mM Ethylenediaminetetraacetic acid (EDTA), pH 7.4) and then treated with 0.40 ml of acid-detergent solution (0.08 M HCl, 0.15 M NaCl, 0.1% Triton X-100, pH 1.2). After 30 sec, the samples were stained by adding 1.2 ml acridine orange (AO) stain solution containing 6 μg AO (chromatographically purified; Cat. #04539, Polysciences Inc., Warrington, Pa., USA) per ml buffer (0.037 M citric acid, 0.126 M Na2HPO4, 0.0011 M EDTA (di-sodium), 0.15 M NaCl, pH 6.0). After 3 min, fluorescence was measured for a minimum of 5000 cells using a MACSQuant Analyzer (Miltenyi Biotech GmbH, Teterow, Germany) equipped with an argon laser. Excitation occurred at 488 nm, and double-stranded DNA and single-stranded DNA could be detected as green and red fluorescence, respectively. WinList software (Verity Softwarehouse Inc., Topsham, Me., USA) was used to generate the cytogram (red vs. green fluorescence) and histogram (total cells vs. DFI) plots, as well as, % DFI and % HDS readings (see e.g. FIGS. 10B, 10D).

Channel Length—Bull Sperm

Figure 8B:
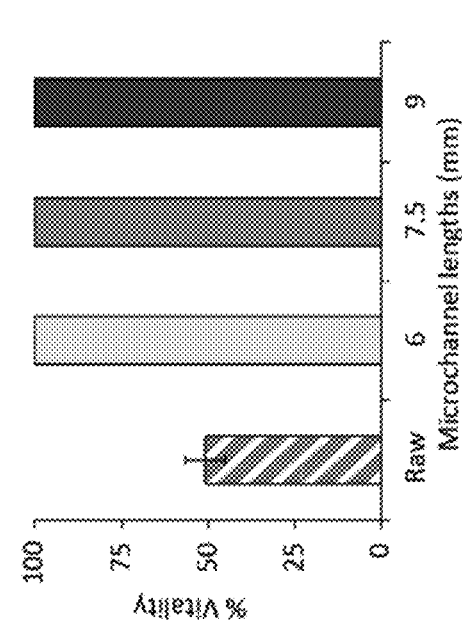
FIGS. 8A-8D are charts showing sperm concentration and vitality for 15 min experiment with bull sperm.

Live/dead viability staining of bull sperm was applied to assess device function, selected sperm concentration and selected sperm vitality. FIGS. 8A-8B show results for the cases where the live/dead staining was performed before sample injection (n=5). Total sperm concentrations collected at the outlets of the three devices are plotted with the raw sample concentration in FIG. 8A, with the corresponding outlet sperm counts shown inset. With an average 40M sperm in the 1 mL sample introduced at the inlet, concentrations on the order of 1M/mL and corresponding sperm counts on the order of 100,000 are collected at the outlets. Results for the three devices indicate that isolated sperm concentration decreases linearly with microchannel length ($R^2$=0.99), with lower concentrations of faster sperm selected in longer microchannels.

As illustrated in FIG. 8B, pre-staining of sperm revealed that the percentage vitality of selected sperm was always 100% regardless of the microchannel lengths and percentage vitality of the sperm in raw semen. In the absence of flow within the device, all the initially dead sperm and debris remained at the inlet, and only the live and motile sperm were able to reach the outlet. This characteristic enables simultaneous semen purification and sperm selection on-a-chip without any prior semen treatment.

Figure 8D:
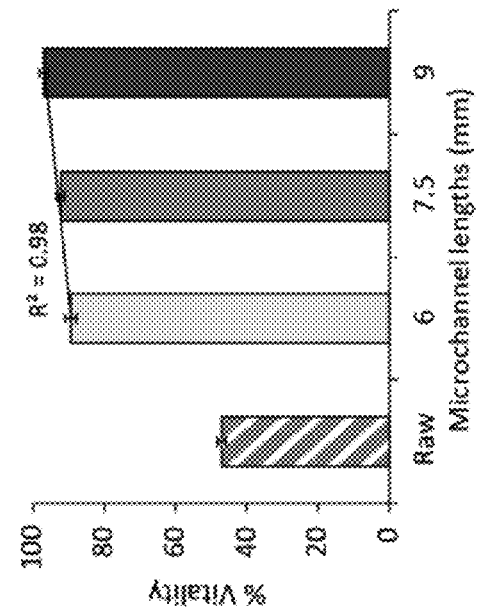
Figure 8A:
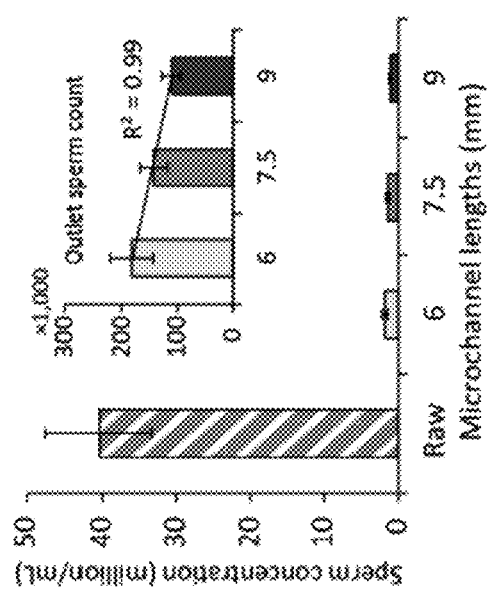
Figure 8C:
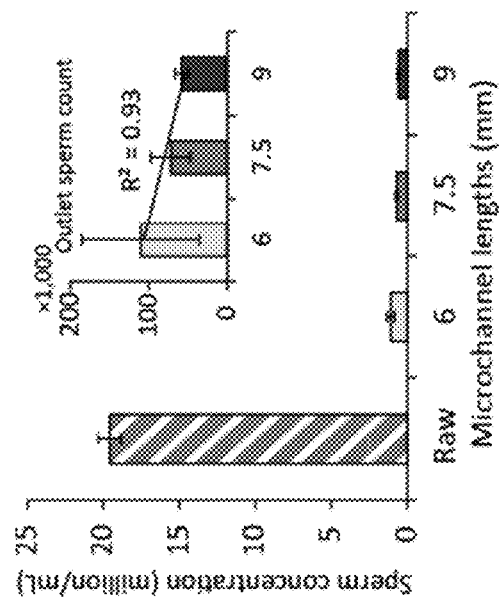

FIGS. 8C and 8D show results for the cases where the live/dead staining was performed after the selection process (n≥4). The sperm were stained 30 min after collection as required for the staining procedure (staining started 10 min after the sample collection and takes 20 min to occur). Similar to the pre-staining experiments (FIG. 8A), selected sperm concentrations and counts decreased linearly ($R^2$=0.93) with microchannel length (FIG. 8C). It was also observed that by decreasing the raw semen concentration in the inlet, the concentration of collected sperm decreased with approximately the same order of magnitude (0.5 in this case) suggesting that the selection efficiency is relatively constant with an initial concentration in the range of 20M/ml to 40M/ml.

FIG. 8D shows the percentage vitality of selected sperm after sample collection in comparison with the raw semen introduced on-chip. The results indicate that the 9 mm device yields more than 97% sperm vitality 30 min after the experiments, and this number decreases to 92% and 89% for 7.5 mm and 6 mm devices, respectively. Using the 9 mm device as an example, the data indicate that the selected sperm population demonstrates a 106% greater percent vitality (when compared to the 47% vitality in raw semen). The linear trend ($R^2$=0.98) indicates that devices with longer channel lengths select motile sperm with better vitality than devices with shorter channel lengths. Taken together, the data suggest that in devices with shorter channels, a greater number of motile sperm are able to reach the outlet but these sperm will die more rapidly than sperm that have been selected with longer channel lengths.

Duration—Bull Sperm

Figure 9:
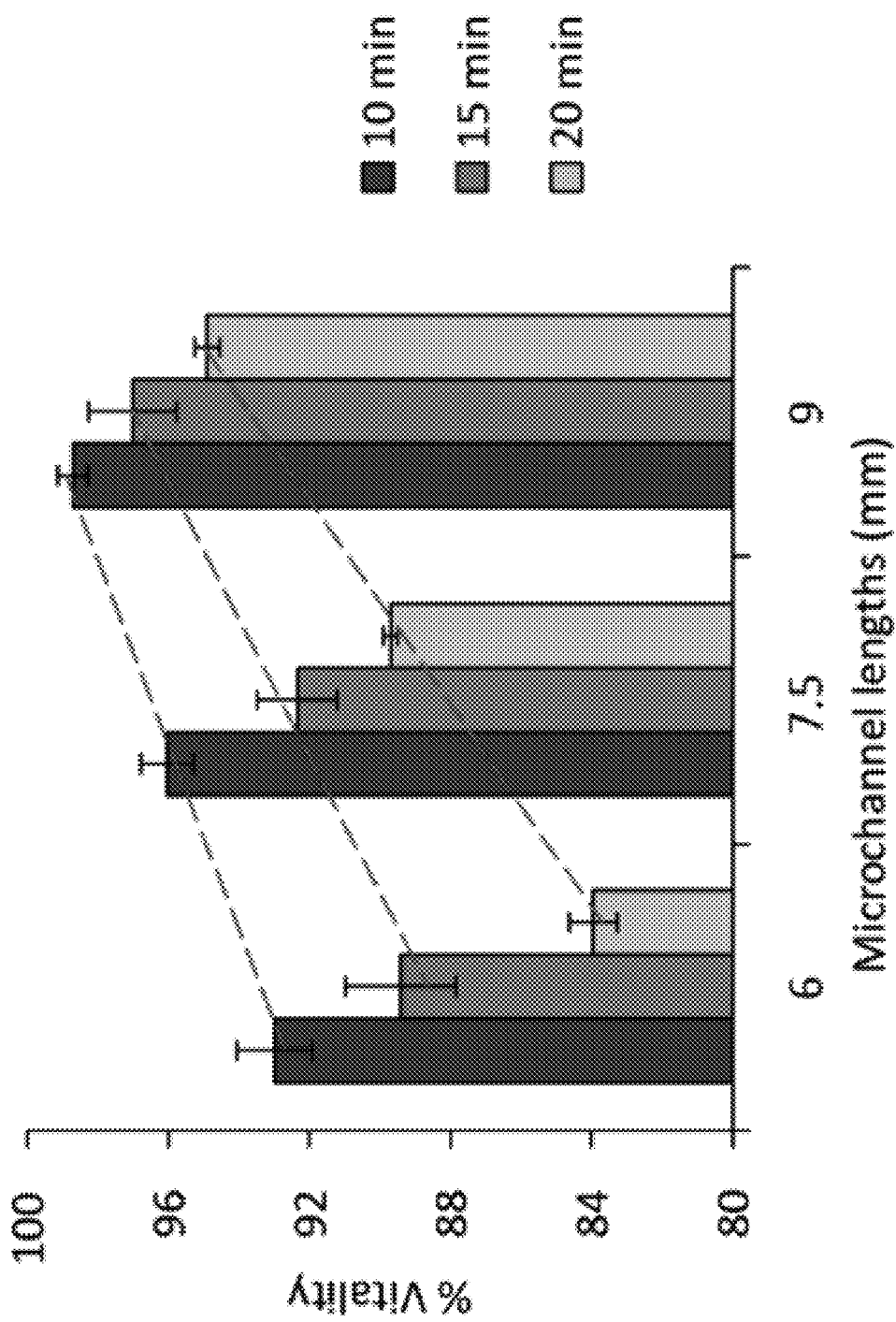
FIG. 9 is a chart showing the effect of time and microchannel length on selected bull sperm vitality.

In order to assess the effect of experiment duration on sperm vitality, bull sperm were processed for 10, 15, and 20 minutes in apparatus with 6 mm, 7.5 mm, and 9 mm microchannel lengths (n≥4). FIG. 9 shows selected sperm vitality 30 min after sample collection indicating that for the same microchannel lengths, selected sperm vitality decreases when increasing the experimental time. Increasing the experiment duration from 10 min to 20 min in the 6 mm device substantially reduces the percentage vitality from 93% to 84%. In contrast, the longer microchannels increase the selected sperm vitality and reduce the variation caused by changes in experimental time. For example, in a 9 mm device the percentage vitality decreases by only 5% (from 99% to 94%) when changing the experiment duration from 10 min to 20 min. These findings appear to indicate a strong correlation between rapid progressive sperm motility and vitality since sperm with highly progressive motility are able to swim greater distances in a shorter amount of time and will subsequently exhibit a higher vitality than sperm with less rapid progressive motility. The trend also indicates that the act of swimming further through the device did not have a negative impact on sperm vitality, or, at minimum, any potential negative effect was more than compensated by the higher vitality of the faster swimming population.

Channel Length—Human Sperm

DNA integrity is a metric for sperm quality and fertilizing capacity. Poor sperm DNA integrity is linked to lower natural and assisted pregnancy rates and to a greater risk of pregnancy loss in both IVF and ICSI (Coughlan and Ledger, 2008; Zini et al., 2008; Zini and Sigman, 2009). All three devices were clinically tested with fresh human semen to quantify the DNA integrity of sperm selected and the role of channel length and test duration. The sperm chromatin structure assay (SCSA) was used to assess DNA integrity as it is known to produce reliable and reproducible results when evaluating the level of DNA damage (Evenson, 2013; Bungum et al., 2011; Evenson et al., 2002). The SCSA was used to measure two markers of sperm chromatin and DNA damage: percent DNA fragmentation index (% DFI—a measure of DNA strand breaks); and percent high DNA stainability (% HDS—a measure of chromatin compaction) (see representative assay results in FIGS. 10A-10D, where green fluorescence indicates very low levels of DNA fragmentation and red fluorescence indicates high levels of DNA fragmentation.) (Evenson et al., 2002). A high % DFI indicates a high percentage of sperm with DNA strand breaks and a high % HDS indicates a high proportion of sperm with poor chromatin compaction.

Figures 11A, 11B, 11C:
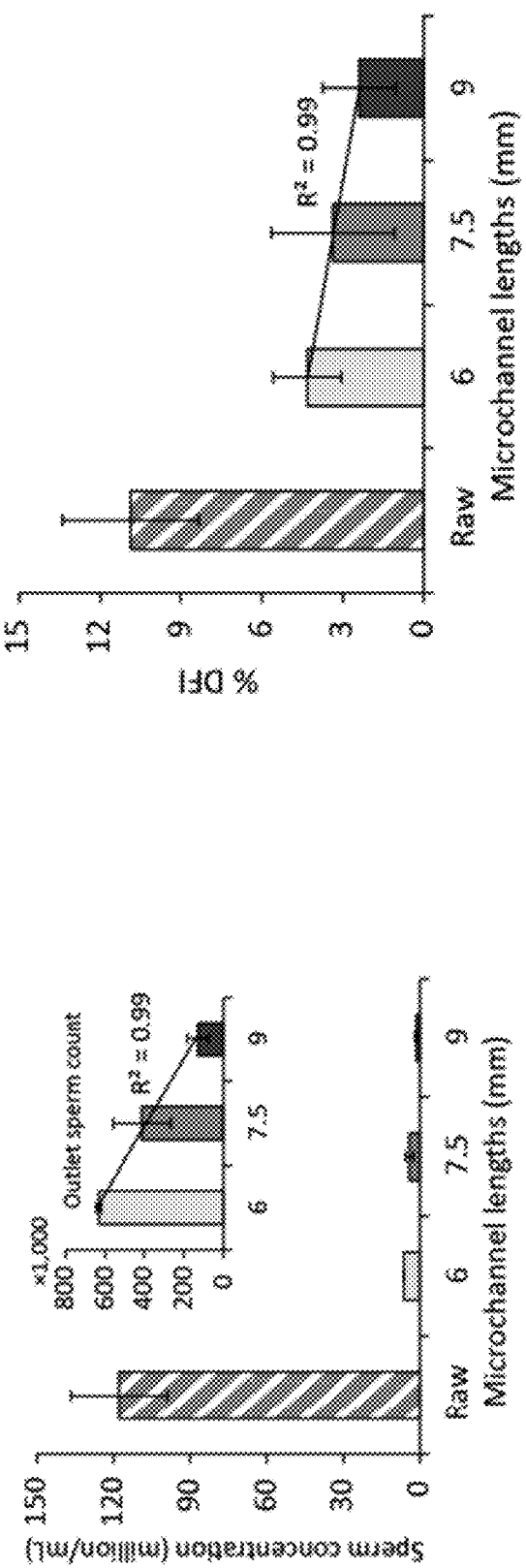

FIGS. 11A-11C show selected human sperm concentration, count, % DFI, and % HDS in comparison with the initial raw semen sample (n=4). The results indicate that with an average 120M sperm in the 1 mL sample introduced at the inlet, 100 µL samples with more than 630,000, 410,000, and 120,000 sperm were collected from 6 mm, 7.5 mm and 9 mm devices, respectively (with corresponding concentrations of 6.32M/mL, 4.12M/mL, and 1.29M/mL) (FIG. 11A). Experiment time was 10 min in each case.

Figure 12A:
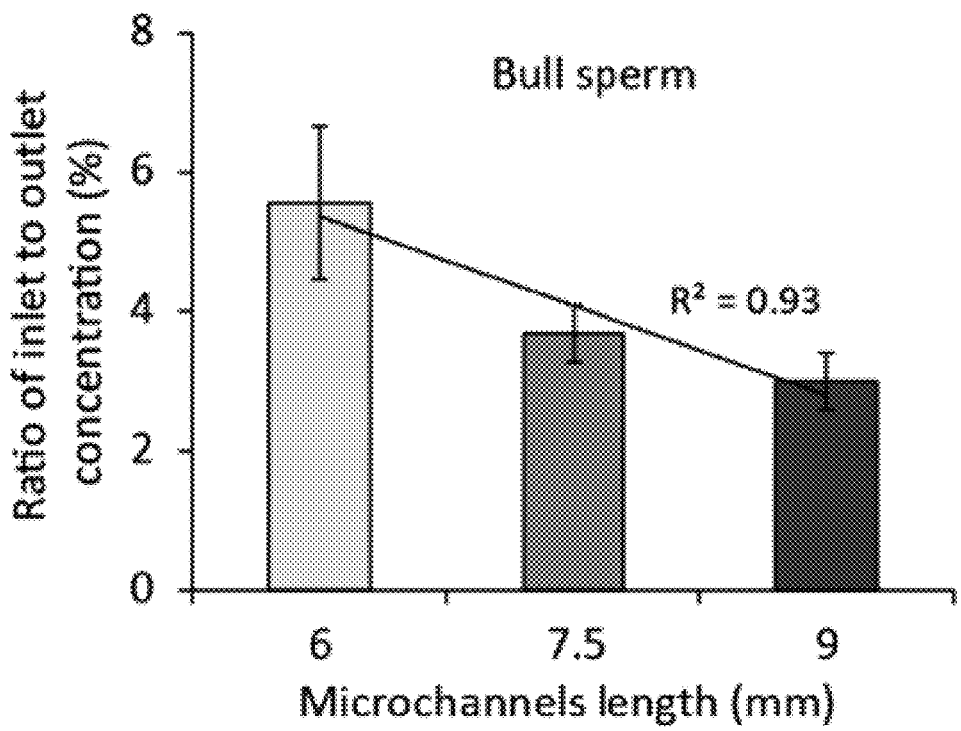
FIGS. 12A-12B are charts showing percentage ratio of inlet to outlet concentration for both bull (FIG. 12A) and human (FIG. 12B) sperm (n≥4) for 6 mm, 7.5 mm, and 9 mm device runs.
Figure 12B:
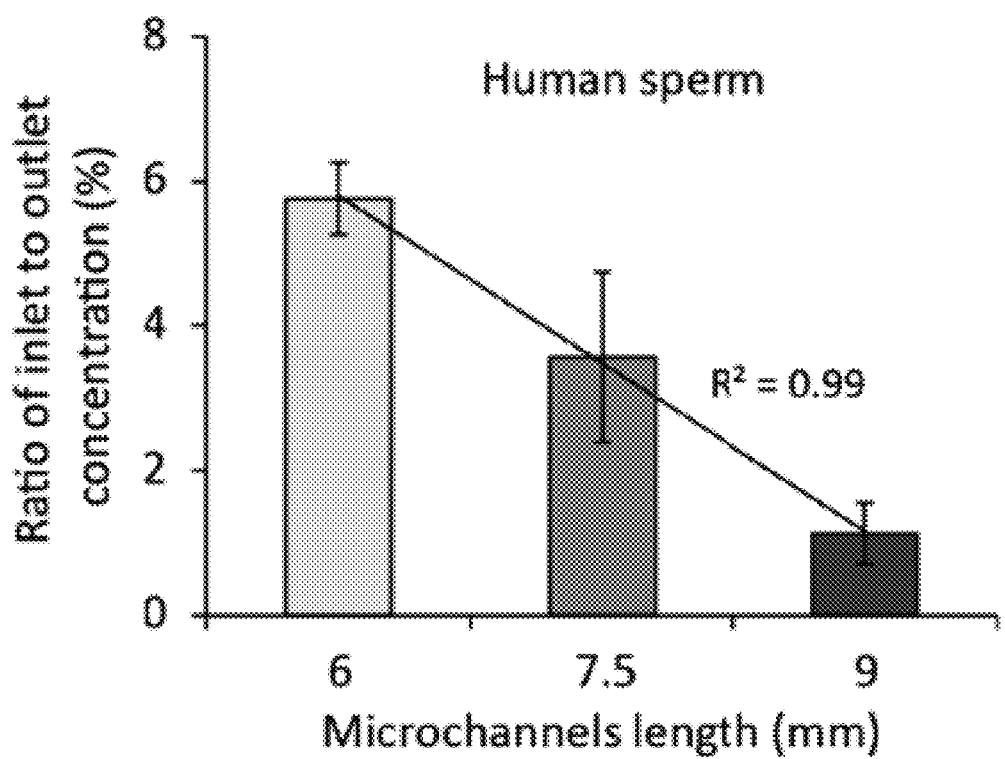

Analogous to the bull sperm results (FIG. 8C), the concentration and counts of the selected human sperm linearly decrease with microchannel length ($R^2=0.99$). While the selected sperm counts were similar for the bull and human tests, the human test samples had higher initial counts and the tests were shorter in duration (10 min vs. 15 min). The human sperm counts collected are on the order of $10^3$-fold that of the inlet counts, which is indicative of an effective selection process. It is noteworthy, however, that the output counts and concentrations remain sufficient for clinical application. In addition, the ratio of inlet to outlet sperm concentrations is very similar across devices in both bull and human sperm (see a comparison of the plots in FIGS. 12A-12B). It is also noteworthy that the concentrations show a consistent trend in both human and bull sperm tests. However, due to the 10-fold difference in inlet and outlet sample volume, it is important not to confuse the concentration ratio plotted with selection rate (i.e. count of sperm selected versus count of sperm injected).

Human sperm DNA and chromatin integrity parameters, % DFI and % HDS, for the selected sperm and raw semen as a function of device length are plotted in FIGS. 11B-11O. The % DFI was 10.9 for the raw semen and 4.32, 3.37 and 2.40 for the selected sperm in the 6 mm, 7.5 mm, and 9 mm devices, respectively. Results show a strong negative linear correlation between % DFI and microchannel length ($R^2=0.99$), indicating reduced DNA fragmentation with increased microchannel length. Specifically, the % DFI in the selected sperm from the 6 mm, 7.5 mm and 9 mm devices was lower by 60%, 70% and 78%, respectively, when compared to the raw semen sample. Results for % HDS indicate similar trends with a weaker correlation ($R^2=0.76$) than observed for % DFI (FIG. 11C). The % HDS was 4.21 for the raw semen and improved by 46%, 79% and 80% in the 6 mm, 7.5 mm and 9 mm devices, respectively (with corresponding % HDS of 2.25, 0.86 and 0.84). These values compare favorably to the most common current methods of sperm preparation, swim-up and density gradient centrifugation, with maximum reported improvements of 50% (de Lamirande et al., 2012; Zini et al., 2002).

Overall, analyses with human sperm revealed that the highest concentration can be isolated from the 6 mm device and decreases linearly with the length of the channel (FIG. 11A). Comparison of the DNA quality parameters DFI and HDS of the raw semen sample and separated samples shows that fragmentation is significantly reduced after separation with the microfluidic device. Further, the percentages of DFI and HDS are lower in the 7.5 mm and 9 mm devices than in the 6 mm device (FIGS. 11B-11C). This means that the device with a channel length of 7.5 mm produces the best results with regard to concentration and DNA quality.

Duration—Human Sperm

Figure 13B:
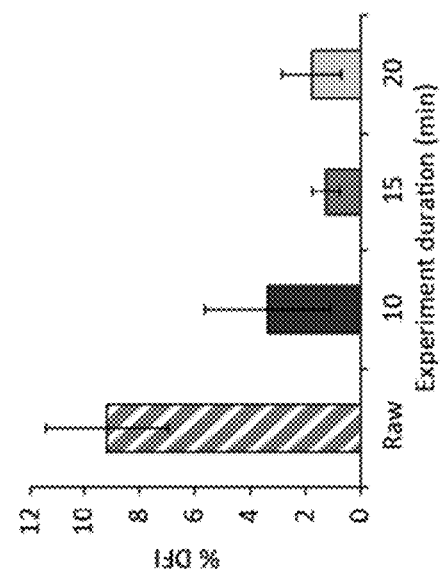
FIGS. 13A-13C are charts showing selected human sperm count and DNA integrity results for 10, 15, and 20 minute experiments using 7.5 mm devices (n=4)
Figure 13A:
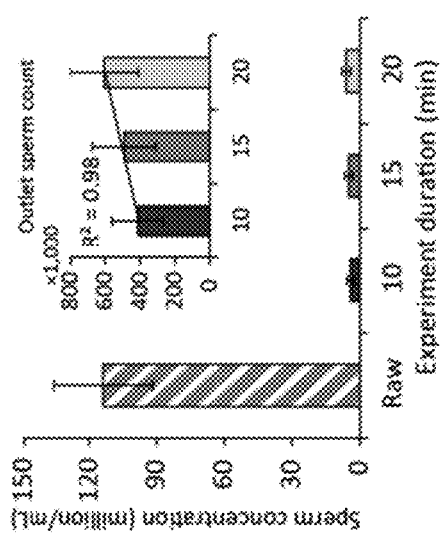
Figure 13C:
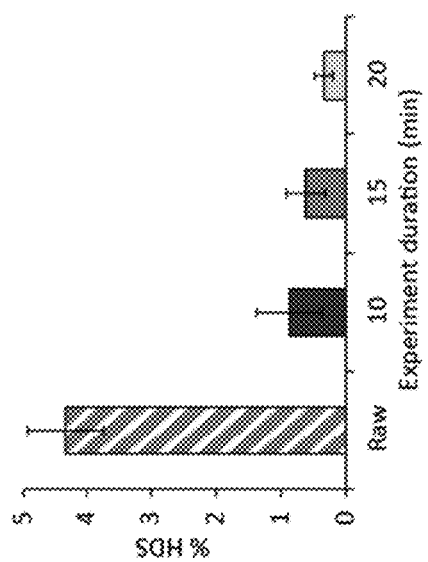

The influence of test duration on the concentration, count and DNA integrity of selected sperm was assessed for the 7.5 mm device with results plotted in FIGS. 13A-13C. The results indicate that with an average 113M sperm in the 1 mL sample introduced at the inlet, more than 410,000 were selected in 100 µL samples for the 10 min experiments. The number of selected sperm increases linearly to more than 490,000 and 600,000 sperm for 15 min and 20 min experiments ($R^2=0.98$), respectively (with corresponding collected concentrations of 4.91M/mL and 6.03M/mL). These selected sperm counts are more than sufficient for performance of IVF (~50,000) and certainly sufficient for ICSI protocols.

It is noteworthy, however, that the number of sperm collected is also a function of sample quality such that for male-factor infertility cases (i.e. oligozoospermia and asthenozoospermia) the proportion of sperm collected at the outlet is expected to be lower than from fertile men. As demonstrated here, both device length (FIG. 11A) and/or test run time (FIG. 13A) can be tuned to increase selected sperm counts as necessary. For example, providing a device with shorter microchannel lengths, and/or increasing the duration between introducing the sample into the inlet reservoir and collecting sperm from the outlet reservoir will tend to increase the number of sperm collected, while providing a device with longer microchannel lengths, and/or decreasing the duration between introducing the sample into the inlet reservoir and collecting sperm from the outlet reservoir will tend to decrease the number of sperm collected.

Selected human sperm DNA integrity values as quantified by DNA fragmentation index (% DFI) are shown in FIG. 13B. The respective selected sperm populations from the 10, 15, and 20 min experiments were lower than raw semen by 69% (10.9 to 3.37), 83% (7.29 to 1.26) and 81% (9.41 to 1.78), respectively (see Table 2 for details).

motile sperm in an array of 500 parallel channels filled with viscoelastic medium resembling that of the female reproductive tract. The device performs semen purification and high DNA integrity sperm selection simultaneously, providing clinically-relevant selected sperm numbers within 20 min. The level of sperm DNA and chromatin integrity obtained by microfluidic selection (% DFI range: 1-3% and % HDS range: 0.3-0.9%) has not been achieved with any other technique (Ng et al., 1992; Zini et al, 2000). The data also provide strong evidence that sperm chromatin and DNA integrity are closely related to rapid progressive sperm motility (characteristic feature of the outlet sperm). Taken together, these results demonstrate the presence of a sub-

TABLE 2

DFI and HDS results (n = 4)

| Parameters | 10 min | | 15 min | | 20 min | |
|---|---|---|---|---|---|---|
| (n = 4) | Raw | Outlet | Raw | Outlet | Raw | Outlet |
| Concentration × $10^6$/mL | | | | | | |
| Mean ± s.e (range) | 118 ± 18.9 (185-71) | 4.12 ± 1.47 (8.05-1.19) | 107 ± 22.7 (177-58) | 4.91 ± 1.81 (7.9-0.23) | 117 ± 24.4 (185-71) | 6.05 ± 1.97 (9.6-2.8) |
| % DFI | | | | | | |
| Mean ± s.e (range) | 10.9 ± 2.54 (16.68-2.67) | 3.37 ± 2.28 (10.18-0.55) | 7.29 ± 1.46 (12.37-3.83) | 1.26 ± 0.49 (2.24-0.64) | 9.41 ± 2.69 (14.18-2.67) | 1.78 ± 1 (3.89-0.44) |
| % HDS | | | | | | |
| Mean ± s.e (range) | 4.21 ± 0.77 (6.72-1.85) | 0.86 ± 0.51 (2.37-0.19) | 5.22 ± 0.44 (6.64-4.27) | 0.62 ± 0.3 (1.19-0.15) | 3.58 ± 0.59 (4.42-1.85) | 0.34 ± 0.14 (0.61-0.13) |

These data indicate that the device selects sperm with a significantly higher DNA integrity than the raw semen and suggest that 15 min is the preferred duration for selection of sperm with high DNA integrity. As shown in FIG. 13C, it was found that the % HDS in the respective selected sperm populations from the 10, 15, and 20 min experiments was lower than raw semen by 80% (4.21 to 0.86), 88% (5.22 to 0.62) and 91% (3.58 to 0.34), respectively (see Table 2 for details). These data seem to indicate that the 7.5 mm device may be capable of selecting sperm with a significantly higher chromatin compaction than in raw semen and suggest that the 20 min time is preferred.

Furthermore, both measures of DNA integrity, % DFI and % HDS, seem to indicate that the device may be capable of selecting populations of sperm with significantly higher DNA integrity. In the context of clinical application, the method further provides (1) sufficient selected sperm numbers for IVF and ICSI (e.g. >50,000); (2) fast processing (<20 min); and (3) a considerable simplification over current practices that require semen purification.

Further, analyses with human sperm regarding the duration suggest that the sperm concentration isolated was highest after 25 minutes (FIG. 13A); the DNA quality parameters were similar after 15 and 20 minutes (FIGS. 13B-13C). However, since the vitality of sperm decreases with time (data not shown), a duration of 15 minutes was determined to use for future experiments.

Overall, a simple microfluidic sperm selection approach has been developed based on the teachings herein. This sperm selection approach is capable of selecting high DNA integrity sperm from one milliliter of raw semen. The method leverages the boundary-following navigation of population of sperm with nearly intact chromatin and DNA integrity, and the ability to non-invasively select this population for use in ART.

In the context of clinical application, the simplicity and short duration of this selection process are also very useful features. Specifically, the one-step process replaces the previous multi-stage process which involves potentially damaging forces (e.g. centrifugation) and associated risk of iatrogenic sperm injury. The short duration minimizes oxidative stress. Although unverified, it is suspected that prolonging the experiments (beyond 20 min) may select sperm with enhanced maturity (higher chromatin compaction) at the expense of DNA damage as a result of oxidative stress.

Sperm donors with normal semen parameters (e.g. normal sperm chromatin and DNA integrity) were used. Further experiments with semen samples from infertile men, many of whom will have abnormal sperm parameters (e.g. poor concentration and poor motility) may be necessary to define the best device parameters for these subgroups of infertile men (primary concentration defect or primary motility defect). It is expected that the poorer sperm motility of samples from infertile men may require shorter device lengths and/or longer run times in order to attain sufficient sperm numbers for IVF. It is noteworthy, however, that many of these men may be candidates for ICSI (requiring only 10-30 sperm) so the lower percentage sperm recovery will not be an important adverse factor in such cases. Results here demonstrate that the simple device geometry and/or protocol can be tuned for patient-specific customization.

Sperm Quality—Human Sperm from Men with Infertility

Preliminary analyses of sperm sorted in a 2 hour time period using the apparatus and human sperm obtained from men with infertility showed a 40% improvement in morphology, a 74% improvement in motility, and a 58.4% improvement in % DFI as compared to the raw semen samples.

High-Throughput Separation Based on Motility and Wall-Swimming Behaviour

In another broad aspect, the embodiments described herein generally relate to a microfluidic sperm selection apparatus capable of separating sperm based on wall-swimming behaviour.

A one-step, high-throughput semen purification and spermatozoa selection device was used to select spermatozoa, showing that wall-swimming spermatozoa have a higher DNA integrity. This approach provides an improvement to clinical practices, avoiding currently used harmful techniques (Mortimer, 2000), and the inclusion of an additional fertility parameter, namely wall-swimming behaviour. It is expected that this selection of spermatozoa will lead to a higher rate of pregnancies with positive outcomes. The analysis provides further insights into the wall-swimming behaviour of spermatozoa which is of high interest for reproductive biologists, microfluidic researchers, and basic researchers studying cell swimming phenomenon.

Figure 14A:
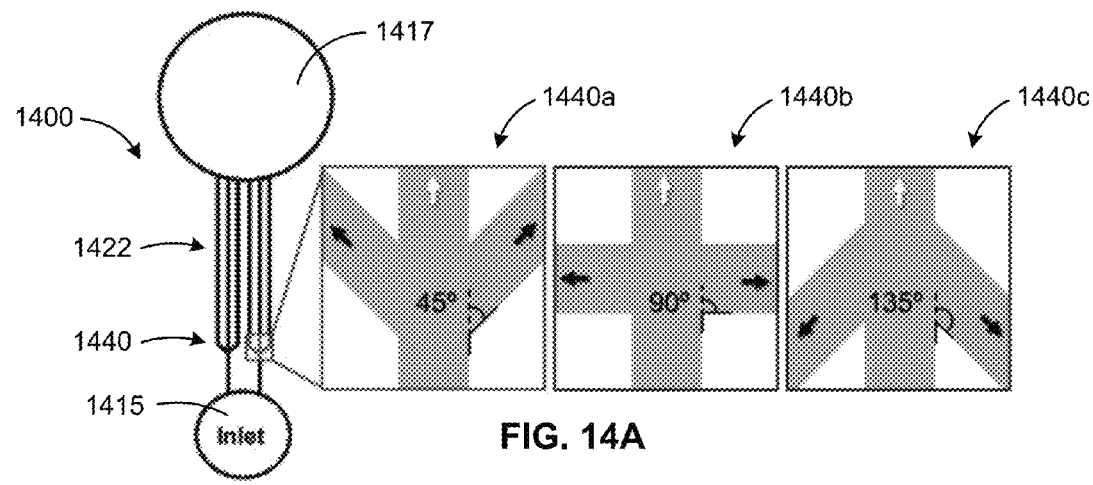
FIG. 14A is a top schematic view of a microfluidic device with three different junction designs.

Experimental Results:

To assess spermatozoa selection potential based on wall-swimming behaviour, as shown in FIG. 14A a microfluidic device 1400 was fabricated PDMS with a glass bottom. In this device, an inlet reservoir 1415 was in fluid communication with an outlet 1417 via a plurality of microchannel paths 1422, each path comprising a junction 1440. To select spermatozoa based solely on spermatozoa motility, fluid flow is prevented in the device by implementing dead-end chambers at the end of the microchannels. Spermatozoa swam from the inlet reservoir 1415 into the main channel until they reached a junction 1440. Spermatozoa were identified as straight-swimmers (SS) if they passed straight through the junction or wall-swimmers (WS) if they followed the channel wall and swam into the left or right side channel. Three different designs with variable angles at the junction (45°, 90°, 135°, shown enlarged as 1440a, 1440b, and 1440c) were used in order to determine the effect of the junction angle on selection efficiency (FIG. 14A). Numbers of SS and WS spermatozoa were assessed by manual counting.

Figure 14B:
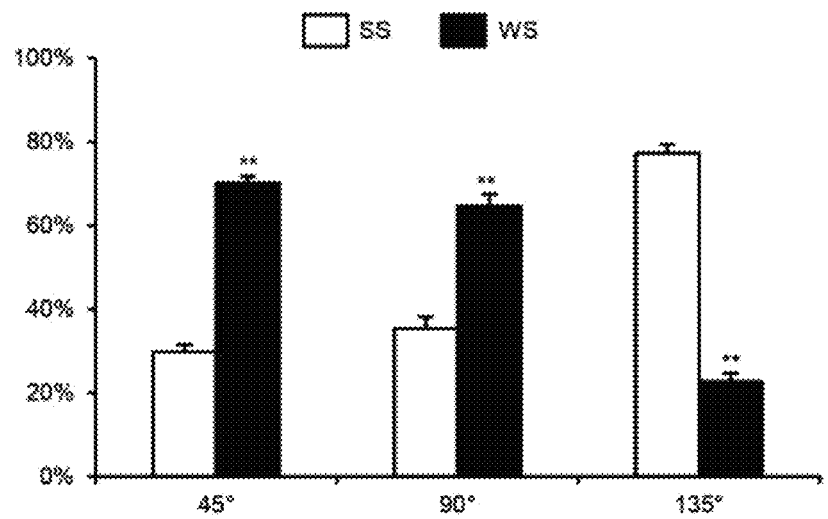
FIG. 14B is a chart of a distribution of straight-swimmers (SS) and wall-swimmers (WS) for the three different junction designs of FIG. 14A.

The results in FIG. 14B demonstrate that 70.1±1.6% and 64.6±2.8% of bovine spermatozoa may be identified as WS in comparison to 29.9±1.6% and 35.4±2.8% SS in the designs with 45° and 90° angles, respectively. Fewer WS were selected when an angle of 135° was included at the junction since the numbers of WS significantly decreased to 22.7±2.1% and the numbers of SS increased to 77.3±2.1%. (n=12 independent experiments, mean±s.e.m., P values were determined by two-sided unpaired Student's t-test with unequal variances showing significant differences between SS and WS; *P<0.0005, P<0.005, *P<0.05.)

Figure 14C:
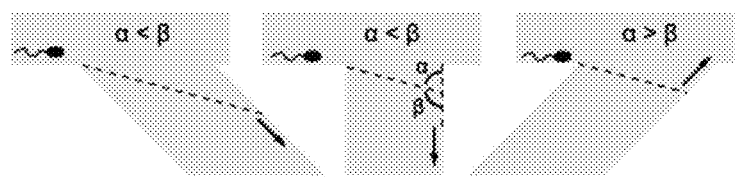
FIG. 14C is a top schematic view showing spermatozoa departure from channel corners.

It was seen that spermatozoa swam against the opposite side channel wall where they are expected to turn towards the side with the obtuse angle, as shown in FIG. 14C (arrows indicate swimming direction after deflection from opposite channel wall). Therefore, side channel angles <105° (=15°+ 90°), as in the case of the 45° and 90° designs, will result in the spermatozoa swimming into the side channel, while angles >105°, here represented by the 135° design, redirect the spermatozoa into the main channel. These results suggest that angles <105° may be used in order to select wall-swimming spermatozoa. Further, this proof-of-concept experiment demonstrates that selection of bovine spermatozoa based on wall-swimming behaviour may be a suitable way to divide spermatozoa from a semen sample into different subpopulations.

In order to test if spermatozoa orient along the device surface depending on the material, microfluidic devices were fabricated (1) with a glass bottom and PDMS top, (2) entirely of PDMS, and (3) with a PDMS bottom and glass top. The attraction of bovine spermatozoa towards a glass surface was discussed half a century ago (Rothschild, 1963). The Rothschild study, however, analyzed spermatozoa in a drop on a glass surface, not offering the spermatozoa an alternative solid surface. Confining spermatozoa between two solid surfaces is therefore a new approach to analyzing spermatozoa swimming behaviour according to the teachings herein. To determine the ratio of left-swimmers (LS) and right-swimmers (RS), all three devices were tested for spermatozoa swimming to the left and right. SS were not included in the analysis in order to determine if a significant difference between LS and RS exists.

Figure 15A:
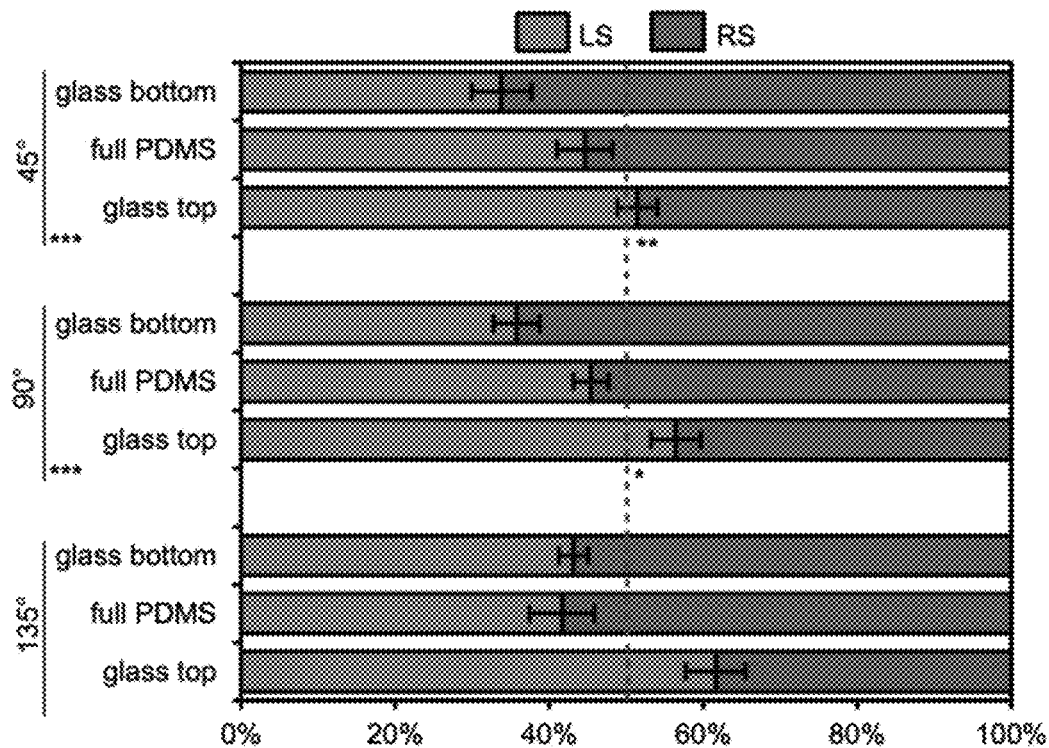
FIG. 15A is a chart of percentages of spermatozoa identified as left-swimmers (LS) and right-swimmers (RS) in devices fabricated from different materials and containing different designs.

The experiments with the 45° angle and glass bottom revealed a significant preference of WS bovine spermatozoa to swim into the right-hand channels (66.2±3.9% RS vs. 33.8±3.9% LS), illustrated in FIG. 15A (the dashed line indicates 50% mark). P values determined by two-factor ANOVA show if significant differences exist between LS and RS (below bars) and between different materials (below axis labels).

The preference to swim to the right decreases in the full PDMS device, indicated by a slightly higher percentage of RS than LS spermatozoa (55.4%±4.2% RS vs. 44.6±4.2% LS). When using the glass-top device, however, the ratio shifted towards more LS (51.4±1.9%) than RS (48.6±1.9%), but with a lower imbalance than in the glass-bottom device. The same distribution was also observed in the 90° design, confirming the former findings that angles between 45° and 90° result in comparable spermatozoa selection. Although a similar trend could also be observed in the 135° design, the differences between RS and LS were not significant. These findings suggest that a high percentage of spermatozoa prefer to swim along the glass surface and then to the right. In cases where the glass surface forms the device bottom, more spermatozoa are RS than LS. Inversion of the setup for the case with glass surface on top leads to more LS than RS, indicating that this effect is dependent on the position of the glass surface. The results show that the attraction of spermatozoa to solid surfaces is not equal for every material, thereby providing new information on spermatozoa swimming behaviour that can be employed for spermatozoa selection. Further, the findings of left-right swimming asymmetry with a right-swimming preference of spermatozoa are an uninvestigated phenomenon and this study provides insights into a potential role of the left-right axis in reproductive biology. Future studies may reveal if the left-right asymmetry has a similar impact on reproduction as it has on embryonic development (Raya and Izpisúa Belmonte; 2006).

Figure 15B:
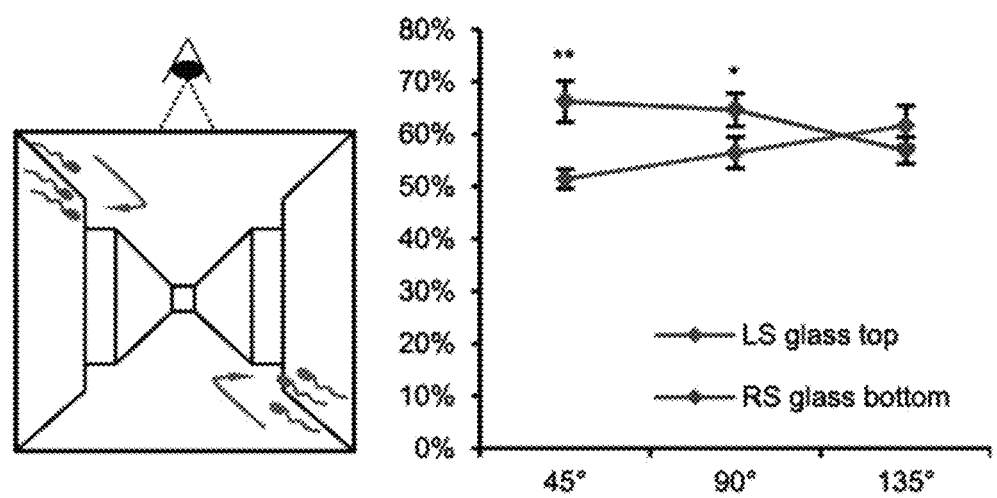
FIG. 15B is a comparison of spermatozoa swimming to the left-hand side or right-hand side dependent on a top or bottom glass-surface.

The possible influence of gravity on the swimming behaviour of spermatozoa was examined. Theoretical considerations have been published on the influence of gravity (Katz and Pedrotti, 1997) and experimental data is available supporting the hypothesis of gravitaxis in bovine and human spermatozoa (Roberts, 1972; Makler et al., 1993). Contradicting data indicating that gravity has no effect on spermatozoa swimming has also been published (Winet et al., 1984). In order to get new insights into spermatozoa gravitaxis, the ratios of spermatozoa swimming along the glass surface into the right-hand channels were compared. As demonstrated in FIG. 15B, these were the spermatozoa identified as RS in the glass-bottom device, and the spermatozoa identified as LS in the glass-top device. Comparison of these two populations in the 45° design shows that significantly more RS (66.2±43.9%) could be detected in the glass-bottom device than LS (51.4±1.9%) in the glass-top device. A similar, but lower effect was observed in the 90° design with 64.6±3.2% RS and 56.4±3.0% LS, but no significant difference could be detected in the 135° design (n=12 independent experiments, mean±s.e.m., P values were determined by two-sided unpaired Student's t-test with unequal variances; *P<0.0005, P<0.005, *P<0.05). These results demonstrate that under the effect of gravity, spermatozoa tend to swim close to the device bottom. This strengthens the hypothesis that spermatozoa exert gravitaxis.

Figure 16A:
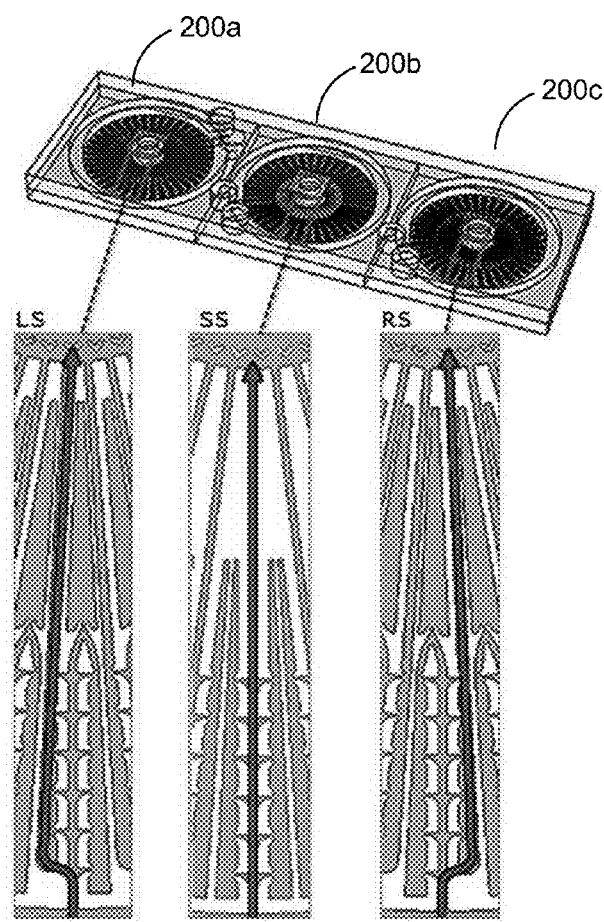
FIG. 16A is a schematic of a high-throughput microfluidic device showing top views of the channel configurations to select spermatozoa based on left, straight, or right wall-swimming behaviour.

The effects of wall-swimming behaviour on the vitality and DNA integrity of selected spermatozoa were also investigated. A plurality of one-step, high-throughput semen purification and spermatozoa selection apparatus without flow were fabricated entirely of PDMS, with each apparatus having one of three microchannel path designs (e.g. 200a, 200b, and 200c as shown in FIG. 16A). In each of these microchannel path designs, a central path leads from a path inlet adjacent an inlet reservoir, and six junctions were provided along the central path, each junction having a central path and two approximately perpendicular side channels leading into left and right elongate side chambers substantially parallel to the central path. In the path design shown in 200b, the central path leads to the outlet reservoir, and the side chambers were effectively dead-ends. In the design shown in 200a, the left side chamber led to the outlet reservoir, while the central path and the right side chamber were effectively dead-ends. In the design shown in 200c, the right side chamber led to the outlet reservoir, while the central path and the left side chamber were effectively dead-ends.

Figure 16B:
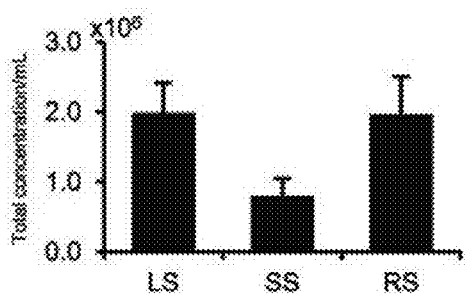
FIG. 16B is a chart of bull spermatozoa concentration collected from each of the outlets for the left-swimmers (LS), straight-swimmers (SS), and right-swimmers (RS)
Figure 16C:
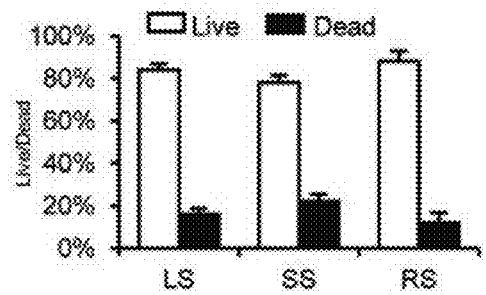
FIG. 16C is a chart of percentage vitality of the bull spermatozoa collected from each of the outlets for the LS, SS, and RS spermatozoa.

An angle of 90° was used for the side channels since the preliminary experiments indicated such an angle to be suitable to employ sperm deflection. In addition, a curvature of 200 μm was used to aid sperm in continuously following the wall (Denissenko et al., 2012). The device selected spermatozoa from 200 μL of raw semen based on their preference to be LS, SS, or RS, while dead spermatozoa and debris remained in the inlet. The bovine spermatozoa concentration results at the outlet, as shown in FIG. 16B, indicate that the concentrations of spermatozoa collected from the LS ($1.96\pm0.45\times10^6$/mL) and RS ($1.94\pm0.56\times10^6$/mL) outlets were higher than the concentration of spermatozoa collected from the SS ($0.77\pm0.78\times10^6$/mL) outlet (n=14 independent experiments, mean±s.e.m., P values were determined by a single analysis of variance; *P<0.0005, P<0.005, *P<0.05). These differences in concentration raise the question of whether vitality differs between the spermatozoa exhibiting wall-swimming behaviour and those that do not exhibit such behaviour. The bovine vitality results, as shown in FIG. 16C, show that there is no statistically significant difference in the vitality of the spermatozoa selected using wall-swimming behaviour (83.64±2.72% LS, 77.62±3.38% SS, 87.86±4.76% RS) (n=14 independent experiments, mean±s.e.m., P values were determined by a single analysis of variance; *P<0.0005, P<0.005, *P<0.05). These experiments yielded a ratio of spermatozoa displaying left-right swimming asymmetry consistent with the preliminary experiments previously discussed, introducing wall-swimming behaviour as a powerful tool for microfluidic spermatozoa selection.

Figure 17B:
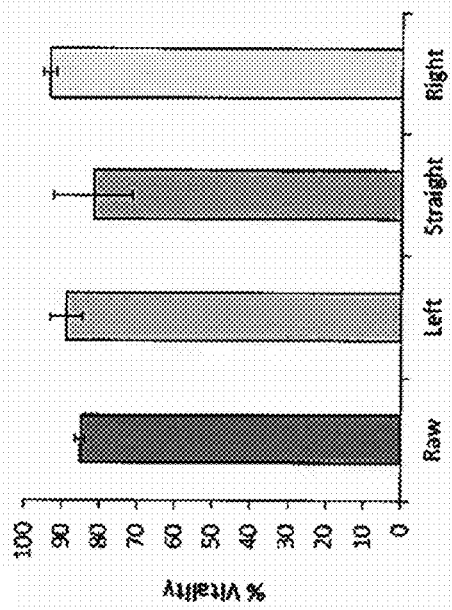
FIGS. 17A-17D are charts showing concentration, vitality, and DNA assessment of human spermatozoa sorted by wall-swimming behaviour.

The concentration and vitality results of the human spermatozoa selected using wall-swimming behaviour (FIGS. 17A and 17B) display the same trends as the bovine results (FIGS. 16B and 16C). When comparing the concentration and vitality for the LS, the bovine results are $1.96\pm0.45\times10^6$/mL and 83.6±2.72%, which is similar to the human results of $1.55\pm0.43\times10^6$/mL and 88.81±4.26%. This provides a strong foundation for using bovine spermatozoa as a model for swimming behaviour of human spermatozoa. Comparison of the vitality of the spermatozoa selected by the microfluidic device shows that there is no significant compromise in vitality of the spermatozoa selected using wall-swimming behaviour since 88.81±4.26% of LS, 81.87±10.48% of SS, and 93.58±1.63% of RS were alive, in comparison to the 85.20±1.18% alive in the raw semen sample (FIG. 17B).

Figure 17D:
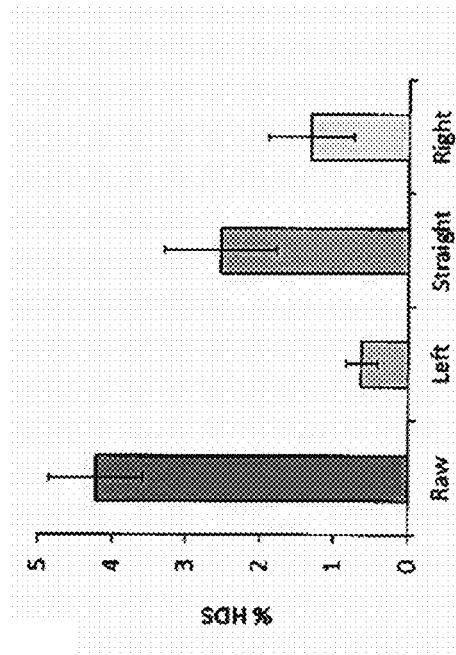
Figure 17A:
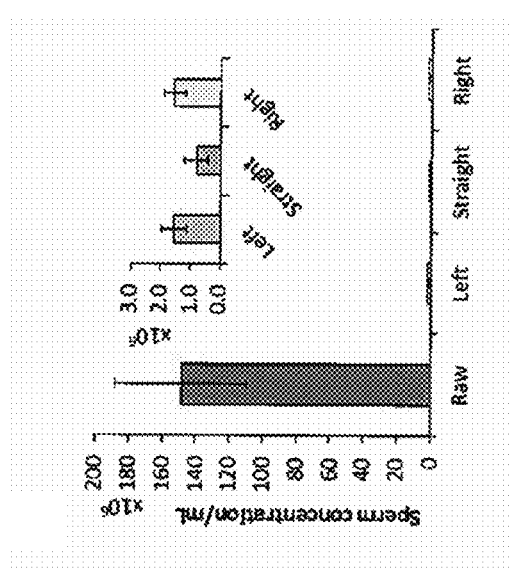
Figure 17C:
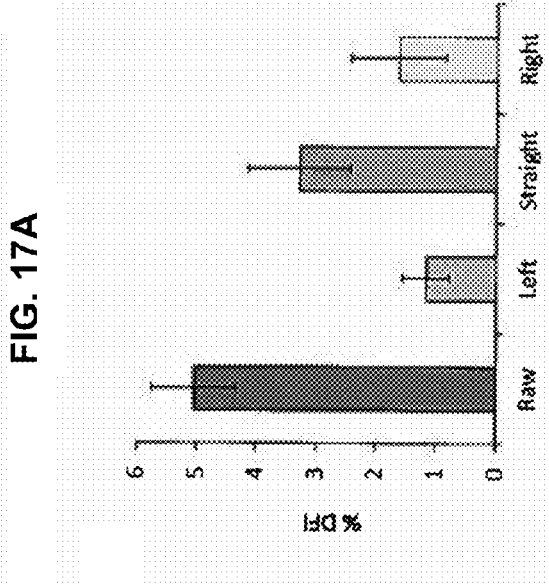
Figures 18A, 18B:
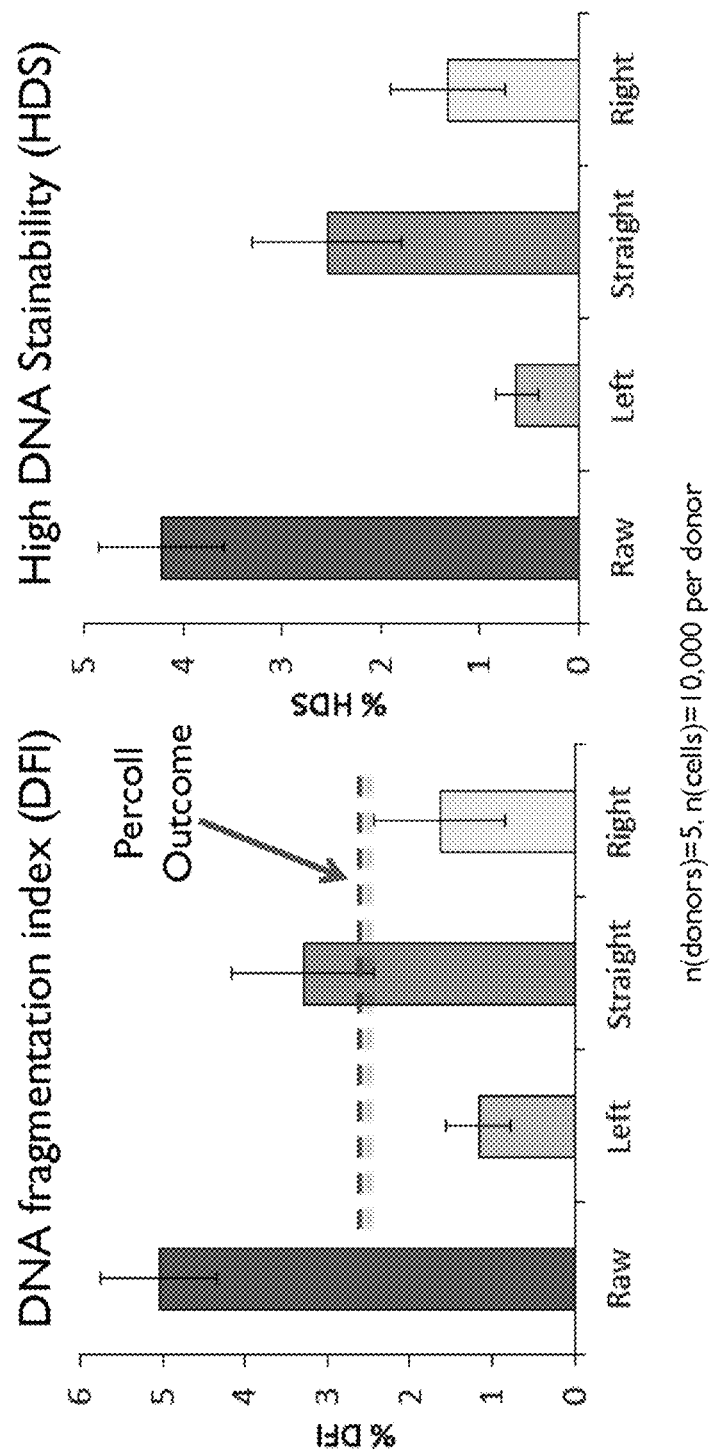
FIGS. 18A-18B are charts showing a percentage DNA Fragmentation Index (DFI) and high DNA stainability (% HDS) of the spermatozoa collected from the outlets as compared to the raw semen sample relative to a Percoll Outcome.

The results of the sperm chromatin structure assay (SCSA) of the human spermatozoa selected using left-right swimming asymmetry and the raw semen samples are provided in FIGS. 17C and 17D (n=5 independent experiments, mean±s.e.m, P values were determined using a two-sided t-test comparing to the raw sample (control); *P<0.0005, P<0.005, *P<0.05.). The DNA fragmentation index (DFI) shows the percentage of cells that have DNA damage and the high DNA stainability (HDS) shows the percentage of cells that are immature. The results for the DFI and HDS show that the spermatozoa selected by the microfluidic device have lower % DFI (LS 1.16±0.39%, SS 3.30±0.86%, RS 1.63±0.79%) and % HDS (LS 0.62±0.22%, SS 2.54±0.76%, RS 1.32±0.57%) than the raw semen (% DFI: 5.04±0.70%, % HDS: 4.21±0.63). Looking exclusively at the results from the spermatozoa selected using wall-swimming behaviour, it first appears that the LS device yields better % DFI and % HDS than the RS and SS. These results, however, would need to be further explored in order to better understand whether differences exist between the LS and RS. A result that is noteworthy is the improvement of DNA integrity of the spermatozoa selected using microfluidics and left-right swimming asymmetry in comparison to the traditional technique of Percoll gradient centrifugation. Previous research has shown that Percoll preparation is capable of selecting spermatozoa with half the DFI of the raw semen sample DFI (De Lamirande et al., 2012). To compare to such results, the % DFI of the raw semen used in this study would need to drop from approximately 5% to 2.5%. The % DFI for the LS (1.16±0.39%) and the RS (1.63±0.79%) are noticeably below 2.5%, indicating that the selection of LS and RS spermatozoa can yield better results than the traditional Percoll gradient centrifugation (e.g. see FIG. 18).

Altogether, left-right swimming asymmetry of spermatozoa is influenced by a complex interaction of several physical factors, like gravity, surface material, and channel geometry. The variation of these factors allows the separation of spermatozoa into different subpopulations. The vitality and DNA integrity results of the spermatozoa selected appear to have three implications: (1) the microfluidic device does not cause DNA damage to the spermatozoa, (2) the spermatozoa selected by the microfluidic device have a significantly lower incidence of DNA damage than the raw semen, and (3) left-right swimming asymmetry can be utilized as an instrument for spermatozoa selection with high DNA integrity comparable or better than using the Percoll gradient centrifugation preparation.

Experimental Procedure

Devices for the first part of the study were made (1) from PDMS with a glass bottom, (2) entirely of PDMS, or (3)

from PDMS with a glass top. Standard soft lithography techniques were used for fabrication. Prior to use, devices were filled with high viscous buffer containing 1 mg/mL Hyaluronic Acid. A temperature of 37° C. was maintained for the duration of the experiment. Immediately before injection into the microfluidic device, frozen bovine spermatozoa were thawed at 37° C. and stained with SYBR14 (LIVE/DEAD Sperm Viability Kit, Molecular Probes, USA) according to the manufacturer's instructions. Then 2 μL of the stained sample were injected into the device. Videos 5-minute in length showing fluorescent spermatozoa swimming in the junctions of the device were taken. The device design allowed capturing of two videos simultaneously. Counting of spermatozoa was performed manually after the experiment.

The high-throughput device for the second part of the study was fabricated using soft lithography techniques and filled with high viscous buffer containing 5 mg/mL methyl cellulose. A temperature of 37° C. was maintained for the duration of the experiment. Frozen bovine semen was thawed and human semen was obtained and treated as previously published (Nosrati et al., submitted 2013). An aliquot of 0.20 mL of semen was injected into the inlet ring using a plastic syringe. The devices were left undisturbed for 15 minutes, the outlet cover was then removed, and the spermatozoa extracted from the outlet using a pipette (Nosrati et al., submitted 2013). The spermatozoa concentration was determined by manually counting the cells in a haemocytometer. For the bovine experiments used to validate the microfluidic design, the vitality was assessed by counting the live and dead cells stained using the LIVE/DEAD Sperm Viability Kit. New devices were used for each experiment. The vitality of human sperm was determined using established staining protocols (De Lamirande et al., 2012), and the DNA integrity was assessed using existing SCSA protocols (Zini et al., 2002).

Application:

Overall, the analyses discussed above suggest that wall-swimming behaviour of spermatozoa may be used as a potential fertility parameter and predictor for DNA integrity. It shows that spermatozoa can be selected using microfluidic geometries with angles less than 105° and that depending on the surface material, spermatozoa show a left-right swimming asymmetry with a preference to swim on the right.

Also, experiments on human sperm revealed a slightly higher preference of sperm to swim to the right-hand side than to the left-hand side, as seen in earlier experiments with bull semen in a full PDMS device (FIG. 15A, FIG. 17A). Lowest concentrations appear to have been revealed for the straight channels. Similar results can be seen for the analysis of vitality (FIG. 17B). Sperm swimming to the right-hand side show the highest percentage of living sperm, followed by the population swimming to the left-hand side. Straight-swimming sperm, however, show a lower percentage of living sperm than the raw semen sample. The DFI and HDS parameters are significantly reduced after separation based on wall-swimming behaviour with sperm swimming to the left-hand side showing highest improvement in DNA integrity of separated sperm. Right-handed swimmers show slightly less improved DNA integrity than left-swimmers. However, the improvement in DNA integrity of straight-swimming sperm is the lowest in comparison to the two other subpopulations (FIGS. 17C-17D). This makes separation for left-swimming sperm a promising approach.

As noted above, examples of microfluidic sperm selection apparatus (e.g. 200a, 200b, and 200c) capable of separating sperm based on wall-swimming behaviour are shown in FIG. 16A. While generally similar to apparatus 100 described above, in apparatus 200, a microchannel network 222 is designed in order to sort sperm using wall-swimming behaviour: each separation unit illustrated in FIG. 16A contains three main microchannels that are cross-linked by six perpendicular channels. It will be appreciated that other configurations of microchannels and cross-channels may be provided.

Corners in this channel network may be rounded so that sperm are able to continuously follow the wall around the corner. For example, a curvature of 200 μm may be applied to the corners. One of the main channels leads into the outlet reservoir; the other two main channels direct motile sperm into a dead-end (e.g. a collection chamber or trap). This means that their preferences to swim to a specific side will guide sperm either into the outlet reservoir (if it is the preferred side) or the dead end/trap (if it is not the preferred side).

Figure 19:
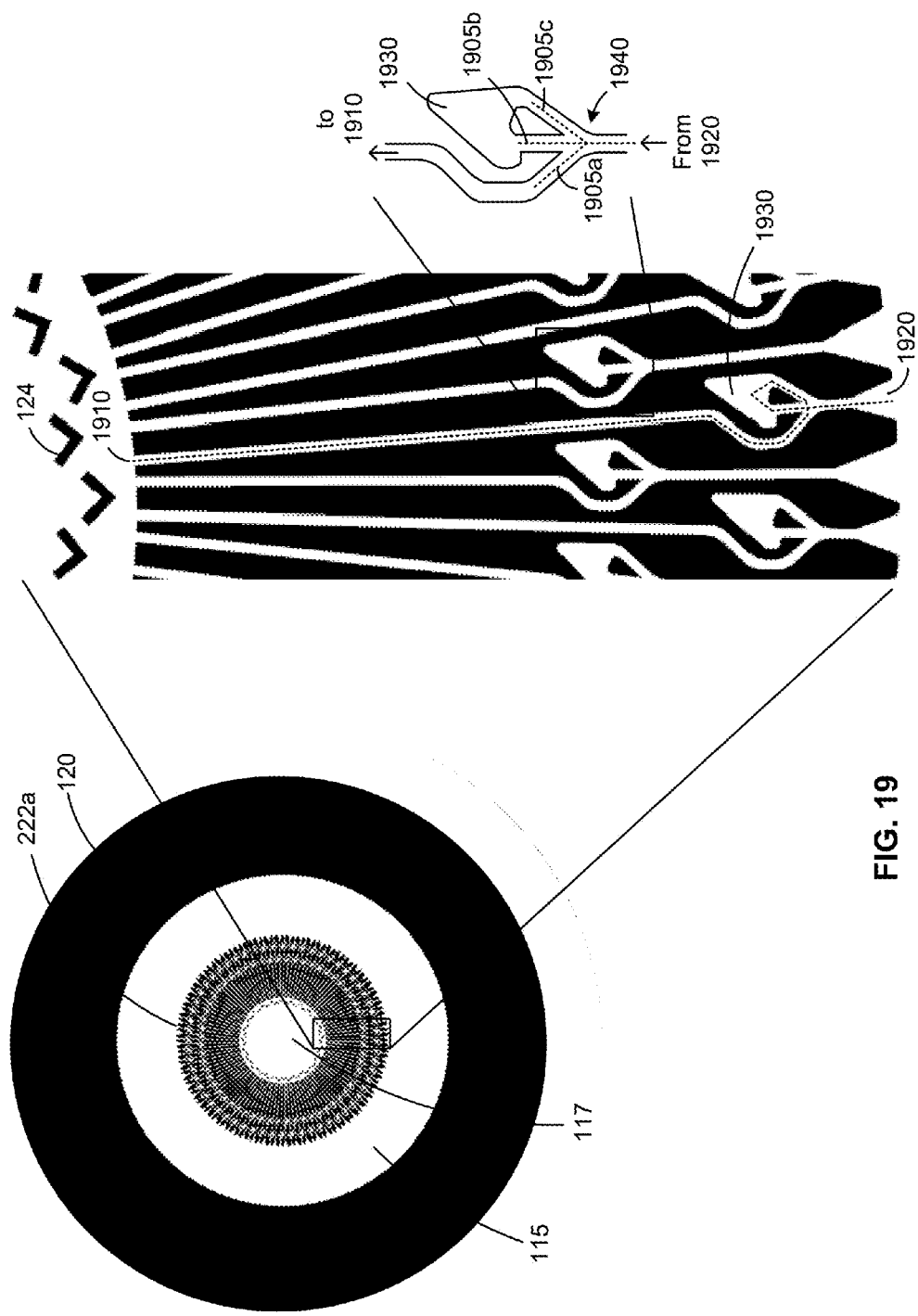
FIG. 19 is a top view, partially enlarged, of an alternate array of microchannels in accordance with another example embodiment.
Figure 20:
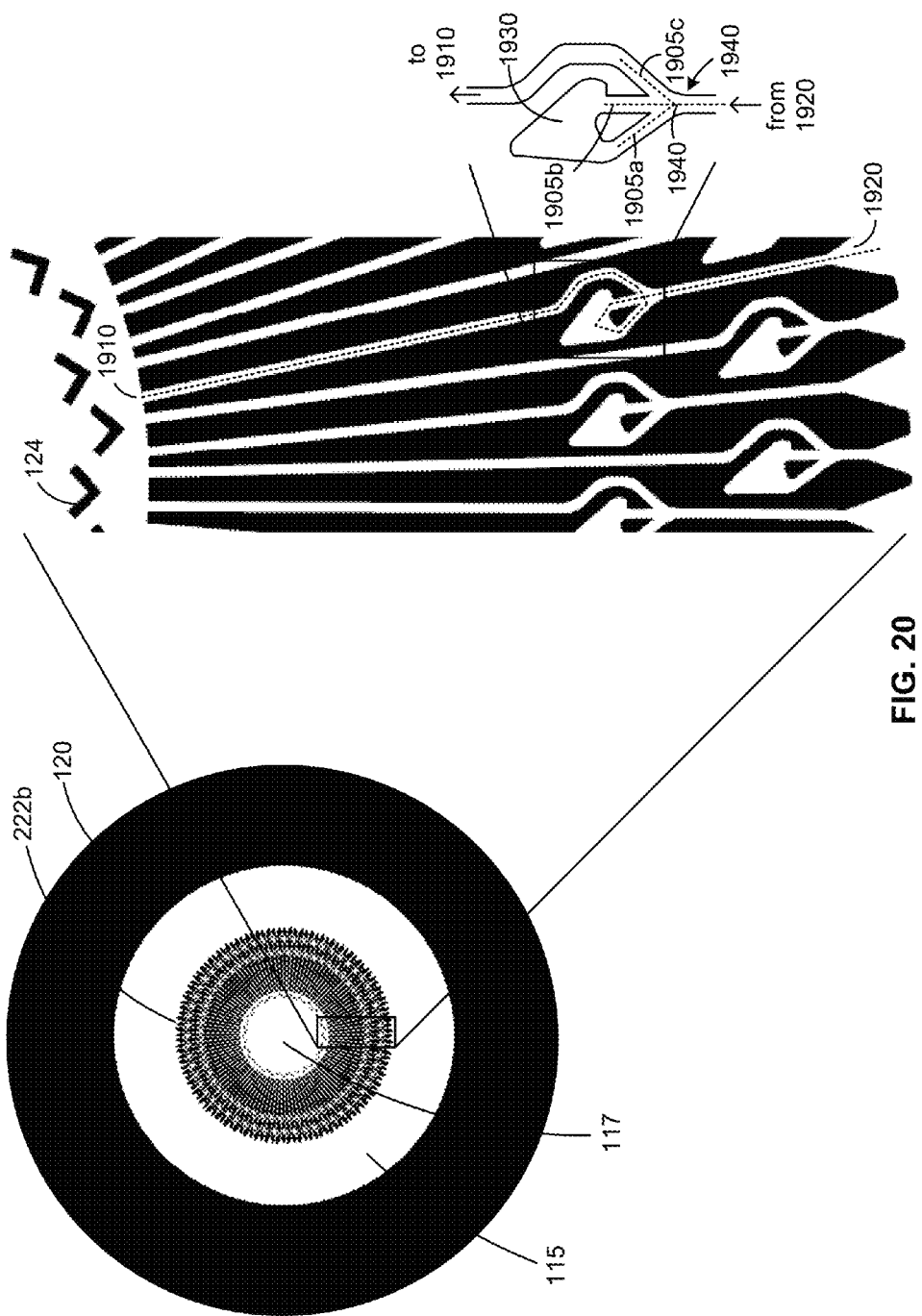
FIG. 20 is a top view, partially enlarged, of an alternate array of microchannels in accordance with another example embodiment.
Figure 21:
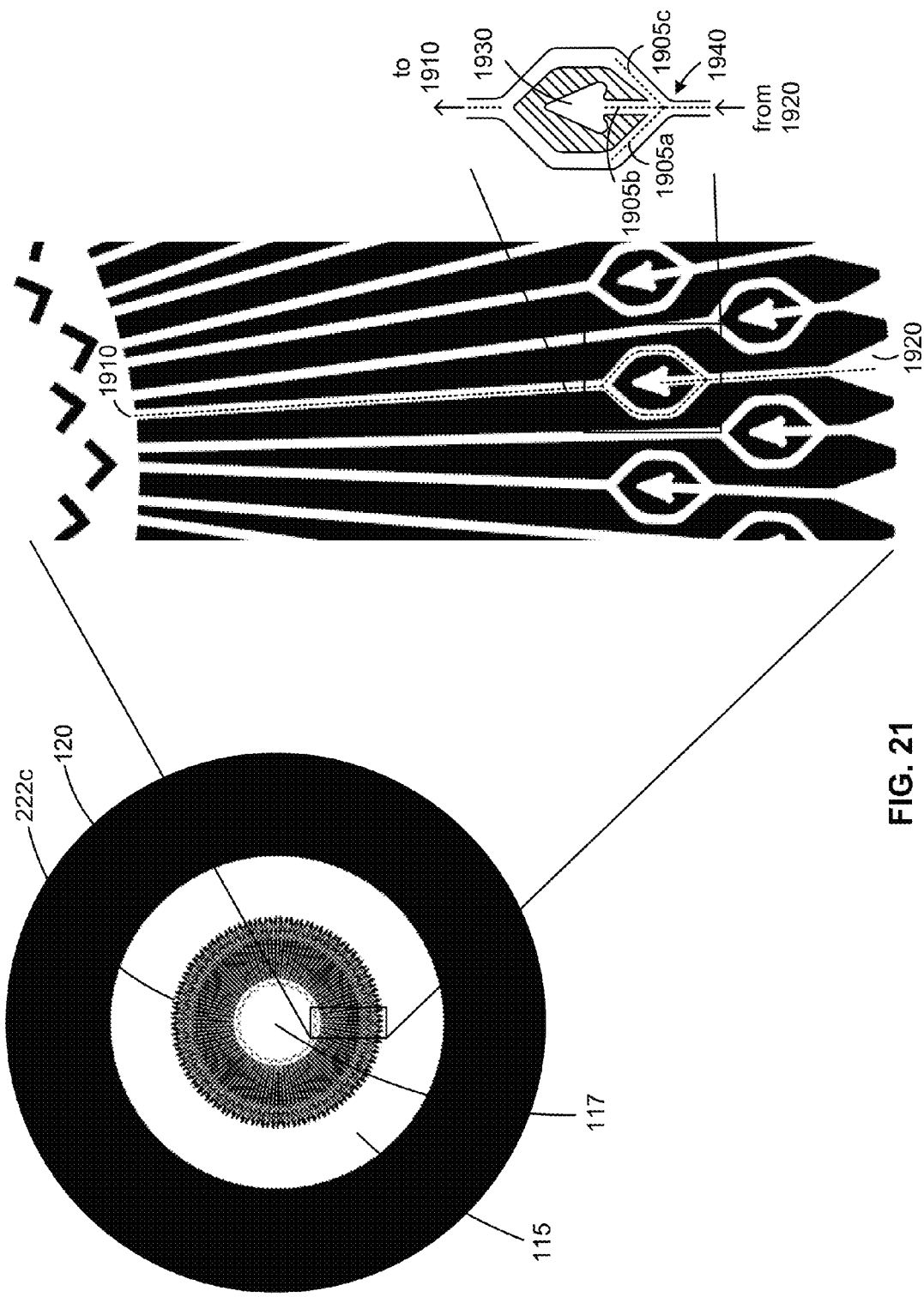
FIG. 21 is a top view, partially enlarged, of an alternate array of microchannels in accordance with another example embodiment.

Other example embodiments of microchannels designed to order to sort sperm using wall-swimming behaviour are shown in FIGS. 19-21.

In the example shown in FIG. 19, which is designed to select left-swimmers, microchannel path 1905 comprises a path inlet 1920 adjacent the inlet reservoir 115, a path outlet 1910 adjacent the outlet reservoir 117, and a junction 1940 located between the path inlet and the path outlet for directing a portion of sperm that enter the path inlet towards the outlet reservoir. In this example, sperm that tend to swim along a left wall will be guided along path 1905a towards the outlet reservoir 117, while sperm that tend to swim straight or along a right wall will be guided along path 1905b and 1905c, respectively, each of these paths leading towards a collection chamber 1930 (or other effective dead end). Accordingly, sperm that enter the straight or right path are directed away from the outlet reservoir 117, and thus will not be among the sperm collected from the outlet reservoir 117.

In the example shown in FIG. 20, which is designed to select right-swimmers, when encountering junction 1940, sperm that tend to swim along a right wall will be guided along path 1905c towards the outlet reservoir 117, while sperm that tend to swim straight or along a left wall will be guided along paths 1905b and 1905c, respectively, towards collection chamber 1930. In the example shown in FIG. 21, which is designed to select straight-swimmers, sperm that tend to swim straight will be guided towards a collection chamber, while sperm that tend to swim along a right wall or along a left wall will be guided towards the outlet reservoir 117.

It will be appreciated that in alternative embodiments, variations may be made to the example microchannel paths 222 and/or 222a-c. For example, variant designs may incorporate one or more dividing wall members (similar to dividers 126 shown in FIG. 4), one or more gradual (and/or distinct) tapering regions between the path inlet and the path outlet, and/or more than one collection chamber (or other effective dead-end) per path inlet.

Example dimensions for the microchannel paths in microchannel array 222 (and/or in microchannel arrays 222a-c) are shown in Table 3.

TABLE 3

Dimensions of apparatus 200 for high-throughput separation based on motility and wall-swimming behaviour.

| Device II | Width | Height | Length | Radius |
|---|---|---|---|---|
| Inlet | 4.5-7.5 mm | 1.45 mm | n.a. | n.a. |
| Channel | 100-600 μm | 50-75 μm | 6.5-7.5 mm | n.a. |

TABLE 3-continued

Dimensions of apparatus 200 for high-throughput separation based on motility and wall-swimming behaviour.

| Device II | Width | Height | Length | Radius |
|---|---|---|---|---|
| Channel (to end of trap) | 100-300 μm | 50-75 μm | 1.4-6 mm | n.a. |
| Outlet | n.a. | 0.8 mm | n.a. | 5.0-6.0 mm |

When the apparatuses and methods described herein are applied to intracytoplasmic sperm injection (ICSI), a longer microchannel length in the radial network may be used. The device can then be run for a shorter duration in order to have a highly selective quality of sperm at the device outlet which would then be manually selected by embryologists for ICSI. If desired, the outlet can be monitored under a microscope in order to manually select the first sperm to exit the microchannel observed.

Various embodiments of systems, apparatuses and methods that can be used to separate sperm have been described herein by way of example only. For example, the apparatuses and methods described herein may be used for the separation of other cell types, such as (but not limited to) self-propelling prokaryotes after minor design changes, but also eukaryotes that migrate due to internal or external cues, or cell types with specific surface properties (it will be appreciated that functionalization of the microfluidic device would have to be made accordingly) For example, alternative microchannel networks may be provided in order to: i) guide the cells (chemotaxis); ii) bind the cells to one or more surfaces of the apparatus (e.g. surfaces in the inlet reservoir, the outlet reservoir, and/or the microchannel network); and/ or iii) modify the migration ability of cells by inducing a phenotypic transition (e.g. epithelial-mesenchymal-transition). Various modifications and variations may be made to all of the example embodiments described in accordance with the teachings herein without departing from the spirit and scope of the embodiments, which is limited only by the appended claims which should be given the broadest interpretation consistent with the description as a whole.

REFERENCES

A. Agarwal, T. M. Said, *Hum. Reprod. Update* 2003, 9, 331-345.
A. Aharoni, K. Thieme, C. P. C. Chiu, S. Buchini, L. L. Lairson, H. Chen, N. C. J. Strynadka, W. W. Wakarchuk, S. G. Withers, *Nat. Methods* 2006, 3, 609-614.
A. Ahmadi, S-C. Ng, *J. Exp. Zool.* 1999, 284, 696-704.
A. Souza Setti, R. C. Ferreira, D. Paes de Almeida Ferreira Braga, R. de Cássia Sávio Figueira, A. Iaconelli, E. Borges, *Reprod. BioMed. Online* 2010, 21, 450-455.
A. T. Ohta, M. Garcia, J. K. Valley, L. Banie, H.-Y. Hsu, A. Jamshidi, S. L. Neale, T. Lue, M. C. Wu, *Lab Chip* 2010, 10, 3213-3217.
A. Zini, A. Finelli, D. Phang, K. Jarvi, *Urology* 2000, 56, 1081-1084.
A. Zini, M. Sigman, *J. Androl.* 2009, 30, 219-229.
A. Zini, R. Bielecki, D. Phang, M. T. Zenzes, *Fertil. Steril.* 2001, 75, 674-677.
A. Zini, V. Mak, D. Phang, K. Jarvi, *Fertil. Steril.* 1999, 72, 496-499.
Ainsworth C (2005). The secret life of sperm. *Nature* 436:770-771.
Aitken, R. J., De Iuliis, G. N., McLachlan, R. I. Biological and clinical significance of DNA damage in the male germ line. *J. Androl.* 32, 46-56 (2009).
B. Balaban, K. Yakin, C. Alatas, O. Oktem, A. Isiklar, B. Urman, *Reprod. BioMed.* Online 2011, 22, 472-476.
B. S. Cho, T. G. Schuster, X. Zhu, D. Chang, G. D. Smith, S. Takayama, *Anal. Chem.* 2003, 75, 1671-1675.
Balakrishnan T R, Fernando R (1993). Infertility among Canadians: an analysis of data from the Canadian Fertility Survey (1984) and General Social Survey (1990). In: *The Prevalence of Infertility in Canada: Research Studies of the Royal Commission on New Reproductive Technologies*. Ottawa: Minister of Supply and Services Canada, 107-162.
Boivin J, Bunting L, Collins J A, Nygren K G (2007). International estimates of infertility prevalence and treatment-seeking: potential need and demand for infertility medical care. *Hum Reprod* 22:1506-1512.
Boivin J, Bunting L, Collins J A, Nygren K G (2009). Reply: International estimates on infertility prevalence and treatment seeking: potential need and demand for medical care. *Hum Reprod* 24:2380-2383.
Boivin, J., Bunting, L., Collins, J. A., Nygren, K. G. International estimates of infertility prevalence and treatment-seeking: Potential need and demand for infertility medical care. *Hum Reprod.* 22, 2800-2800 (2007).
Burger H G, Baker H W G (1987). The treatment of infertility. *Ann Rev Med* 38: 29-40.
Bushnik T, Cook J L, Yuzpe A A, Tough S, Collins J (2012). Estimating the prevalence of infertility in Canada. *Hum Reprod* 27(3):738-46.
C. Ainsworth, B. Nixon, R. J. Aitken, *Hum. Reprod.* 2005, 20, 2261-2270.
C. Coughlan, W. L. Ledger, *Obstet. Gynaecol. Reprod. Med.* 2008, 18, 300-306.
Collins J A (2002). An international survey of the health economics of IVF and ICSI. *Human Reproduction Update* 8(3):265-277.
Cooper T G, Noonan E, von Eckardstein S et al. (2010). World Health Organization reference values for human semen characteristics. *Hum Reprod Update* 16(3):231-45.
D. Le Lannou, Y. Blanchard, *J. Reprod. Fertil.* 1988, 84, 551-556.
D. P. Evenson, in *Spermatogenesis: Methods and Protocols* (Eds.: D. T. Carrell, K. I. Aston), Humana Press, New York, 2013, pp. 147-164.
D. P. Evenson, K. L. Larson, L. K. Jost, *J. Androl.* 2002, 23, 25-43. D. Sakkas, *Fertil. Steril.* 2013, 99, 1023-1029.
D. Sakkas, G. C. Manicardi, M. Tomlinson, M. Mandrioli, D. Bizzaro, P. G. Bianchi, U. Bianchi, *Hum. Reprod.* 2000, 15, 1112-1116.
D. Seo, Y. Agca, Z. C. Feng, J. K. Critser, *Microfluid. Nanofluid.* 2007, 3, 561-570.
De Lamirande, E., San Gabriel, M., Zini, A. Human sperm chromatic undergoes physiological remodeling during in vitro capacitation and acrosome reaction. *J. Androl.* 33, 1025-1035 (2012).
DiLuzio, W. R. et al. *Escherichia coli* swim on the right-hand side. *Nature* 435, 1271-4 (2005).
Dulberg C S, Stephens T (1993). The prevalence of infertility in Canada, 1991-1992: analysis of three national surveys. In: *The Prevalence of Infertility in Canada: Research Studies of the Royal Commission on New Reproductive Technologies*. Ottawa: Minister of Supply and Services Canada, 61-106.

E. A. Gaffney, H. Gadêlha, D. J. Smith, J. R. Blake, J. C. Kirkman-Brown, *Annu. Rev.* Fluid Mech. 2011, 43, 501-528.

E. V. A. Åkerlöf, B. Fredricson, O. Gustafsson, A. Lundin, N. O. Lunell, L. Nylund, L. Rosenborg, Å. Pousette, *Int. J. Androl.* 1987, 10, 663-669.

F. L. Ng, D. Y. Liu, H. W. G. Baker, *Hum. Reprod.* 1992, 7, 261-266.

G. Huszar, A. Jakab, D. Sakkas, C-C. Ozenci, S. Cayli, E. Delpiano, S. Ozkavukcu, *Reprod. BioMed. Online* 2007, 14, 650-663.

G. M. Whitesides, *Nature* 2006, 442, 368-373.

G. Palermo, H. Joris, P. Devroey, A. C. Van Steirteghem, *Lancet* 1992, 340, 17-18.

Han, C., Zhang, Q., Ma, R., Xie, L., Qiu, T., Wang, L., et al. (2010). Integration of single oocyte trapping, in vitro fertilization and embryo culture in a microwell-structured microfluidic device. *Lab on a Chip,* 10(21): 2848-2854.

J. C. Kirkman-Brown, D. J. Smith, *Mol. Hum. Reprod.* 2011, 17, 539-544.

J. Erenpreiss, M. Spano, J. Erenpreisa, M. Bungum, A. Giwercman, *Asian J. Androl.* 2006, 8, 11-29.

K. C. Worrilow, S. Eid, D. Woodhouse, M. Perloe, S. Smith, J. Witmyer, K. Ivani, C. Khoury, G. D. Ball, T. Elliot, J. Lieberman, *Hum. Reprod.* 2013, 28, 306-314.

K. Haubert, T. Drier, D. Beebe, *Lab Chip* 2006, 6, 1548-9.

Kantsler, V., Dunkel, J., Polin, M., Goldstein, R. E. Ciliary contact interactions dominate surface scattering of swimming eukaryotes. *PNAS* 110, 1187-1192 (2013).

Katz, D. F, Pedrotti, L. Geotaxis by Motile Spermatozoa: Hydrodynamic Reorientation. *J. theor. Biol.* 67, 723-732 (1977).

Kricka, L. J., Nozaki, O., Heyner, S., Garside, W. T., Wilding, P. Applications of a microfabricated device for evaluating sperm function. *Clin Chem.* 39, 1944-1947 (1993).

L. Mazutis, J. Gilbert, W. L. Ung, D. A. Weitz, A. D. Griffiths, J. A. Heyman, *Nat. Protoc.* 2013, 8, 870-891.

L. Parmegiani, G. E. Cognigni, W. Ciampaglia, P. Pocognoli, F. Marchi, M. Filicori, *J. Assist. Reprod. Genet.* 2010, 27, 13-16, L. Xie, R. Ma, C. Han, K. Su, Q. Zhang, T. Qiu, L. Wang, G. Huang, J. Qiao, J. Wang, J. Cheng, *Clin. Chem.* 2010, 56, 1270-1278.

L. Y. Yeo, H-C. Chang, P. P. Y. Chan, J. R. Friend, *Small* 2011, 7, 12-48.

M. A. Unger, H-P. Chou, T. Thorsen, A. Scherer, S. R. Quake, *Science* 2000, 288, 113-116.

M. Antinori, E. Licata, G. Dani, F. Cerusico, C. Versaci, D. D'Angelo, S. Antinori, *Reprod. BioMed. Online* 2008, 16, 835-841.

M. Bungum, L. Bungum, A. Giwercman, *Asian J. Androl.* 2011, 13, 69-75.

M. Enciso, M. Iglesias, I. Galán, J. Sarasa, A. Gosálvez, J. Gosálvez, *Asian J. Androl.* 2011, 13, 764-768.

Makler, A., Stoller, J., Blumenfeld, Z., Feigin, P. D., Brandes, J. M. Investigation in real time of the effect of gravitation on human spermatozoa and their tendency to swim-up and swim-down. *Int J Androl.* 16, 251-257 (1993).

Mortimer, D. (2000). Sperm Preparation Methods. *J Androl.* 21, 357-366.

Niederberger C (2004). Do not let technician biases fool you: Frozen sperm from any azoospermic man is as good as fresh for ICSI and easier for the couple. *Urology* 64(6):1072-1074.

Norris S (2001). Reproductive Infertility: Prevalence, Causes, Trends, and Treatments. *Parliamentary Research Branch, Library of Parliament.*

Nosrati, R. et al. Rapid Selection of Sperm with High DNA Integrity. *Lab on a Chip.* (Submitted November 2013).

OVO Consulting (2009). In-vitro fertilization in Canada: Cost structure analysis. Prepared for *Canadian Fertility and Andrology Society.*

P. Denissenko, V. Kantsler, D. J. Smith, J. Kirkman-Brown, *Proc. Natl. Acad. Sci. U.S.A.* 2012, 109, 8007-8010.

P. Galajda, J. Keymer, P. Chaikin, R. Austin, *J. Bacteriol.* 2007, 189, 8704-8707.

Pierson R, Yupze A, Bissonnette F (2011). Human Assisted Reproduction live birth rates for Canada 2011. *Canadian Fertility and Andrology Society,* Press Release.

R. E. Jackson, C. L. Bormann, P. A. Hassun, A. M. Rocha, E. L. A. Motta, P. C. Serafini, G. D. Smith, *Fertil. Steril.* 2010, 94, 2626-2630.

R. J. Aitken, A. R. Hanson, L. Kuczera, *Hum. Reprod.* 2011, 26, 1955-1964.

R. J. Aitken, J. S. Clarkson, *J. Androl.* 1988, 9, 367-376.

R. M. Schultz, C. J. Williams, *Science* 2002, 296, 2188-2190.

R. Matsuura, T. Takeuchi, A. Yoshida, *Asian J. Androl.* 2010, 12, 753-9.

Raya, A., Izpisúa Belmonte J. C. Left-right asymmetry in the vertebrate embryo: from early information to higher-level integration. *Nat Rev Genet.* 7, 283-93 (2006).

Roberts, A. M. Gravitational Separation of X and Y Spermatozoa. *Nature* 238, 223-225 (1972).

Rothschild, L. Non-random Distribution of Bull Spermatozoa in a Drop of Sperm Suspension. *Nature* 198, 1221-1222 (1963).

S. D. Fleming, R. S. Ilad, A-M. G. Griffin, Y. Wu, K. J. Ong, H. C. Smith, R. J. Aitken, *Hum. Reprod.* 2008, 23, 2646-2651.

S. S. Suarez, A. A. Pacey, *Hum. Reprod. Update* 2006, 12, 23-37.

S. Tasoglu, H. Safaee, X. Zhang, J. L. Kingsley, P. N. Catalano, U. A. Gurkan, A. Nureddin, E. Kayaalp, R. M. Anchan, R. L. Maas, E. Tüzel, U. Demirci, *Small* 2013, DOI: 10.1002/smll.201300020.

Suh, R., Takayama, S., Smith, G. D. Microfluidic applications for andrology. *J Androl.* 26, 664-670 (2005).

T. G. Schuster, B. Cho, L. M. Keller, S. Takayama, G. D. Smith, *Reprod. BioMed. Online* 2003, 7, 75-81.

T. M. Said, J. A. Land, *Hum. Reprod. Update* 2011, 17, 719-733.

Tomlinson, M. J., Kessopoulou, E., Barratt, C. L. R. The diagnostic and prognostic value of traditional semen parameters. *J Androl.* 5, 588-593 (1999).

Winet, H., Bernstein, G. S., Head, J. Observations on the response of human spermatozoa to gravity, boundaries and fluid shear. *J. Reprod. Fed.* 70, 511-523 (1984).

Wolf D P, Byrd W, Dandekar P, Quigley M M (1984). Sperm Concentration and the Fertilization of Human Eggs In Vitro. *Biology of Reproduction* 31:837-848.

World Health Organization (2010). WHO laboratory manual for the Examination and processing of human semen, 5th Edition.

X. Mu, W. Zheng, J. Sun, W. Zhang, X. Jiang, *Small* 2013, 9, 9-21.

X. Zhang, I. Khimji, U. A. Gurkan, H. Safaee, P. N. Catalano, H. O. Keles, E. Kayaalp, U. Demirci, *Lab Chip* 2011, 11, 2535-2540.

Y-J. Ko, J-H. Maeng, B-C. Lee, S. Lee, S. Y. Hwang, Y. Ahn, *Anal. Sci.* 2012, 28, 27-32.

Yuzpe A, Pierson R, Daya S, Graves G (2002). Human Assisted Reproduction live birth rates for Canada 2002. *Canadian Fertility and Andrology Society*, Press Release.

Zini, A. et al. Prevalence of abnormal sperm DNA denaturation in fertile and infertile men. *Urology*. 60, 1069-1072 (2002).

Zini. A., Boman, J. M., Belzile, E., Ciampi, A. Sperm DNA damage is associated with an increased risk of pregnancy loss after IVF and ICSI: Systematic review and meta-analysis. *Hum Reprod*. 23, 2663-2668 (2008).

We claim:

1. An apparatus for separating sperm, the apparatus being configured to provide a static flow environment when filled with a buffer fluid, the apparatus comprising:
   an inlet reservoir for receiving a sample of semen;
   an outlet reservoir for collecting sperm separated from the sample; and
   a radial array of microchannels disposed between the inlet reservoir and the outlet reservoir to provide fluid communication therebetween, the radial array of microchannels being configured to direct motile sperm inwardly from the inlet reservoir to the outlet reservoir in the absence of flow within the radial array of microchannels.

2. The apparatus of claim 1, wherein the radial array of microchannels comprises a plurality of microchannel paths between the inlet reservoir and the outlet reservoir, each microchannel path comprising a path outlet adjacent the outlet reservoir, and at least one path inlet adjacent the inlet reservoir.

3. The apparatus of claim 2, wherein a width of each microchannel path is between 50 µm and 300 µm, and wherein a height of each microchannel path is between 25 µm and 100 µm.

4. The apparatus of claim 3, wherein the width of each microchannel path is between 100 µm and 200 µm, and wherein the height of each microchannel path is between 50 µm and 75 µm.

5. The apparatus of claim 2, wherein a length of each microchannel path is between 6 mm and 9 mm.

6. The apparatus of claim 2, wherein the plurality of microchannel paths comprises at least 200 microchannel paths between the inlet reservoir and the outlet reservoir.

7. The apparatus of claim 2, wherein the at least one path inlet for each microchannel path comprises two path inlets separated by a dividing wall member.

8. The apparatus of claim 1, further comprising a plurality of anti-return members located within the outlet reservoir and configured to restrict motile sperm from re-entering the radial array of microchannels after exiting the radial array of microchannels.

9. The apparatus of claim 1, wherein the apparatus comprises at least one additional radial array of microchannels layered on top of another the radial array of microchannels.

10. A method for separating sperm, the method comprising:
    providing an apparatus configured to provide a static flow environment when filled with a buffer fluid, the apparatus comprising:
      an inlet reservoir for receiving a sample of semen;
      an outlet reservoir for collecting sperm separated from the sample; and
      a radial array of microchannels disposed between the inlet reservoir and the outlet reservoir to provide fluid communication therebetween, the radial array of microchannels being configured to direct motile sperm inwardly from the inlet reservoir to the outlet reservoir in the absence of flow within the radial array of microchannels;
    filling the inlet reservoir, the outlet reservoir, and the radial array of microchannels with buffer fluid;
    introducing a sample of semen into the inlet reservoir; and
    retrieving the sperm separated from the sample from the outlet reservoir.

11. The method of claim 10, further comprising covering the outlet reservoir with an outlet closure member prior to the introducing act, and uncovering the outlet reservoir prior to the retrieving act.

12. The method of claim 10, further comprising covering the inlet reservoir with an inlet closure member after the introducing act.

* * * * *